US012569627B2

(12) United States Patent
    Germinario et al.

(10) Patent No.: US 12,569,627 B2
(45) Date of Patent: Mar. 10, 2026

(54) DROPLET DEVICE WITH EJECTOR CLOSURE

(71) Applicant: PNEUMA RESPIRATORY, INC., Boone, NC (US)

(72) Inventors: Louis Thomas Germinario, Kingsport, TN (US); John H. Hebrank, Durham, NC (US); Charles Eric Hunter, Boone, NC (US); Jack C. Hunter, Boone, NC (US); Chengjie Li, Shenzhen (CN); Christopher W. Maurer, Irvine, CA (US)

(73) Assignee: PNEUMA RESPIRATORY, INC., Boone, NC (US)

( * ) Notice: Subject to any disclaimer, the term of this patent is extended or adjusted under 35 U.S.C. 154(b) by 0 days.

(21) Appl. No.: 19/052,897

(22) Filed: Feb. 13, 2025

(65) Prior Publication Data

US 2025/0177662 A1      Jun. 5, 2025

Related U.S. Application Data

(63) Continuation of application No. 18/423,946, filed on Jan. 26, 2024, which is a continuation of application (Continued)

(51) Int. Cl.
    *A61M 11/00*          (2006.01)
    *A24F 40/05*          (2020.01)
    (Continued)

(52) U.S. Cl.
    CPC ........... *A61M 11/005* (2013.01); *A24F 40/05* (2020.01); *A24F 40/10* (2020.01); *A24F 40/30* (2020.01);
    (Continued)

(58) Field of Classification Search
    CPC ............ A61M 15/001; A61M 15/0081; A61M 15/0085; A61M 15/0091; A61M 15/0093;
    (Continued)

(56) References Cited

U.S. PATENT DOCUMENTS 3,934,585  A      1/1976  Maurice
3,970,250  A      7/1976  Drews
    (Continued)

FOREIGN PATENT DOCUMENTS

AU        2012258488        1/2013
CN        1788806          6/2006
    (Continued)

OTHER PUBLICATIONS

Extended European Search Report for EP 25177791.8, dated Aug. 28, 2025, 10 pages.

(Continued)

*Primary Examiner* — Joseph D. Boecker

(74) *Attorney, Agent, or Firm* — Polsinelli PC

(57)                ABSTRACT

An electronic droplet delivery device includes a housing including a mouthpiece located at an airflow exit side of the housing, a fluid reservoir, an aperture plate having a plurality of openings that receives fluid from the reservoir, an electronic actuator that oscillates the aperture plate to generate an ejected stream of droplets, and an ejector closure that opens and closes to help seal and prevent evaporation from the aperture plate when the droplet delivery device is not being used.

27 Claims, 35 Drawing Sheets

502

Related U.S. Application Data

No. 18/169,558, filed on Feb. 15, 2023, now abandoned, which is a continuation of application No. 16/098,698, filed as application No. PCT/US2017/030913 on May 3, 2017, now abandoned.

(60) Provisional application No. 62/471,929, filed on Mar. 15, 2017, provisional application No. 62/448,796, filed on Jan. 20, 2017, provisional application No. 62/428,696, filed on Dec. 1, 2016, provisional application No. 62/422,932, filed on Nov. 16, 2016, provisional application No. 62/416,026, filed on Nov. 1, 2016, provisional application No. 62/399,091, filed on Sep. 23, 2016, provisional application No. 62/354,437, filed on Jun. 24, 2016, provisional application No. 62/334,076, filed on May 10, 2016, provisional application No. 62/332,352, filed on May 5, 2016, provisional application No. 62/331,328, filed on May 3, 2016.

(51) Int. Cl.

| | |
|---|---|
| *A24F 40/10* | (2020.01) |
| *A24F 40/30* | (2020.01) |
| *A61B 5/08* | (2006.01) |
| *A61B 5/087* | (2006.01) |
| *A61B 5/091* | (2006.01) |
| *A61M 15/00* | (2006.01) |
| *A61M 15/02* | (2006.01) |
| *A61M 16/00* | (2006.01) |
| *A61M 16/10* | (2006.01) |
| *A61M 16/14* | (2006.01) |
| *B05B 17/06* | (2006.01) |
| *G16H 50/20* | (2018.01) |
| *G16H 50/30* | (2018.01) |

(52) U.S. Cl.
CPC .............. *A61B 5/082* (2013.01); *A61B 5/087* (2013.01); *A61M 11/001* (2014.02); *A61M 11/003* (2014.02); *A61M 15/0003* (2014.02); *A61M 15/001* (2014.02); *A61M 15/002* (2014.02); *A61M 15/0021* (2014.02); *A61M 15/0065* (2013.01); *A61M 15/0081* (2014.02); *A61M 15/0085* (2013.01); *A61M 15/0091* (2013.01); *A61M 15/025* (2014.02); *A61M 16/0051* (2013.01); *A61M 16/0066* (2013.01); *A61M 16/021* (2017.08); *A61M 16/107* (2014.02); *A61M 16/108* (2014.02); *A61M 16/14* (2013.01); *A61M 16/142* (2014.02); *B05B 17/06* (2013.01); *G16H 50/20* (2018.01); *G16H 50/30* (2018.01); *A61B 5/0816* (2013.01); *A61B 5/091* (2013.01); *A61M 11/002* (2014.02); *A61M 15/00* (2013.01); *A61M 15/0035* (2014.02); *A61M 2016/0018* (2013.01); *A61M 2016/0021* (2013.01); *A61M 2016/0027* (2013.01); *A61M 2016/0036* (2013.01); *A61M 2016/0039* (2013.01); *A61M 16/022* (2017.08); *A61M 16/024* (2017.08); *A61M 16/10* (2013.01); *A61M 16/1075* (2013.01); *A61M 2205/0233* (2013.01); *A61M 2205/0238* (2013.01); *A61M 2205/0294* (2013.01); *A61M 2205/103* (2013.01); *A61M 2205/27* (2013.01); *A61M 2205/276* (2013.01); *A61M 2205/33* (2013.01); *A61M 2205/3306* (2013.01); *A61M 2205/3313* (2013.01); *A61M 2205/3327* (2013.01); *A61M 2205/3331* (2013.01); *A61M 2205/3334* (2013.01); *A61M 2205/3553* (2013.01); *A61M 2205/3569* (2013.01); *A61M 2205/3584* (2013.01); *A61M 2205/3592* (2013.01); *A61M 2205/502* (2013.01); *A61M 2205/505* (2013.01); *A61M 2205/52* (2013.01); *A61M 2205/583* (2013.01); *A61M 2205/584* (2013.01); *A61M 2205/587* (2013.01); *A61M 2205/6018* (2013.01); *A61M 2205/6072* (2013.01); *A61M 2205/7536* (2013.01); *A61M 2205/8206* (2013.01); *A61M 2206/11* (2013.01); *A61M 2207/00* (2013.01); *A61M 2230/06* (2013.01); *A61M 2230/205* (2013.01); *A61M 2230/30* (2013.01); *A61M 2230/40* (2013.01)

(58) Field of Classification Search
CPC ............ A61M 15/0096; A61M 15/025; A61M 11/001; A61M 11/005; A24F 40/05; A24F 40/10; A24F 40/49; A24F 40/50
See application file for complete search history.

(56) References Cited

U.S. PATENT DOCUMENTS

| | | | |
|---|---|---|---|
| 5,021,701 | A | 6/1991 | Takahashi et al. |
| 5,027,809 | A | 7/1991 | Robinson |
| 5,134,993 | A | 8/1992 | Van Der Linden |
| 5,164,740 | A | 11/1992 | Ivri |
| 5,239,993 | A | 8/1993 | Evans |
| 5,363,842 | A | 11/1994 | Mishelevich et al. |
| 5,487,378 | A | 1/1996 | Robertson et al. |
| 5,487,738 | A | 1/1996 | Sciulli |
| 5,586,550 | A | 12/1996 | Ivri et al. |
| 5,607,410 | A | 3/1997 | Branch |
| 5,630,793 | A | 5/1997 | Rowe |
| 5,724,378 | A | 3/1998 | McAughey |
| 5,724,959 | A | 3/1998 | McAughey et al. |
| 5,758,637 | A | 6/1998 | Ivri et al. |
| 5,826,570 | A | 10/1998 | Goodman et al. |
| 5,828,394 | A | 10/1998 | Khuri-Yakub et al. |
| 5,848,588 | A | 12/1998 | Foley |
| 5,881,716 | A | 3/1999 | Wirch et al. |
| 5,884,620 | A | 3/1999 | Gonda et al. |
| 5,894,841 | A | 4/1999 | Voges |
| 5,906,202 | A | 5/1999 | Schuster et al. |
| 5,938,117 | A | 8/1999 | Ivri |
| 5,979,247 | A | 11/1999 | Kizawa |
| 6,011,062 | A | 1/2000 | Schneider et al. |
| 6,026,809 | A | 2/2000 | Abrams et al. |
| 6,062,212 | A | 5/2000 | Davison et al. |
| 6,071,498 | A | 6/2000 | Narodylo et al. |
| 6,085,740 | A | 7/2000 | Ivri et al. |
| 6,158,431 | A | 12/2000 | Poole |
| 6,176,234 | B1 | 1/2001 | Salter |
| 6,196,218 | B1 | 3/2001 | Voges |
| 6,196,219 | B1 | 3/2001 | Hess et al. |
| 6,235,177 | B1 | 5/2001 | Borland et al. |
| 6,358,058 | B1 | 3/2002 | Strupat et al. |
| 6,401,712 | B1 | 6/2002 | von Schuckmann |
| 6,443,146 | B1 | 9/2002 | Voges |
| 6,511,718 | B1 | 1/2003 | Paz de Araujo et al. |
| 6,615,826 | B1 | 9/2003 | Gabrio et al. |
| 6,629,524 | B1 | 10/2003 | Goodall et al. |
| 6,637,430 | B1 | 10/2003 | Voges et al. |
| 6,896,910 | B2 | 5/2005 | Kim et al. |
| 6,978,941 | B2 | 12/2005 | Litherland et al. |
| 6,981,499 | B2 | 1/2006 | Anderson et al. |
| 7,131,599 | B2 | 11/2006 | Katase |
| 7,191,777 | B2 | 3/2007 | Brand et al. |
| 7,198,044 | B2 | 4/2007 | Trueba |
| 7,219,664 | B2 | 5/2007 | Ruckdeschel et al. |
| 7,628,339 | B2 | 12/2009 | Ivri et al. |
| 7,648,957 | B2 | 1/2010 | Heyden et al. |
| 7,708,011 | B2 | 5/2010 | Hochrainer et al. |
| 7,883,031 | B2 | 2/2011 | Collins, Jr. et al. |

(56) References Cited

U.S. PATENT DOCUMENTS

| | | | |
|---|---|---|---|
| 7,900,625 B2 | 3/2011 | Kleinstreuer et al. |
| 7,954,486 B2 | 6/2011 | Papania et al. |
| 7,976,140 B2 | 7/2011 | Umeda |
| 8,012,136 B2 | 9/2011 | Collins, Jr. et al. |
| 8,367,734 B1 | 2/2013 | Gao et al. |
| 8,474,452 B2 | 7/2013 | Gumaste et al. |
| 8,545,463 B2 | 10/2013 | Collins, Jr. et al. |
| 8,555,874 B2 | 10/2013 | Fink et al. |
| 8,616,195 B2 | 12/2013 | Power et al. |
| 8,684,980 B2 | 4/2014 | Hunter et al. |
| 8,733,935 B2 | 5/2014 | Ballou, Jr. et al. |
| 8,753,308 B2 | 6/2014 | Palmer et al. |
| 8,936,021 B2 | 1/2015 | Collins, Jr. |
| 8,985,100 B2 | 3/2015 | Minocchieri et al. |
| 9,022,027 B2 | 5/2015 | Addington et al. |
| 9,087,145 B2 | 7/2015 | Ballou, Jr. et al. |
| 9,227,029 B2 | 1/2016 | Addington et al. |
| 9,242,054 B2 | 1/2016 | Fink et al. |
| 9,452,274 B2 | 9/2016 | Addington et al. |
| 9,463,486 B2 | 10/2016 | Wilkerson et al. |
| 9,539,604 B2 | 1/2017 | Wilkerson et al. |
| 9,956,360 B2 | 5/2018 | Germinario et al. |
| 9,962,507 B2 | 5/2018 | Germinario et al. |
| 10,449,314 B2 | 10/2019 | Germinario et al. |
| 10,525,220 B2 | 1/2020 | Hunter et al. |
| 10,568,543 B2 | 2/2020 | Yan |
| 10,857,310 B2 | 12/2020 | Muellinger |
| 10,898,666 B2 | 1/2021 | Germinario et al. |
| 11,285,274 B2 | 3/2022 | Germinario et al. |
| 11,285,283 B2 | 3/2022 | Germinario et al. |
| 11,285,284 B2 | 3/2022 | Germinario et al. |
| 11,285,285 B2 | 3/2022 | Germinario et al. |
| 11,458,267 B2 | 10/2022 | Hebrank et al. |
| 11,738,158 B2 | 8/2023 | Hebrank et al. |
| 11,771,852 B2 | 10/2023 | Maurer et al. |
| 12,161,795 B2 | 12/2024 | Rapp et al. |
| 2002/0002975 A1 | 1/2002 | Power |
| 2002/0032387 A1 | 3/2002 | Geva et al. |
| 2002/0046750 A1 | 4/2002 | Gonda et al. |
| 2002/0071871 A1 | 6/2002 | Snyder et al. |
| 2002/0077369 A1 | 6/2002 | Noolandi et al. |
| 2002/0121274 A1 | 9/2002 | Borland et al. |
| 2002/0129812 A1 | 9/2002 | Litherland et al. |
| 2002/0129813 A1 | 9/2002 | Litherland et al. |
| 2002/0134372 A1 | 9/2002 | Loeffler et al. |
| 2003/0019493 A1 | 1/2003 | Narayan et al. |
| 2003/0062042 A1 | 4/2003 | Wensley et al. |
| 2003/0072717 A1 | 4/2003 | Reinhold et al. |
| 2003/0098022 A1 | 5/2003 | Nakao et al. |
| 2003/0101991 A1 | 6/2003 | Trueba |
| 2003/0127538 A1 | 7/2003 | Patel et al. |
| 2003/0140921 A1* | 7/2003 | Smith ............... A61M 15/0031 |
| | | 128/200.14 |
| 2003/0150445 A1 | 8/2003 | Power et al. |
| 2003/0196654 A1 | 10/2003 | Stein |
| 2003/0205229 A1 | 11/2003 | Crockford et al. |
| 2004/0009231 A1 | 1/2004 | Jackson et al. |
| 2004/0045547 A1 | 3/2004 | Yamamoto et al. |
| 2004/0084044 A1 | 5/2004 | Chilers et al. |
| 2004/0139963 A1 | 7/2004 | Ivri et al. |
| 2004/0195403 A1 | 10/2004 | Atterybury et al. |
| 2004/0215157 A1 | 10/2004 | Peclat et al. |
| 2004/0256487 A1 | 12/2004 | Collins, Jr. et al. |
| 2005/0011514 A1 | 1/2005 | Power et al. |
| 2005/0077315 A1 | 4/2005 | Pavlu et al. |
| 2005/0121025 A1 | 6/2005 | Gamard et al. |
| 2005/0150489 A1 | 7/2005 | Dunfield |
| 2005/0166912 A1 | 8/2005 | Sexton et al. |
| 2005/0172476 A1 | 8/2005 | Stone et al. |
| 2005/0172958 A1 | 8/2005 | Singer et al. |
| 2005/0217666 A1 | 10/2005 | Fink et al. |
| 2005/0224075 A1 | 10/2005 | Childers et al. |
| 2005/0236501 A1 | 10/2005 | Zimlich et al. |
| 2006/0253045 A1 | 11/2006 | Coifman |
| 2007/0023036 A1 | 2/2007 | Grychowski et al. |
| 2007/0044793 A1 | 3/2007 | Kleinstreuer et al. |
| 2007/0062519 A1 | 3/2007 | Wuttke et al. |
| 2007/0083677 A1 | 4/2007 | Cecka et al. |
| 2007/0119968 A1 | 5/2007 | Collins, Jr. et al. |
| 2007/0119969 A1 | 5/2007 | Collins, Jr. et al. |
| 2007/0125370 A1 | 6/2007 | Denyer et al. |
| 2007/0157931 A1 | 7/2007 | Parker et al. |
| 2007/0240714 A1 | 10/2007 | Dunne et al. |
| 2007/0248645 A1 | 10/2007 | Bague et al. |
| 2007/0267010 A1 | 11/2007 | Fink et al. |
| 2008/0000470 A1 | 1/2008 | Minocchieri et al. |
| 2008/0059228 A1 | 3/2008 | Bossi et al. |
| 2008/0110453 A1 | 5/2008 | Ross et al. |
| 2008/0142010 A1 | 6/2008 | Weaver et al. |
| 2008/0243050 A1 | 10/2008 | Power et al. |
| 2008/0271732 A1 | 11/2008 | Weaver et al. |
| 2008/0283049 A1 | 11/2008 | Mahoney et al. |
| 2008/0283057 A1 | 11/2008 | Rohrschneider et al. |
| 2008/0295827 A1 | 12/2008 | Kobayashi |
| 2008/0308096 A1 | 12/2008 | Borgschulte et al. |
| 2009/0038610 A1 | 2/2009 | Bogh et al. |
| 2009/0093772 A1 | 4/2009 | Genosar et al. |
| 2009/0101144 A1 | 4/2009 | Gamard et al. |
| 2009/0107492 A1 | 4/2009 | Ooida |
| 2009/0114218 A1 | 5/2009 | Veatch |
| 2009/0114742 A1 | 5/2009 | Collins, Jr. |
| 2009/0118243 A1 | 5/2009 | Gjorstrup |
| 2009/0134235 A1 | 5/2009 | Ivri |
| 2009/0167812 A1 | 7/2009 | Asai et al. |
| 2009/0192443 A1 | 7/2009 | Collins, Jr. |
| 2009/0212133 A1 | 8/2009 | Collins, Jr. |
| 2009/0223513 A1 | 9/2009 | Papania et al. |
| 2009/0235925 A1 | 9/2009 | Power et al. |
| 2009/0270752 A1 | 10/2009 | Coifman |
| 2009/0272818 A1 | 11/2009 | Alpey, III et al. |
| 2009/0314292 A1 | 12/2009 | Overfield et al. |
| 2009/0317496 A1 | 12/2009 | Park et al. |
| 2010/0000527 A1* | 1/2010 | Inoue .................. A61M 15/025 |
| | | 128/203.14 |
| 2010/0024814 A1 | 2/2010 | Sugita et al. |
| 2010/0037894 A1 | 2/2010 | Rouse et al. |
| 2010/0078013 A1 | 4/2010 | Power et al. |
| 2010/0083956 A1 | 4/2010 | Fukumoto et al. |
| 2010/0089395 A1 | 4/2010 | Power et al. |
| 2010/0154793 A1 | 6/2010 | Kobayashi et al. |
| 2010/0156995 A1 | 6/2010 | Kanda et al. |
| 2010/0181387 A1 | 7/2010 | Zaffaroni et al. |
| 2010/0186747 A1 | 7/2010 | Wachtel |
| 2010/0218760 A1 | 9/2010 | Anderson et al. |
| 2010/0222752 A1* | 9/2010 | Collins, Jr. ......... B05B 17/0623 |
| | | 604/296 |
| 2010/0273895 A1 | 10/2010 | Stinchcomb et al. |
| 2010/0282247 A1 | 11/2010 | Kadrichu et al. |
| 2011/0094523 A1 | 4/2011 | Thorens et al. |
| 2011/0108025 A1 | 5/2011 | Fink et al. |
| 2011/0114090 A1 | 5/2011 | Piper |
| 2011/0146670 A1 | 6/2011 | Gallem et al. |
| 2011/0230824 A1 | 9/2011 | Lillis et al. |
| 2011/0253139 A1 | 10/2011 | Guthrie et al. |
| 2011/0253140 A1 | 10/2011 | Smyth et al. |
| 2011/0253805 A1 | 10/2011 | Lee |
| 2012/0037154 A1 | 2/2012 | Gallem et al. |
| 2012/0048265 A1 | 3/2012 | Smaldone |
| 2012/0048266 A1 | 3/2012 | Alelov |
| 2012/0266870 A1 | 10/2012 | Denyer et al. |
| 2012/0266878 A1 | 10/2012 | Watanabe et al. |
| 2012/0291781 A1 | 11/2012 | Kaufmann et al. |
| 2013/0064777 A1 | 3/2013 | Tamarkin et al. |
| 2013/0079732 A1 | 3/2013 | Burt et al. |
| 2013/0150812 A1 | 6/2013 | Hunter et al. |
| 2013/0172830 A1 | 7/2013 | Hunter et al. |
| 2013/0239956 A1 | 9/2013 | Schultz et al. |
| 2013/0267864 A1 | 10/2013 | Addington et al. |
| 2013/0269694 A1 | 10/2013 | Patton et al. |
| 2013/0284165 A1 | 10/2013 | Krimsky |
| 2013/0299607 A1* | 11/2013 | Wilkerson .......... B05B 17/0661 |
| | | 239/328 |
| 2013/0319404 A1 | 12/2013 | Feriani et al. |
| 2013/0327323 A1 | 12/2013 | Rubin |

(56) References Cited

U.S. PATENT DOCUMENTS

| | | |
|---|---|---|
| 2013/0330400 A1 | 12/2013 | Perkins et al. |
| 2013/0334335 A1 | 12/2013 | Wilkerson et al. |
| 2013/0334339 A1 | 12/2013 | Xu |
| 2014/0037735 A1 | 2/2014 | Montgomery |
| 2014/0116426 A1 | 5/2014 | Mullinger et al. |
| 2014/0187969 A1 | 7/2014 | Hunter et al. |
| 2014/0190496 A1 | 7/2014 | Wensley et al. |
| 2014/0213925 A1 | 7/2014 | Chan et al. |
| 2014/0230817 A1 | 8/2014 | Richardson |
| 2014/0231538 A1 | 8/2014 | Tabata et al. |
| 2014/0261414 A1 | 9/2014 | Weitzel et al. |
| 2014/0283859 A1 | 9/2014 | Minskoff et al. |
| 2014/0309546 A1 | 10/2014 | Fazzi et al. |
| 2014/0336618 A1 | 11/2014 | Wilkerson et al. |
| 2014/0339323 A1 | 11/2014 | Bentvelsen et al. |
| 2015/0018694 A1 | 1/2015 | Gomo |
| 2015/0101596 A1 | 4/2015 | Hogan |
| 2015/0114407 A1 | 4/2015 | Duncan et al. |
| 2015/0136129 A1 | 5/2015 | Mahadevan et al. |
| 2015/0136155 A1 | 5/2015 | Verleur et al. |
| 2015/0164375 A1 | 6/2015 | Schindhelm et al. |
| 2015/0174348 A1 | 6/2015 | Tunnell et al. |
| 2015/0181945 A1 | 7/2015 | Tremblay |
| 2015/0196060 A1 | 7/2015 | Wensley et al. |
| 2015/0273165 A1 | 10/2015 | Hadash |
| 2015/0283339 A1 | 10/2015 | Mahadevan et al. |
| 2015/0328151 A1 | 11/2015 | Ballou, Jr. et al. |
| 2015/0352301 A1 | 12/2015 | Stedman et al. |
| 2015/0366268 A1 | 12/2015 | Shabat |
| 2016/0001018 A1 | 1/2016 | Fink et al. |
| 2016/0001019 A1 | 1/2016 | Fink et al. |
| 2016/0045682 A1 | 2/2016 | Boyden |
| 2016/0045685 A1 | 2/2016 | Hyde |
| 2016/0082208 A1 | 3/2016 | Ballam et al. |
| 2016/0106341 A1 | 4/2016 | Adam et al. |
| 2016/0129182 A1 | 5/2016 | Schuster et al. |
| 2016/0166768 A1 | 6/2016 | Edwards et al. |
| 2016/0213864 A1 | 7/2016 | Eilat et al. |
| 2016/0213866 A1 | 7/2016 | Tan |
| 2016/0245830 A1 | 8/2016 | Mace et al. |
| 2016/0310982 A1 | 10/2016 | Von Hollen |
| 2016/0325055 A1 | 11/2016 | Cameron |
| 2016/0331037 A1 | 11/2016 | Cameron |
| 2016/0354557 A1 | 12/2016 | McPherson Allnutt et al. |
| 2017/0007449 A1 | 1/2017 | Nielsen |
| 2017/0035924 A1 | 2/2017 | Yang et al. |
| 2017/0039344 A1 | 2/2017 | Bitran et al. |
| 2017/0106153 A1 | 4/2017 | Davidson et al. |
| 2017/0106155 A1 | 4/2017 | Reed et al. |
| 2017/0128677 A1 | 5/2017 | Eilat et al. |
| 2017/0158776 A1 | 6/2017 | Feltquate et al. |
| 2017/0203055 A1 | 7/2017 | Chen et al. |
| 2017/0203058 A1 | 7/2017 | Davidson et al. |
| 2017/0203323 A1 | 7/2017 | Gschwind et al. |
| 2017/0224706 A1 | 8/2017 | Surber |
| 2017/0232211 A1 | 8/2017 | Gallem et al. |
| 2017/0270260 A1 | 9/2017 | Shetty et al. |
| 2017/0274163 A1 | 9/2017 | Oliveras et al. |
| 2017/0304565 A1 | 10/2017 | Allosery |
| 2017/0304566 A1 | 10/2017 | Allosery |
| 2017/0319796 A1 | 11/2017 | Germinario et al. |
| 2017/0319797 A1 | 11/2017 | Germinario et al. |
| 2017/0333646 A1 | 11/2017 | Hemy et al. |
| 2018/0021528 A1 | 1/2018 | Hsieh et al. |
| 2018/0021530 A1 | 1/2018 | Fink et al. |
| 2018/0056018 A1 | 3/2018 | Canvin et al. |
| 2018/0116871 A1 | 5/2018 | Hunter et al. |
| 2018/0193175 A1 | 7/2018 | Bluecher et al. |
| 2018/0286208 A1 | 10/2018 | Baker et al. |
| 2018/0317557 A1 | 11/2018 | Monsees et al. |
| 2018/0344955 A1 | 12/2018 | Germinario et al. |
| 2018/0369515 A1 | 12/2018 | Germinario et al. |
| 2019/0117907 A1 | 4/2019 | Germinario et al. |
| 2019/0125985 A1 | 5/2019 | Germinario et al. |
| 2019/0125986 A1 | 5/2019 | Germinario et al. |
| 2019/0125987 A1 | 5/2019 | Germinario et al. |
| 2019/0134330 A1 | 5/2019 | Germinario et al. |
| 2019/0224426 A1 | 7/2019 | Farina et al. |
| 2019/0343793 A1 | 11/2019 | Gunther et al. |
| 2019/0358420 A1 | 11/2019 | Hunter et al. |
| 2019/0388627 A1 | 12/2019 | Kern |
| 2020/0060346 A1 | 2/2020 | Lau et al. |
| 2020/0147325 A1 | 5/2020 | Wilson et al. |
| 2020/0230329 A1 | 7/2020 | Danek |
| 2020/0246556 A1 | 8/2020 | Osoegawa et al. |
| 2020/0276398 A1 | 9/2020 | Hebrank et al. |
| 2020/0289770 A1 | 9/2020 | Hebrank et al. |
| 2020/0315842 A1 | 10/2020 | Palanker et al. |
| 2020/0345588 A1 | 11/2020 | Merrell et al. |
| 2020/0353186 A1 | 11/2020 | Hebrank et al. |
| 2021/0106772 A1 | 4/2021 | Hebrank et al. |
| 2021/0236745 A1 | 8/2021 | Germinario et al. |
| 2021/0275760 A1 | 9/2021 | Hunter et al. |
| 2022/0001122 A1 | 1/2022 | Hunter et al. |
| 2022/0080137 A1 | 3/2022 | Hebrank et al. |
| 2022/0226587 A1 | 7/2022 | Hunter et al. |
| 2022/0296823 A1 | 9/2022 | Hebrank et al. |
| 2022/0401661 A1 | 12/2022 | Hunter et al. |
| 2023/0000150 A1 | 1/2023 | Hebrank et al. |
| 2024/0181175 A1 | 6/2024 | Hebrank et al. |
| 2025/0041538 A1 | 2/2025 | Germinario et al. |

FOREIGN PATENT DOCUMENTS

| | | |
|---|---|---|
| CN | 2364248 | 8/2006 |
| CN | 101111276 A | 1/2008 |
| CN | 102218181 A | 10/2011 |
| CN | 102971755 A | 3/2013 |
| CN | 103785086 A | 5/2014 |
| CN | 104511072 | 4/2015 |
| CN | 104586396 A | 5/2015 |
| CN | 104602653 A | 5/2015 |
| CN | 104755180 A | 7/2015 |
| CN | 204995458 | 1/2016 |
| CN | 205019058 | 2/2016 |
| CN | 715947 | 11/2020 |
| EP | 2724741 | 4/2014 |
| JP | H09164205 A | 6/1997 |
| JP | H10122921 A | 5/1998 |
| JP | H10506037 A | 6/1998 |
| JP | H11-042219 | 2/1999 |
| JP | 2002536173 A | 10/2002 |
| JP | 2003159332 A | 6/2003 |
| JP | 2003-265994 | 9/2003 |
| JP | 2005199066 A | 7/2005 |
| JP | 2006501871 A | 1/2006 |
| JP | 2006-68508 | 3/2006 |
| JP | 2007075259 A | 3/2007 |
| JP | 2008178695 A | 8/2008 |
| JP | 2012510319 A | 5/2012 |
| JP | 2013255920 A | 12/2013 |
| JP | 2014083446 A | 5/2014 |
| JP | 2015513427 A | 5/2015 |
| KR | 20150020542 A | 2/2015 |
| KR | 10-2019-122453 | 10/2019 |
| WO | 199312823 | 7/1993 |
| WO | 199609846 | 4/1996 |
| WO | 199614163 | 5/1996 |
| WO | 199848873 | 11/1998 |
| WO | 200010634 | 3/2000 |
| WO | 200047335 | 8/2000 |
| WO | 200050112 | 8/2000 |
| WO | 200185244 | 11/2001 |
| WO | 200187378 | 11/2001 |
| WO | 2003020349 | 3/2003 |
| WO | 2003059413 | 7/2003 |
| WO | 2004078025 | 9/2004 |
| WO | 2006013952 | 2/2006 |
| WO | 2006083014 | 8/2006 |
| WO | 2006102345 | 9/2006 |
| WO | 2006108558 | 10/2006 |
| WO | 2007107160 | 9/2007 |
| WO | 2008056986 | 5/2008 |
| WO | 2008058941 | 5/2008 |

(56)             References Cited

FOREIGN PATENT DOCUMENTS

| | | |
|---|---|---|
| WO | 2008116165 | 9/2008 |
| WO | 2009012371 | 1/2009 |
| WO | 2009111612 | 9/2009 |
| WO | 2009111612 A1 | 9/2009 |
| WO | 2010065452 | 6/2010 |
| WO | 2011042212 | 4/2011 |
| WO | 201108377 | 7/2011 |
| WO | 2011091268 | 7/2011 |
| WO | 2012026963 | 3/2012 |
| WO | 2013090459 A1 | 6/2013 |
| WO | 2013098334 | 7/2013 |
| WO | 2013158352 | 10/2013 |
| WO | 2013158967 | 10/2013 |
| WO | 2013173321 | 11/2013 |
| WO | 2014147550 | 9/2014 |
| WO | 2015004554 | 1/2015 |
| WO | 2015106150 | 7/2015 |
| WO | 2015136529 | 9/2015 |
| WO | 2015176033 | 11/2015 |
| WO | 2015191478 | 12/2015 |
| WO | 2015191481 | 12/2015 |
| WO | 2016001923 | 1/2016 |
| WO | 2016001924 | 1/2016 |
| WO | 2016003738 | 1/2016 |
| WO | 2016019353 A1 | 2/2016 |
| WO | 2017015303 | 1/2017 |
| WO | 2017056103 | 4/2017 |
| WO | 2018213834 | 11/2018 |
| WO | 2019071008 | 4/2019 |
| WO | 2019079461 | 4/2019 |
| WO | 2019136437 | 7/2019 |
| WO | 2019219865 | 11/2019 |
| WO | 2020072478 | 4/2020 |
| WO | 2020141424 | 7/2020 |
| WO | 2020154497 | 7/2020 |
| WO | 2020227717 | 11/2020 |
| WO | 2020264501 | 12/2020 |
| WO | 2021090135 | 5/2021 |
| WO | 2021203038 | 10/2021 |
| WO | 2002226407 | 10/2022 |
| WO | 2022271848 A1 | 12/2022 |
| WO | 2023278551 A1 | 1/2023 |
| WO | 2023064477 | 4/2023 |

OTHER PUBLICATIONS

Final Office Action for U.S. Appl. No. 19/052,199, dated Sep. 22, 2025, 30 pages.
Final Office Action for U.S. Appl. No. 19/052,152, dated Aug. 28, 2025, 9 pages.
Notice of Allowance for U.S. Appl. No. 19/052,159, dated Sep. 10, 2025, 10 pages.
Communication Pursuant to Article 94(3) EPC for European Application No. 17793294.4, dated Jul. 18, 2024, 10 Pages.
Extended European Search Report for European Application No. 17793284.5, dated Dec. 10, 2019, 9 Pages.
Extended European Search Report for European Application No. 17793287.8, dated Dec. 4, 2019, 8 Pages.
Extended European Search Report for European Application No. 17793294.4, dated Mar. 17, 2020, 15 Pages.
International Preliminary Report on Patentability for International Application No. PCT/US2017/030913, dated Nov. 15, 2018, 8 Pages.
International Preliminary Report on Patentability for International Application No. PCT/US2017/030917, dated Nov. 15, 2018, 9 Pages.
International Preliminary Report on Patentability for International Application No. PCT/US2017/030919, dated Nov. 15, 2018, 10 Pages.
International Preliminary Report on Patentability for International Application No. PCT/US2017/030921, dated Nov. 15, 2018, 11 Pages.

International Preliminary Report on Patentability for International Application No. PCT/US2017/030925, dated Nov. 15, 2018, 9 Pages.
International Preliminary Report on Patentability for International Application No. PCT/US2017/030929, dated Nov. 15, 2018, 8 Pages.
International Search Report and Written Opinion for International Application No. PCT/US2017/30913, dated Jul. 17, 2017, 9 Pages.
International Search Report and Written Opinion for International Application No. PCT/US2017/30917, dated Jul. 21, 2017, 10 Pages.
International Search Report and Written Opinion for International Application No. PCT/US2017/30919, dated Aug. 1, 2017, 11 Pages.
International Search Report and Written Opinion for International Application No. PCT/US2017/30921, dated Aug. 4, 2017, 13 Pages.
International Search Report and Written Opinion for International Application No. PCT/US2017/30925, dated Oct. 2, 2017, 12 Pages.
International Search Report and Written Opinion for International Application No. PCT/US2017/30929, dated Jul. 27, 2017, 9 Pages.
Final Office Action for U.S. Appl. No. 19/052,194, dated Jul. 28, 2025, 17 pages.
Final Office Action for U.S. Appl. No. 19/052,182, dated Jul. 28, 2025, 26 pages.
Final Office Action for U.S. Appl. No. 19/052,132, dated Aug. 1, 2025, 18 pages.
Final Office Action for U.S. Appl. No. 19/052,634, dated Aug. 1, 2025, 26 pages.
Non-Final Office Action for U.S. Appl. No. 19/052,152, Aug. 28, 2025, 9 pages.
Notice of Allowance for U.S. Appl. No. 19/052,148, dated Sep. 8, 2025, 9 pages.
Non-Final Office Action for U.S. Appl. No. 18/423,946, dated Dec. 31, 2024, 77 pages.
Non-Final Office Action for U.S. Appl. No. 19/052,194, dated Apr. 10, 2025, 21 pages.
Non-Final Office Action for U.S. Appl. No. 19/052,199, dated Jun. 9, 2025, 30 pages.
Non-Final Office Action for U.S. Appl. No. 19/052,132, dated Apr. 24, 2025, 37 pages.
Non-Final Office Action for U.S. Appl. No. 19/052,634, dated Apr. 24, 2025, 40 pages.
Non-Final Office Action for U.S. Appl. No. 19/052,203, dated May 8, 2025, 28 pages.
Non-Final Office Action for U.S. Appl. No. 19/052,152, dated May 20, 2025, 26 pages.
Non-Final Office Action for U.S. Appl. No. 19/052,148, dated May 21, 2025, 35 pages.
Non-Final Office Action for U.S. Appl. No. 18/443,880, dated Apr. 7, 2025, 18 pages.
Non-Final Office Action for U.S. Appl. No. 19/052,173, dated Jun. 18, 2025, 22 pages.
Non-Final Office Action for U.S. Appl. No. 19/052,167, dated Jun. 4, 2025, 26 pages.
Non-Final Office Action for U.S. Appl. No. 19/052,159, dated May 21, 2025, 47 pages.
Non-Final Office Action for U.S. Appl. No. 19/052,182, dated Apr. 16, 2025, 39 pages.
Steller, Andrew, "Microcontroller Based Diagnostic Smart Inhaler," University of Cincinnati, Dec. 7, 2014, 63 pages [http://rave.ohiolink.edu/etdc/view?acc_num=ucin1445615167].
Copley, "Understanding cascade impaction and its importance for inhaler testing," Copley Scientific, Copley White Paper [serial online], Jul. 2007 [retrieved on May 7, 2017]. retrieved from the Internet: URL: http://www.copleyscientific.com/files/ww/articles/Understanding%20Cascade%20Impaction%20White%20Paper.pdf; 6 pages.
Kharitonov, "Exhaled markers of inflammatory lung diseases: ready for routine monitoring?" Swiss Med Wkly, 2004, vol. 134, pp. 175-192.
Broeders, et al., "Inhalation Profiles in Asthmatics and COPD Patients: Reproducibility and Effect of Instruction," Journal of Aerosol Medicine, vol. 16, No. 2, 2003, pp. 131-141.

(56) References Cited

OTHER PUBLICATIONS

Taube, et al., "Use of a portable device to record maximum inspiratory flow in relation to dyspnoea in patients with COPD," Respiratory Medicine, 2011, vol. 105, pp. 316.312.

Carvalho, et al., "The function and performance of aqueous aerosol devices for inhalation therapy," Journal of Pharmacy and Pharmacology, vol. 568., No. 5, Apr. 8, 2016, pp. 556-578.

Pneuma Respiratory, "Digitally breath-actuated inhaler device with precision droplet ejector technology and digital dose confidence," Available on Mar. 18, 2017, 3 pages [retrieved on Jun. 30, 2017]. Retrieved from the Internet: URL: https://pneumarespiratory.com/.

Extended European Search Report for Application No. 25179242.0 dated Oct. 17, 2025, 10 pages.

Notice of Allowance for U.S. Appl. No. 19/052,167, dated Oct. 1, 2025, 69 pages.

Final Office Action for U.S. Appl. No. 18/443,880, dated Nov. 26, 2025, 23 pages.

* cited by examiner

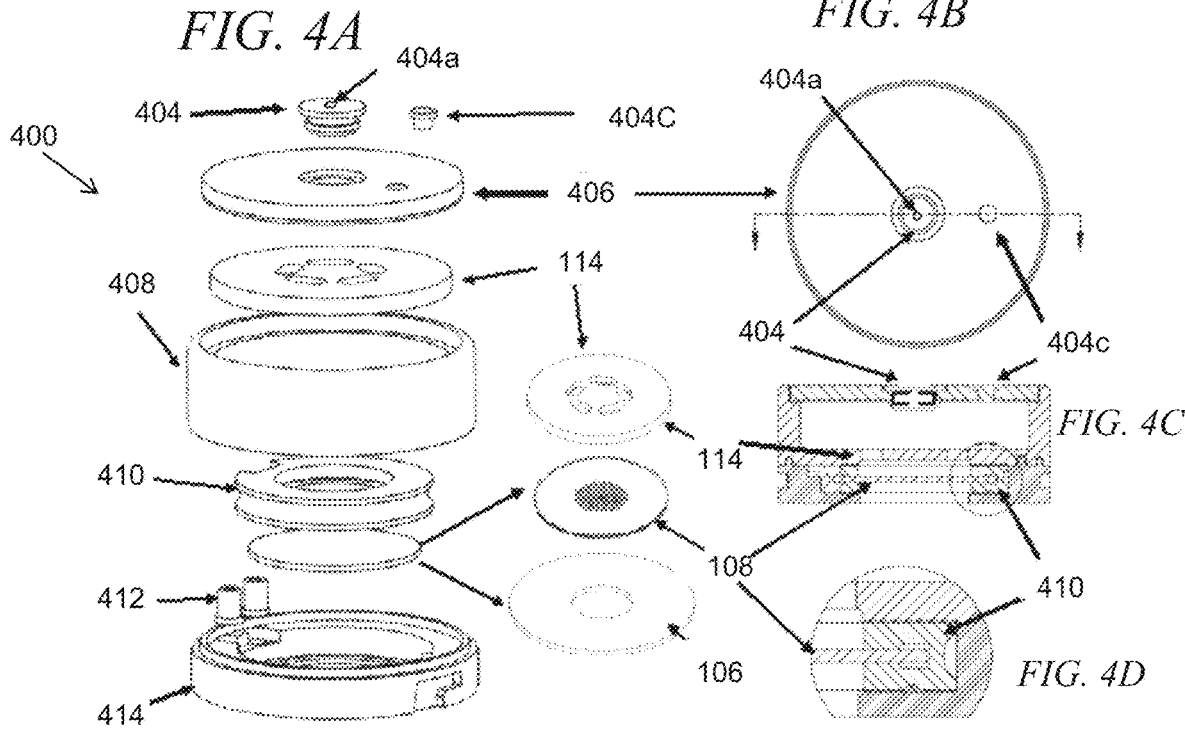
*FIG. 4A*
*FIG. 4B*
*FIG. 4C*
*FIG. 4D*
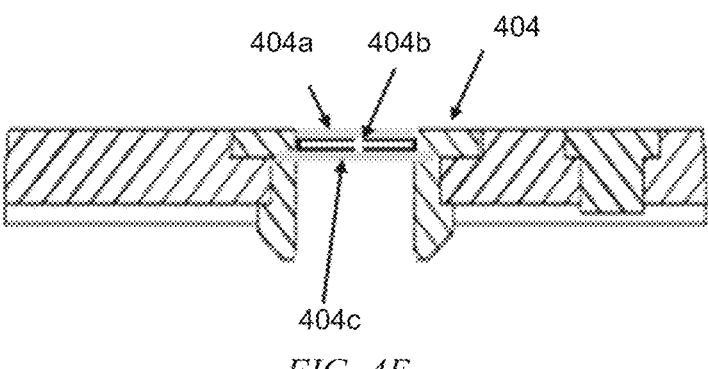
*FIG. 4E*

Effect of Number of Holes in the Air Inlet Laminar Flow Screen on Differential Pressure and Flow Rate

| | | | |
|---|---|---|---|
| ◈ | 29 holes; 1.9 mm diam. | ▥ | 23 holes; 1.9 mm diam. |
| ▵ | 17 holes; 1.9 mm diam. | —— | Poly. (29 holes; 1.9 mm diam.) |
| ••••• | Poly. (23 holes; 1.9 mm diam.) | — — • | Poly. (17 holes; 1.9 mm diam.) |

1.9 mm diameter;
29 holes

*FIG. 7A*          *FIG. 7B*
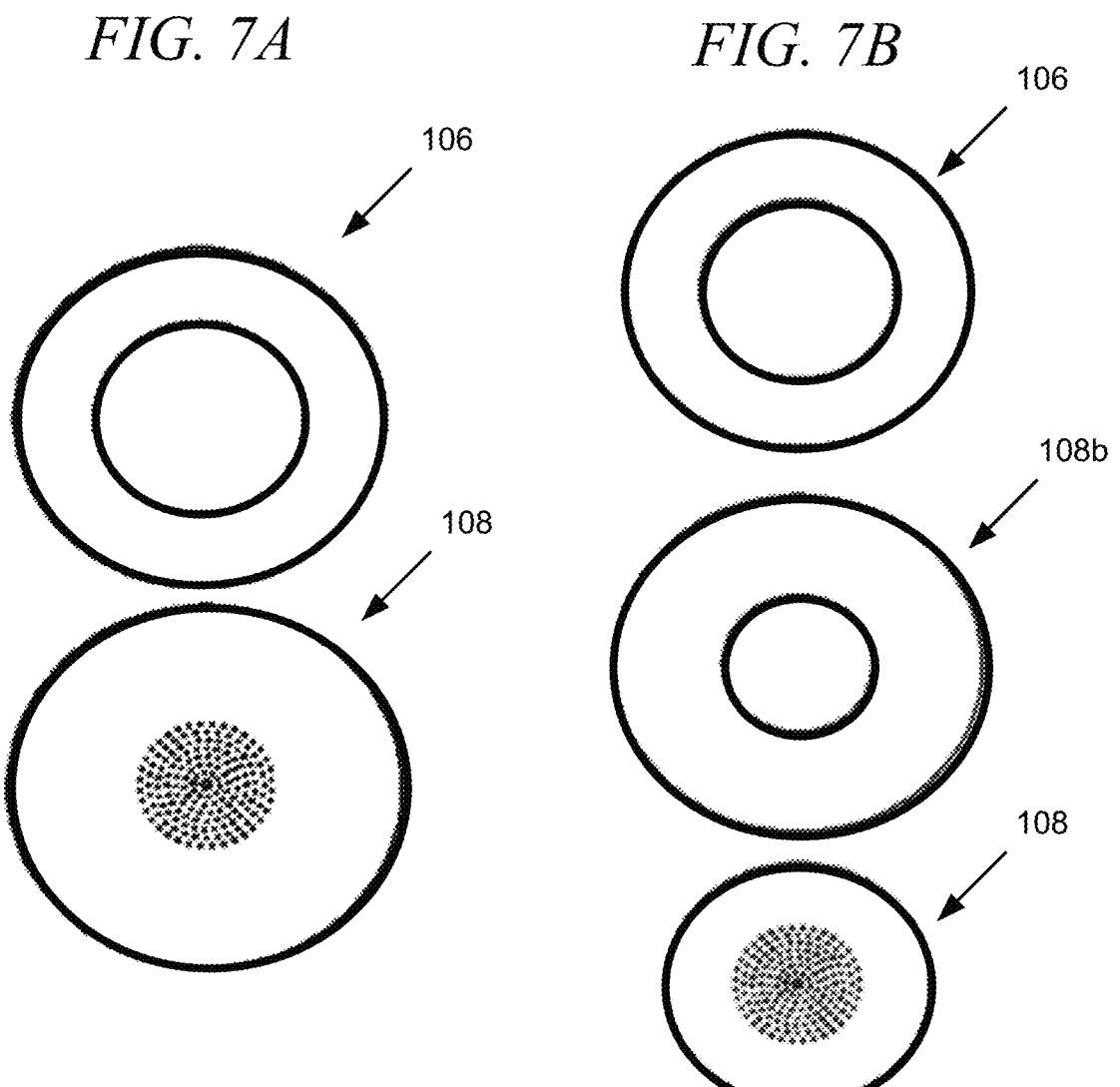

*FIG. 9*

Anderson Cascade Impactor Summary; Mouth, Throat, Coarse, Respirable and Fine Particle Fraction ■ Pneuma Inhaler

MMAD and GSD for All ACI Trials
Albuterol Sulfate 5,000ug/ml, Anderson Cascade constant flow 28.3lpm, Mean ± SD, N=30

■ MMAD  ■ GSD

**Pneuma Inhaler Throat, Coarse, Respirable and Fine Particle Fraction
Albuterol Sulfate 4,932 ug/ml, Anderson Cascade constant flow 28.3 lpm,
Mean ± SD, N=30**

DROPLET DEVICE WITH EJECTOR CLOSURE

CROSS REFERENCE TO RELATED APPLICATIONS

The present application is a continuation of U.S. application Ser. No. 18/423,946, entitled "DROPLET DELIVERY DEVICE FOR DELIVERY OF FLUIDS TO THE PULMONARY SYSTEM AND METHODS OF USE," filed on Jan. 26, 2024, which is a continuation of U.S. application Ser. No. 18/169,558, entitled "DROPLET DELIVERY DEVICE FOR DELIVERY OF FLUIDS TO THE PULMONARY SYSTEM AND METHODS OF USE," filed on Feb. 15, 2023, now abandoned, which is a continuation of U.S. application Ser. No. 16/098,698, entitled "DROPLET DELIVERY DEVICE FOR DELIVERY OF FLUIDS TO THE PULMONARY SYSTEM AND METHODS OF USE," filed on Nov. 2, 2018, now abandoned, which is a national stage filing under 35 U.S.C. § 371 of PCT Application No. PCT/US2017/030913, entitled "DROPLET DELIVERY DEVICE FOR DELIVERY OF FLUIDS TO THE PULMONARY SYSTEM AND METHODS OF USE," filed on May 3, 2017, which claims benefit under 35 U.S.C. § 119 of: U.S. Provisional Patent Application No. 62/331,328, entitled "DISPOSABLE PULMONARY DRUG DELIVERY APPARATUS AND METHODS OF USE," filed on May 3, 2016; U.S. Provisional Patent Application No. 62/332,352, entitled "DISPOSABLE PULMONARY DRUG DELIVERY APPARATUS AND METHODS OF USE," filed on May 5, 2016; U.S. Provisional Patent Application No. 62/334,076, entitled "DISPOSABLE PULMONARY DRUG DELIVERY APPARATUS AND METHODS OF USE," filed on May 10, 2016; U.S. Provisional Patent Application No. 62/354,437, entitled "DISPOSABLE PULMONARY DRUG DELIVERY APPARATUS AND METHODS OF USE," filed on Jun. 24, 2016; U.S. Provisional Patent Application No. 62/399,091, entitled "DISPOSABLE PULMONARY DRUG DELIVERY APPARATUS AND METHODS OF USE," filed on Sep. 23, 2016; U.S. Provisional Patent Application No. 62/416,026, entitled "DISPOSABLE PULMONARY DRUG DELIVERY APPARATUS AND METHODS OF USE," filed on Nov. 1, 2016; U.S. Provisional Patent Application No. 62/422,932, entitled "DISPOSABLE PULMONARY DRUG DELIVERY APPARATUS AND METHODS OF USE," filed on Nov. 16, 2016; U.S. Provisional Patent Application No. 62/428,696, entitled "DISPOSABLE PULMONARY DRUG DELIVERY APPARATUS AND METHODS OF USE," filed on Dec. 1, 2016; U.S. Provisional Patent Application No. 62/448,796, entitled "DISPOSABLE PULMONARY DRUG DELIVERY APPARATUS AND METHODS OF USE," filed on Jan. 20, 2017; and U.S. Provisional Patent Application No. 62/471,929, entitled "DISPOSABLE PULMONARY DRUG DELIVERY APPARATUS AND METHODS OF USE," filed on Mar. 15, 2017. The content of each application is incorporated herein by reference in its entirety.

FIELD OF THE INVENTION

This disclosure relates to droplet delivery devices and more specifically to droplet delivery devices for the delivery of fluids to the pulmonary system.

BACKGROUND OF THE INVENTION

The use of aerosol generating devices for the treatment of a variety of respiratory diseases is an area of large interest.

Inhalation provides for the delivery of aerosolized drugs to treat asthma, COPD and site-specific conditions, with reduced systemic adverse effects. A major challenge is providing a device that delivers an accurate, consistent, and verifiable dose, with a droplet size that is suitable for successful delivery of medication to the targeted lung passageways.

Dose verification, delivery and inhalation of the correct dose at prescribed times is important. Getting patients to use inhalers correctly is also a major problem. A need exists to ensure that patients correctly use inhalers and that they administer the proper dose at prescribed times. Problems emerge when patients misuse or incorrectly administer a dose of their medication. Unexpected consequences occur when the patient stops taking medications, owing to not feeling any benefit, or when not seeing expected benefits or overuse the medication and increase the risk of over dosage. Physicians also face the problem of how to interpret and diagnose the prescribed treatment when the therapeutic result is not obtained.

Currently most inhaler systems such as metered dose inhalers (MDI) and pressurized metered dose inhalers (p-MDI) or pneumatic and ultrasonic-driven devices generally produce drops with high velocities and a wide range of droplet sizes including large droplet that have high momentum and kinetic energy. Droplets and aerosols with such high momentum do not reach the distal lung or lower pulmonary passageways but are deposited in the mouth and throat. As a result, larger total drug doses are required to achieve the desired deposition in targeted areas. These large doses increase the probability of unwanted side effects.

Aerosol plumes generated from current aerosol delivery systems, as a result of their high ejection velocities and the rapid expansion of the drug carrying propellant, may lead to localized cooling and subsequent condensation, deposition and crystallization of drug onto the ejector surfaces. Blockage of ejector apertures by deposited drug residue is also problematic.

This phenomenon of surface condensation is also a challenge for existing vibrating mesh or aperture plate nebulizers that are available on the market. In these systems, in order to prevent a buildup of drug onto mesh aperture surfaces, manufacturers require repeated washing and cleaning, as well as disinfection after a single use in order to prevent possible microbiological contamination. Other challenges include delivery of viscous drugs and suspensions that can clog the apertures or pores and lead to inefficiency or inaccurate drug delivery to patients or render the device inoperable. Also, the use of detergents or other cleaning or sterilizing fluids may damage the ejector mechanism or other parts of the nebulizer and lead to uncertainty as to the ability of the device to deliver a correct dose to the patient or state of performance of the device.

Accordingly, there is a need for an inhaler device that delivers particles of a suitable size range, avoids surface fluid deposition and blockage of apertures, with a dose that is verifiable, and provides feedback regarding correct and consistent usage of the inhaler to patient and professional such as physician, pharmacist or therapist.

SUMMARY OF THE INVENTION

In one aspect, the disclosure relates to a piezoelectric actuated droplet delivery device for delivering a fluid as an ejected stream of droplets to the pulmonary system of a subject. The droplet delivery device may include: a housing; a reservoir disposed within or in fluid communication with the housing for receiving a volume of fluid; an ejector mechanism in fluid communication with the reservoir, the ejector mechanism comprising a piezoelectric actuator and an aperture plate, the aperture plate having a plurality of openings formed through its thickness and the piezoelectric actuator operable to oscillate the aperture plate at a frequency to thereby generate an ejected stream of droplets, at least one differential pressure sensor positioned within the housing; the at least one differential pressure sensor configured to activate the ejector mechanism upon sensing a pre-determined pressure change within the housing to thereby generate an ejected stream of droplets; the ejector mechanism configured to generate the ejected stream of droplets wherein at least about 70% of the droplets have an average ejected droplet diameter of less than about 5 microns, such that at least about 70% of the mass of the ejected stream of droplets is delivered in a respirable range to the pulmonary system of a subject during use.

In certain aspects, the droplet delivery device further includes a surface tension plate between the aperture plate and the reservoir, wherein the surface tension plate is configured to increase contact between the volume of fluid and the aperture plate. In other aspects, the ejector mechanism and the surface tension plate are configured in parallel orientation. In yet other aspects, the surface tension plate is located within 2 mm of the aperture plate so as to create sufficient hydrostatic force to provide capillary flow between the surface tension plate and the aperture plate.

In yet other aspects, the aperture plate of the droplet delivery device comprises a domed shape. In other aspects, the aperture plate is composed of a material selected from the group consisting of poly ether ether ketone (PEEK), polyimide, polyetherimide, polyvinylidine fluoride (PVDF), ultra-high molecular weight polyethylene (UHMWPE), Ni, NiCo, Pd, Pt, NiPd, metal alloys, and combinations thereof. In other aspects, one or more of the plurality of openings of the aperture plate have different cross-sectional shapes or diameters to thereby provide ejected droplets having different average ejected droplet diameters.

In some aspects, the droplet delivery device further includes a laminar flow element located at the airflow entrance side of the housing and configured to facilitate laminar airflow across the exit side of aperture plate and to provide sufficient airflow to ensure that the ejected stream of droplets flows through the droplet delivery device during use. In other aspects, the droplet delivery device may further include a mouthpiece coupled with the housing opposite the laminar flow element.

In other aspects the ejector mechanism of the droplet delivery device is orientated with reference to the housing such that the ejected stream of droplets is directed into and through the housing at an approximate 90 degree change of trajectory prior to expulsion from the housing.

In yet other aspects, the reservoir of the droplet delivery device is removably coupled with the housing. In other aspects, the reservoir of the droplet delivery device is coupled to the ejector mechanism to form a combination reservoir/ejector mechanism module, and the combination reservoir/ejector mechanism module is removably coupled with the housing.

In other aspects, the droplet delivery device may further include a wireless communication module. In some aspects, the wireless communication module is a Bluetooth transmitter.

In yet other aspects, the droplet delivery device may further include one or more sensors selected from an infra-red transmitter, a photodetector, an additional pressure sensor, and combinations thereof.

In a further aspect, the disclosure relates to a breath actuated droplet delivery device for delivering a fluid as an ejected stream of droplets to the pulmonary system of a subject. The device may include: a housing; a combination reservoir/ejector mechanism module in fluid communication with the housing for receiving a volume of fluid and generating an ejected stream of droplets; the ejector mechanism comprising a piezoelectric actuator and an aperture plate comprising a domed shape, the aperture plate having a plurality of openings formed through its thickness and the piezoelectric actuator operable to oscillate the aperture plate at a frequency to thereby generate the ejected stream of droplets; at least one differential pressure sensor positioned within the housing; the at least one differential pressure sensor configured to activate the ejector mechanism to generate the ejected stream of droplets upon sensing a pre-determined pressure change within the housing when a subject applies an inspiratory breath to an airflow exit side of the housing; the ejector mechanism configured to generate the ejected stream of droplets wherein at least about 70% of the droplets have an average ejected droplet diameter of less than about 5 microns, such that at least about 70% of the mass of the ejected stream of droplets is delivered in a respirable range to the pulmonary system of the subject during use.

In other aspects, the domed-shape aperture plate of the breath actuated droplet delivery device is composed of a material selected from the group consisting of poly ether ether ketone (PEEK), polyimide, polyetherimide, polyvinylidine fluoride (PVDF), ultra-high molecular weight polyethylene (UHMWPE), Ni, NiCo, Pd, Pt, NiPd, metal alloys, and combinations thereof.

In other aspects, the breath actuated droplet delivery device further includes a laminar flow element located at an airflow entrance side of the housing and configured to facilitate laminar airflow across the exit side of aperture plate and to provide sufficient airflow to ensure that the ejected stream of droplets flows through the droplet delivery device during use. In yet other aspects, the breath actuated droplet delivery device further includes a mouthpiece coupled with the housing opposite the laminar flow element.

In a further aspect, this disclosure relates to a method of filtering large droplets from an aerosolized plume using inertial forces. The method may include: generating an ejected stream of droplets using a droplet delivery device, wherein the ejector mechanism is orientated with reference to the housing such that the ejected stream of droplets is directed into and through the housing at an approximate 90 degree change of trajectory prior to expulsion from the housing; and wherein droplets having a diameter greater than about 5 μm are deposited on the sidewalls of the housing due to inertial forces, without being carried in entrained airflow through and out of the droplet delivery device to the pulmonary system of the subject.

In another aspect, the disclosure relates to a method for generating and delivering a fluid as an ejected stream of droplets to the pulmonary system of a subject in a respirable range. The method may comprise: (a) generating an ejected stream of droplets via a piezoelectric actuated droplet delivery device, wherein at least about 70% of the ejected stream of droplets have an average ejected droplet diameter of less than about 5 μm; and (b) delivering the ejected stream of droplets to the pulmonary system of the subject such that at least about 70% of the mass of the ejected stream of droplets is delivered in a respirable range to the pulmonary system of a subject during use.

In other aspects, the ejected stream of droplets of the disclosed method are subjected to an approximate 90 degree change of trajectory within the piezoelectric actuated droplet delivery device such that droplets having a diameter greater than about 5 μm are filtered from the ejected stream of droplets due to inertial forces, without being carried in entrained airflow through and out of the piezoelectric actuated droplet delivery device to the pulmonary system of the subject. In yet other aspects, the filtering of droplets having a diameter greater than about 5 μm increases the mass of the ejected stream of droplets delivered to the pulmonary system of the subject during use. In other aspects, the ejected stream of droplets may further comprise droplets having an average ejected droplet diameter of between about 5 μm to about 10 μm. In further aspects, the ejected stream of droplets may comprise a therapeutic agent for the treatment of a pulmonary disease, disorder, or condition.

In further aspects, the piezoelectric actuated droplet delivery device may comprise: a housing; a reservoir disposed within or in fluid communication with the housing for receiving a volume of fluid; an ejector mechanism in fluid communication with the reservoir, the ejector mechanism comprising a piezoelectric actuator and an aperture plate, the aperture plate having a plurality of openings formed through its thickness and the piezoelectric actuator operable to oscillate the aperture plate at a frequency to thereby generate an ejected stream of droplets; and at least one differential pressure sensor positioned within the housing, the at least one differential pressure sensor configured to activate the ejector mechanism upon sensing a pre-determined pressure change within the housing to thereby generate an ejected stream of droplets.

In yet further aspects, the aperture plate of the piezoelectric actuated droplet delivery device comprises a domed shape. In other aspects, the piezoelectric actuated droplet delivery device further comprises a laminar flow element located at the airflow entrance side of the housing and configured to facilitate laminar airflow across the exit side of aperture plate and to provide sufficient airflow to ensure that the ejected stream of droplets flows through the droplet delivery device during use.

BRIEF DESCRIPTION OF THE DRAWINGS

The invention will be more clearly understood from the following description given by way of example, in which:

Referring to FIG. 1B and FIG. 1C, illustrate exemplary location of the pressure sensors and restrictions. FIG. 1B is an example where the restriction is internal to the mouthpiece tube. FIG. 1C, is an example where the restriction is located at the laminar flow element and the pressure is sensed as the differential between the interior of the mouthpiece tube and the pressure outside the tube. FIG. 1D is a screen capture of the delta P sensor response to an inhaled breath of a ~1 second duration. FIG. 1E, FIG. 1F, and FIG. 1G depict the delta P sensor design and its assembly onto a device board (FIG. 1E). The sensor has pneumatic connection through the hole in the printed circuit board (PCB) and may be mounted either on the main PCB as shown on schemes (FIG. 1F) or on a daughter board on scheme (FIG. 1G).

FIG. 3B is an enlarged view of an ejector mechanism of the device of FIG. 3A, and FIG. 3C is an enlargement of a surface tension plate of the device of FIG. 3A, in accordance with an embodiment of the disclosure.

FIGS. 4A-4E illustrate an embodiment of a combination reservoir/ejector mechanism module., FIG. 4A shows an exploded view, FIG. 4B shows a top view, FIG. 4C shows a cross sectional view, and FIG. 4D shows an enlarged view of a portion of a module and mechanism for mechanical mounting of the ejector mechanism to the reservoir, in accordance with an embodiment of the disclosure. FIG. 4E shows a side view of an exemplary superhydrophobic filter and micron-sized aperture for restricting evaporation, in accordance with an embodiment of the disclosure.

FIGS. 5A-5G provide an exemplary ejector closure mechanism, in accordance with an embodiment of the disclosure. FIG. 5A illustrates the ejector closure mechanism in an open position, and FIG. 5B illustrates the ejector closure mechanism in a closed position. FIG. 5C-5E illustrate detailed views of an exemplary ejector closure mechanism in accordance with an embodiment of the disclosure, including a top cover in FIG. 5C, and a motor in stages of actuation in FIGS. 5D-5E. FIGS. 5F-5G provide an exploded view of an exemplary ejector closure mechanism in accordance with an embodiment of the disclosure.

FIGS. 7A-7B depict exemplary ejector mechanism designs, in accordance with embodiments of the disclosure.

FIG. 9 depicts an aperture plate opening design, in accordance with embodiments of the disclosure.

In FIG. 12A, d is the active area diameter and h is the aperture plate dome height. FIG. 12B shows a plot of the calculation of dome height, and aperture plate height versus active area.

DETAILED DESCRIPTION

Figure 1A:
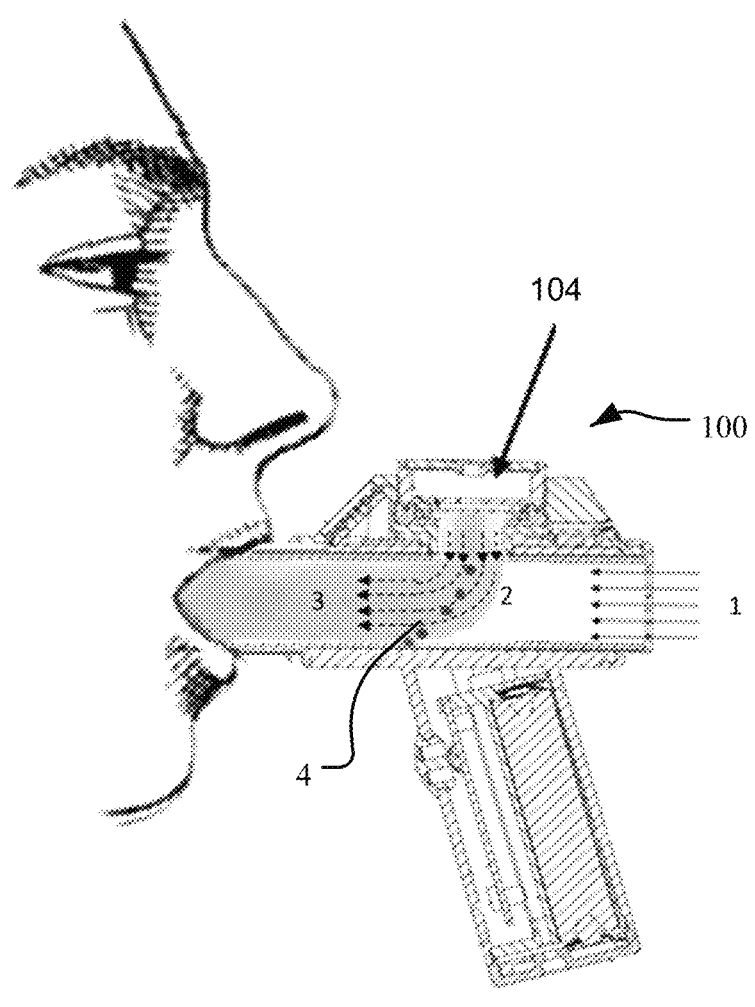
FIG. 1A is a diagram displaying automatic breath actuation and inertial filtering using a droplet delivery device in accordance with an embodiment of the disclosure.

Effective delivery of medication to the deep pulmonary regions of the lungs through the alveoli, has always posed a problem, especially to children and elderly, as well as to those with the diseased state, owing to their limited lung capacity and constriction of the breathing passageways. The impact of constricted lung passageways limits deep inspiration and synchronization of the administered dose with the inspiration/expiration cycle. For optimum deposition in alveolar airways, particles with aerodynamic diameters in the ranges of 1 to 5 μm are optimal, with particles below about 4 μm shown to reach the alveolar region of the lungs, while larger particles are deposited on the tongue or strike the throat and coat the bronchial passages. Smaller particles, for example less than about 1 μm that penetrate more deeply into the lungs have a tendency to be exhaled.

In certain aspects, the present disclosure relates to a droplet delivery device for delivery a fluid as an ejected stream of droplets to the pulmonary system of a subject and related methods of delivering safe, suitable, and repeatable dosages to the pulmonary system of a subject. The present disclosure also includes a droplet delivery device and system capable of delivering a defined volume of fluid in the form of an ejected stream of droplets such that an adequate and repeatable high percentage of the droplets are delivered into the desired location within the airways, e.g., the alveolar airways of the subject during use.

The present disclosure provides a droplet delivery device for delivery of a fluid as an ejected stream of droplets to the pulmonary system of a subject, the device comprising a housing, a reservoir for receiving a volume of fluid, and an ejector mechanism including a piezoelectric actuator and an aperture plate, wherein the ejector mechanism is configured to eject a stream of droplets having an average ejected droplet diameter of less than 5 microns. In specific embodiments, the ejector mechanism is activated by at least one differential pressure sensor located within the housing of the droplet delivery device upon sensing a pre-determined pressure change within the housing. In certain embodiments, such a pre-determined pressure change may be sensed during an inspiration cycle by a user of the device, as will be explained in further detail herein.

In accordance with certain aspects of the disclosure, effective deposition into the lungs generally requires droplets less than 5 μm in diameter. Without intending to be limited by theory, to deliver fluid to the lungs a droplet delivery device must impart a momentum that is sufficiently high to permit ejection out of the device, but sufficiently low to prevent deposition on the tongue or in the back of the throat. Droplets below 5 μm in diameter are transported almost completely by motion of the airstream and entrained air that carry them and not by their own momentum.

In certain aspects, the present disclosure includes and provides an ejector mechanism configured to eject a stream of droplets within the respirable range of less than 5 μm. The ejector mechanism is comprised of an aperture plate that is directly or indirectly coupled to a piezoelectric actuator. In certain implementations, the aperture plate may be coupled to an actuator plate that is coupled to the piezoelectric actuator. The aperture plate generally includes a plurality of openings formed through its thickness and the piezoelectric actuator directly or indirectly (e.g. via an actuator plate) oscillates the aperture plate, having fluid in contact with one surface of the aperture plate, at a frequency and voltage to generate a directed aerosol stream of droplets through the openings of the aperture plate into the lungs, as the patient inhales. In other implementations where the aperture plate is coupled to the actuator plate, the actuator plate is oscillated by the piezoelectric oscillator at a frequency and voltage to generate a directed aerosol stream or plume of aerosol droplets.

In certain aspects, the present disclosure relates to a droplet delivery device for delivering a fluid as an ejected stream of droplets to the pulmonary system of a subject. In certain aspects, the therapeutic agents may be delivered at a high dose concentration and efficacy, as compared to alternative dosing routes and standard inhalation technologies.

In certain embodiments, the droplet delivery devices of the disclosure may be used to treat various diseases, disorders and conditions by delivering therapeutic agents to the pulmonary system of a subject. In this regard, the droplet delivery devices may be used to deliver therapeutic agents both locally to the pulmonary system, and systemically to the body.

More specifically, the droplet delivery device may be used to deliver therapeutic agents as an ejected stream of droplets to the pulmonary system of a subject for the treatment or prevention of pulmonary diseases or disorders such as asthma, chronic obstructive pulmonary diseases (COPD) cystic fibrosis (CF), tuberculosis, chronic bronchitis, or pneumonia. In certain embodiments, the droplet delivery device may be used to deliver therapeutic agents such as COPD medications, asthma medications, or antibiotics. By way of non-limiting example, such therapeutic agents include albuterol sulfate, ipratropium bromide, tobramycin, and combinations thereof.

In other embodiments, the droplet delivery device may be used for the systemic delivery of therapeutic agents including small molecules, therapeutic peptides, proteins, antibodies, and other bioengineered molecules via the pulmonary system. By way of non-limiting example, the droplet delivery device may be used to systemically deliver therapeutic agents for the treatment or prevention of indications inducing, e.g., diabetes mellitus, rheumatoid arthritis, plaque psoriasis, Crohn's disease, hormone replacement, neutropenia, nausea, influenza, etc.

By way of non-limiting example, therapeutic peptides, proteins, antibodies, and other bioengineered molecules include: growth factors, insulin, vaccines (Prevnor-Pneumonia, Gardasil-HPV), antibodies (Avastin, Humira, Remicade, Herceptin), Fc Fusion Proteins (Enbrel, Orencia), hormones (Elonva-long acting FSH, Growth Hormone), enzymes (Pulmozyme-rHu-DNAase-), other proteins (Clotting factors, Interleukins, Albumin), gene therapy and RNAi, cell therapy (Provenge-Prostate cancer vaccine), antibody drug conjugates-Adcetris (Brentuximab vedotin for HL), cytokines, anti-infective agents, polynucleotides, oligo-nucleotides (e.g., gene vectors), or any combination thereof; or solid particles or suspensions such as Flonase (fluticasone propionate) or Advair (fluticasone propionate and salmeterol xinafoate).

In other embodiments, the droplet delivery device of the disclosure may be used to deliver a solution of nicotine including the water-nicotine azeotrope for the delivery of highly controlled dosages for smoking cessation or a condition requiring medical or veterinary treatment. In addition, the fluid may contain THC, CBD, or other chemicals contained in marijuana for the treatment of seizures and other conditions.

In certain embodiments, the drug delivery device of the disclosure may be used to deliver scheduled and controlled substances such as narcotics for the highly controlled dispense of pain medications where dosing is only enabled by doctor or pharmacy communication to the device, and where dosing may only be enabled in a specific location such as the patient's residence as verified by GPS location on the patient's smart phone. This mechanism of highly controlled dispensing of controlled medications can prevent the abuse or overdose of narcotics or other addictive drugs.

Certain benefits of the pulmonary route for delivery of drugs and other medications include a non-invasive, needle-free delivery system that is suitable for delivery of a wide range of substances from small molecules to very large proteins, reduced level of metabolizing enzymes compared to the GI tract and absorbed molecules do not undergo a first pass effect. (A. Tronde, et al., *J Pharm Sci,* 92 (2003) 1216-1233; A. L. Adjei, et al., Inhalation Delivery of Therapeutic Peptides and Proteins, M. Dekker, New York, 1997). Further, medications that are administered orally or intravenously are diluted through the body, while medications given directly into the lungs may provide concentrations at the target site (the lungs) that are about 100 times higher than the same intravenous dose. This is especially important for treatment of drug resistant bacteria, drug resistant tuberculosis, for example and to address drug resistant bacterial infections that are an increasing problem in the ICU.

Another benefit for giving medication directly into the lungs is that high, toxic levels of medications in the blood stream their associated side effects can be minimized. For example, intravenous administration of tobramycin leads to very high serum levels that are toxic to the kidneys and therefore limits its use, while administration by inhalation significantly improves pulmonary function without severe side effects to kidney functions. (Ramsey et al., Intermittent administration of inhaled tobramycin in patients with cystic fibrosis. *N Engl J Med* 1999; 340:23-30; MacLusky et al., Long-term effects of inhaled tobramycin in patients with cystic fibrosis colonized with Pseudomonas aeruginosa. *Pediatr Pulmonol* 1989; 7:42-48; Geller et al., Pharmacokinetics and bioavailability of aerosolized tobramycin in cystic fibrosis. Chest 2002; 122:219-226.)

As discussed above, effective delivery of droplets deep into the lung airways require droplets that are less than 5 microns in diameter, specifically droplets with mass mean aerodynamic diameters (MMAD) that are less than 5 microns. The mass mean aerodynamic diameter is defined as the diameter at which 50% of the particles by mass are larger and 50% are smaller. In certain aspects of the disclosure, in order to deposit in the alveolar airways, droplet particles in this size range must have momentum that is sufficiently high to permit ejection out of the device, but sufficiently low to overcome deposition onto the tongue (soft palate) or pharynx.

In other aspects of the disclosure, methods for generating an ejected stream of droplets for delivery to the pulmonary system of user using the droplet delivery devices of the disclosure are provided. In certain embodiments, the ejected stream of droplets is generated in a controllable and defined droplet size range. By way of example, the droplet size range includes at least about 50%, at least about 60%, at least about 70%, at least about 85%, at least about 90%, between about 50% and about 90%, between about 60% and about 90%, between about 70% and about 90%, etc., of the ejected droplets are in the respirable range of below about 5 µm.

In other embodiments, the ejected stream of droplets may have one or more diameters, such that droplets having multiple diameters are generated so as to target multiple regions in the airways (mouth, tongue, throat, upper airways, lower airways, deep lung, etc.) By way of example, droplet diameters may range from about 1 µm to about 200 µm, about 2 µm to about 100 µm, about 2 µm to about 60 µm, about 2 µm to about 40 µm, about 2 µm to about 20 µm, about 1 µm to about 5 µm, about 1 µm to about 4.7 µm, about 1 µm to about 4 µm, about 10 µm to about 40 µm, about 10 µm to about 20 µm, about 5 µm to about 10 µm, and combinations thereof. In particular embodiments, at least a fraction of the droplets have diameters in the respirable range, while other particles may have diameters in other sizes so as to target non-respirable locations (e.g., larger than 5 µm). Illustrative ejected droplet streams in this regard might have 50%-70% of droplets in the respirable range (less than about 5 µm), and 30%-50% outside of the respirable range (about 5 µm-about 10 µm, about 5 µm-about 20 µm, etc.)

In another embodiment, methods for delivering safe, suitable, and repeatable dosages of a medicament to the pulmonary system using the droplet delivery devices of the disclosure are provided. The methods deliver an ejected stream of droplets to the desired location within the pulmonary system of the subject, including the deep lungs and alveolar airways.

In certain aspects of the disclosure, a droplet delivery device for delivery an ejected stream of droplets to the pulmonary system of a subject is provided. The droplet delivery device generally includes a housing and a reservoir disposed in or in fluid communication with the housing, an ejector mechanism in fluid communication with the reservoir, and at least one differential pressure sensor positioned within the housing. The differential pressure sensor is configured to activate the ejector mechanism upon sensing a pre-determined pressure change within the housing, and the ejector mechanism is configured to generate a controllable plume of an ejected stream of droplets. The ejected stream of droplets includes, without limitation, solutions, suspensions or emulsions which have viscosities in a range capable of droplet formation using the ejector mechanism. The ejector mechanism may include a piezoelectric actuator which is directly or indirectly coupled to an aperture plate having a plurality of openings formed through its thickness. The piezoelectric actuator is operable to directly or indirectly oscillate the aperture plate at a frequency to thereby generate an ejected stream of droplets.

In certain embodiments, the droplet delivery device may include a combination reservoir/ejector mechanism module that may be replaceable or disposable either on a periodic basis, e.g., a daily, weekly, monthly, as-needed, etc. basis, as may be suitable for a prescription or over-the-counter medication. The reservoir may be prefilled and stored in a pharmacy for dispensing to patients or filled at the pharmacy or elsewhere by using a suitable injection means such as a hollow injection syringe driven manually or driven by a micro-pump. The syringe may fill the reservoir by pumping fluid into or out of a rigid container or other collapsible or non-collapsible reservoir. In certain aspects, such disposable/replaceable, combination reservoir/ejector mechanism module may minimize and prevent buildup of surface deposits or surface microbial contamination on the aperture plate, owing to its short in-use time.

The present disclosure also provides a droplet delivery device that is altitude insensitive. In certain implementations, the droplet delivery device is configured so as to be insensitive to pressure differentials that may occur when the user travels from sea level to sub-sea levels and at high altitudes, e.g., while traveling in an airplane where pressure differentials may be as great as 4 psi. As will be discussed in further detail herein, in certain implementations of the disclosure, the droplet delivery device may include a super-hydrophobic filter which provides for free exchange of air across the filter into and out of the reservoir, while blocking moisture or fluids from passing through the filter, thereby reducing or preventing fluid leakage or deposition on aperture plate surfaces.

Reference will now be made to the figures, with like components illustrates with like references numbers.

Referring to FIG. 1A, in one aspect of the disclosure, a droplet delivery device 100 is illustrated in use by a patient. Droplet delivery device 100 may include one or more differential pressure sensors (not shown) to provide for automatic electronic breath actuation of the device. Such pressure sensor(s) automatically detects a desired point during a user's inhalation cycle to activate the actuation of ejector mechanism 104 to generate an ejected stream of droplets. For instance, a user may begin to inhale, pulling air through the back of the device at 1, triggering the differential pressure sensor and thereby activating actuation of ejector mechanism 104 to generate an ejected stream of droplets at 2, which stream of droplets are entrained in the user's inhalation airflow thereby traveling along the device and into the user's airway at 3. As will be explained in further detail herein, any large droplets are removed from the entrained airflow via inertial filtering, falling to the bottom surface of the device at 4. By way of non-limiting example, the pressure sensor(s) may be programmed to trigger a 2 second ejection when the user generated airflow within the device is about 10 SLM or similar pressure. However, any suitable differential pressure within a standard physiological range of a target user may be used. Such a trigger point during the inspiratory cycle may provide an optimum point during a user's inhalation cycle to activate and actuate the generation of an ejected stream of droplets, and delivery of medication. Since electronic breath actuation does not require user-device coordination, the droplet delivery devices and methods of the disclosure further provide assurance for optimum delivery of inhaled medication.

Figures 1B, 1C, 1D, 1E, 1F, 1G:
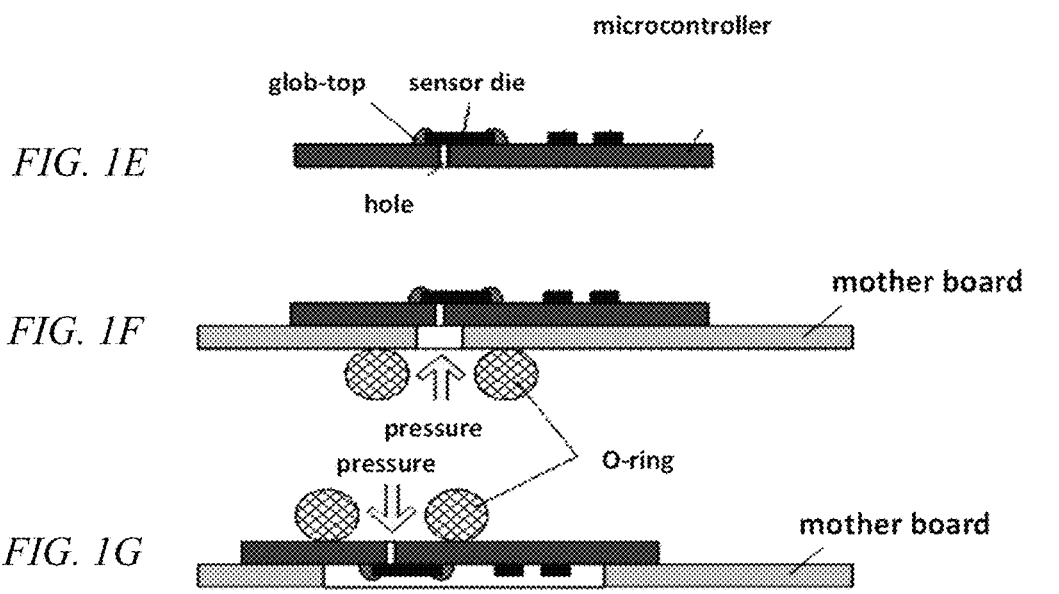
FIGS. 1B-1G illustrates an example of an inhalation detection system that senses airflow by detecting pressure differentials across flow restriction.

By way of non-limiting example, FIGS. 1B-1G illustrate inhalation detection systems according to embodiments of the disclosure that sense airflow by detecting pressure differentials across a flow restriction. As will be discussed in further detail below with reference to FIGS. 2A, 2C, and 3A, pressure sensors may be located within the droplet delivery device of the disclosure with a restriction that is internal to the device, e.g., within aerosol delivery mouthpiece tube. For instance, FIG. 1B is an example where the restriction is internal to the device tube, and FIG. 1C, the restriction is at the air inlet laminar flow element. The pressure is sensed as the differential between the interior of the device tube and the pressure outside the tube. FIG. 1D is a screen capture of an exemplary pressure sensor response to an inhaled breath of a ~1 second duration. FIG. 1E, FIG. 1F, and FIG. 1G illustrate exemplary differential pressure sensor designs and assemblies onto a device board (FIG. 1E). The sensor may have pneumatic connection through the hole in the printed circuit board (PCB) and may be mounted either on the main PCB, as shown below on scheme (FIG. 1F), or on a daughter board as shown on scheme (FIG. 1G).

Once activated, the droplet delivery device of the disclosure may be actuated to delivery an ejected stream of droplets for any suitable time sufficient to deliver the desired dosage. For instance, the piezoelectric actuator may be activated to the oscillate the aperture plate to thereby generate the ejected stream of droplets for a short burst of time, e.g., one tenth of a second, or for sever seconds, e.g., 5 second. In certain embodiments, the droplet delivery device may be activated to generate and deliver the ejected stream of droplets, e.g., for up to about 5 seconds, up to about 4 seconds, up to about 3 seconds, up to about 2 seconds, up to about 1 second, between about 1 second and about 2 seconds, between about 0.5 seconds and 2 seconds, etc.

In certain embodiments, any suitable differential pressure sensor with adequate sensitivity to measure pressure changes obtained during standard inhalation cycles may be used, e.g., ±5 SLM, 10 SLM, 20 SLM, etc. For instance, pressure sensors from Sensirion, Inc., SDP31 or SDP32 (U.S. Pat. No. 7,490,511 B2) are particularly well suited for these applications.

In certain embodiments of the present disclosure, the signal generated by the pressure sensors provides a trigger for activation and actuation of the ejector mechanism of the droplet delivery device at or during a peak period of a patient's inhalation (inspiratory) cycle and assures optimum deposition of the ejected stream of droplets and delivery of the medication into the pulmonary airways of the user.

In addition, an image capture device, including cameras, scanners, or other sensors without limitation, e.g. charge coupled device (CCD), may be provided to detect and measure the ejected aerosol plume. These detectors, LED, delta P transducer, CCD device, all provide controlling signals to a microprocessor or controller in the device used for monitoring, sensing, measuring and controlling the ejection of fluid and reporting patient compliance, treatment times, dosage, and patient usage history, etc., via Bluetooth, for example.

In certain aspects of the disclosure, the ejector mechanism, reservoir, and housing/mouthpiece function to generate a plume or aerosol of fluid with droplet diameters less than 5 um. As discussed above, in certain embodiments, the reservoir and ejector mechanism are integrated to form a combination reservoir/ejector mechanism module which comprises the piezoelectric actuator powered by electronics in the device housing and a drug reservoir which may carry sufficient fluid for just a few or several hundred doses of medicament.

In certain embodiments, as illustrated herein, the combination module may have a pressure equalization port or filter to minimize leakage during atmospheric pressure changes such as on a commercial airliner. The combination module may also include components that may carry information read by the housing electronics including key parameters such as actuator frequency and duration, drug identification, and information pertaining to patient dosing intervals. Some information may be added to the module at the factory, and some may be added at the pharmacy. In certain embodiments, information placed by the factory may be protected from modification by the pharmacy. The module information may be carried as a printed barcode or physical barcode encoded into the module geometry (such as light transmitting holes on a flange which are read by sensors on the housing). Information may also be carried by a programmable or non-programmable microchip on the module which communicates to the electronics in the housing via the piezoelectric power connection. For example, each time the device is turned on, the cartridge may be sent minimal voltage, e.g., five volts through the piezoelectric power connection which causes the data chip to send a low-level pulse stream back to the electronics via the same power connection.

By way of example, module programming at the factory or pharmacy may include a drug code which may be read by the device, communicated via Bluetooth to an associated user smartphone and then verified as correct for the user. In the event a user inserts an incorrect, generic, damaged, etc., module into the device, the smartphone might be prompted to lock out operation of the device, thus providing a measure of user safety and security not possible with passive inhaler devices. In other embodiments, the device electronics can restrict use to a limited time period (perhaps a day, or weeks or months) to avoid issues related to drug aging or the gradual buildup of contamination on the aperture plate.

An airflow sensor located in the device aerosol delivery tube measures the inspiratory and expiratory flow rates flowing in and out of the mouthpiece. This sensor is placed so that it does not interfere with drug delivery or become a site for collection of residue or promote bacterial growth or contamination. A differential (or gage) pressure sensor downstream of a flow restrictor (e.g., laminar flow element) measures airflow based upon the pressure differential between the inside of the mouthpiece relative to the outside air pressure. During inhalation (inspiratory flow) the mouthpiece pressure will be lower than the ambient pressure and during exhalation (expiratory flow) the mouthpiece pressure will be greater than the ambient pressure. The magnitude of the pressure differential during an inspiratory cycle is a measure of the magnitude of airflow and airway resistance at the air inlet end of the aerosol delivery tube.

Figure 2B:
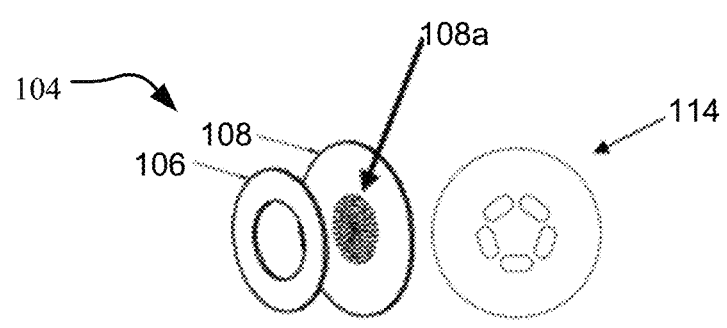
FIG. 2B is an enlargement of an ejector mechanism in accordance with an embodiment of FIG. 2A.
Figure 2A:
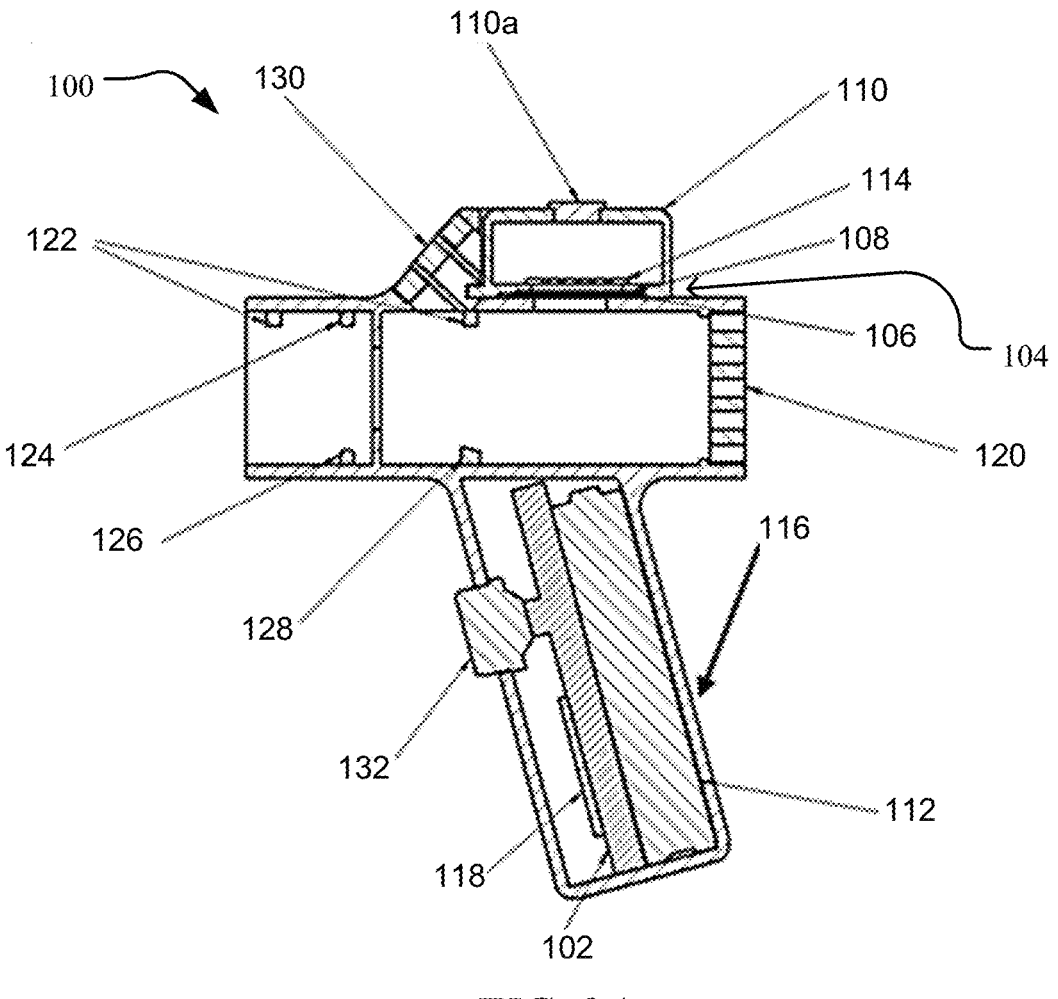
FIG. 2A is a cross sectional view of a droplet delivery device in accordance with an embodiment of the disclosure.

In one embodiment, referring to FIG. 2A, an exemplary droplet delivery device 100 is illustrated including an power/activation button 132; an electronics circuit board 102; an ejector mechanism 104 including a piezoelectric actuator 106 and an aperture plate 108; a reservoir 110, which may include an optional filter 110a on a surface thereof; and a power source 112 (which may optionally be rechargeable) electronically coupled to the piezoelectric actuator 106. In certain embodiments, the reservoir 110 may be coupled to or integrated with the ejector mechanism 104 to form a combination drug reservoir/ejector mechanism module (see FIG. 4A-4E) that may be replaceable, disposable or reusable. Droplet delivery device 100 further includes power source 112, which when activated, e.g., by pressure sensor 122 upon sensing a pre-determined change in pressure within the device, will energize the piezoelectric actuator 106 to vibrate the aperture plate 108 to cause an ejected stream of droplets to be ejected through the aperture plate 108 in a predefined direction. Droplet delivery device 100 may further include surface tension plate 114 to, at least in part, direct and focus fluid to the aperture plate 108, as described further herein.

The components may be packaged in a housing 116, which may be disposable or reusable. The housing 116 may be handheld and may be adapted for communication with other devices via a Bluetooth communication module 118 or similar wireless communication module, e.g., for communication with a subject's smart phone, tablet or smart device (not shown). In one embodiment, laminar flow element 120 may be located at the air entry side of the housing 116 to facilitate laminar airflow across the exit side of aperture plate 108 and to provide sufficient airflow to ensure that the ejected stream of droplets flow through the device during use. Aspects of the present embodiment further allows customizing the internal pressure resistance of the droplet delivery device by allowing the placement of laminar flow elements having openings of different sizes and varying configurations to selectively increase or decrease internal pressure resistance, as will be explained in further detail herein.

Droplet delivery device 100 may further include various sensors and detectors 122, 124, 126, and 128 to facilitate device activation, spray verification, patient compliance, diagnostic mechanisms, or as part of a larger network for data storage, big data analytics and for interacting and interconnected devices used for subject care and treatment, as described further herein. Further, housing 116 may include an LED assembly 130 on a surface thereof to indicate various status notifications, e.g., ON/READY, ERROR, etc.

Referring more specifically to FIG. 2B, an enlargement of ejector mechanism 104 in accordance with an embodiment of the disclosure is illustrated. The ejector mechanism 104 may generally include a piezoelectric actuator 106, an aperture plate 108, which includes a plurality of openings 108a formed through its thickness. A surface tension plate 114 may also be positioned on the fluid facing surface of the aperture plate, as described in more detail herein. The piezoelectric actuator 106 is operable to oscillate, e.g., at its resonant frequency, the aperture plate 108 to thereby generate an ejected stream of droplets through the plurality of openings 108a. In certain embodiments, openings 108a and ejector mechanism 104 may be configured to generate an ejected stream of droplets having a MMAD of 5 µm or less.

The airflow exit of housing 116 of the droplet delivery device 100 of FIG. 2A through which the ejected stream of droplets exit as they are inhaled into a subject's airways, may be configured and have, without limitation, a cross sectional shape of a circle, oval, rectangular, hexagonal or other shape, while the shape of the length of the tube, again without limitation, may be straight, curved or have a Venturi-type shape.

In another embodiment (not shown), a mini fan or centrifugal blower may be located at the air inlet side of the laminar flow element 120 or internally of the housing 116 within the airstream. The mini fan generally may provide additional airflow and pressure to the output of the airstream. For patients with low pulmonary output, this additional airstream may ensure that the ejected stream of droplets is pushed through the device into the patient's airway. In certain implementations, this additional source of airflow ensures that the ejector face is swept clean of the ejected droplets and also provides mechanism for spreading the droplet plume into an airflow which creates greater separation between droplets. The airflow provided by the mini fan may also act as a carrier gas, ensuring adequate dose dilution and delivery.

Figure 2C:
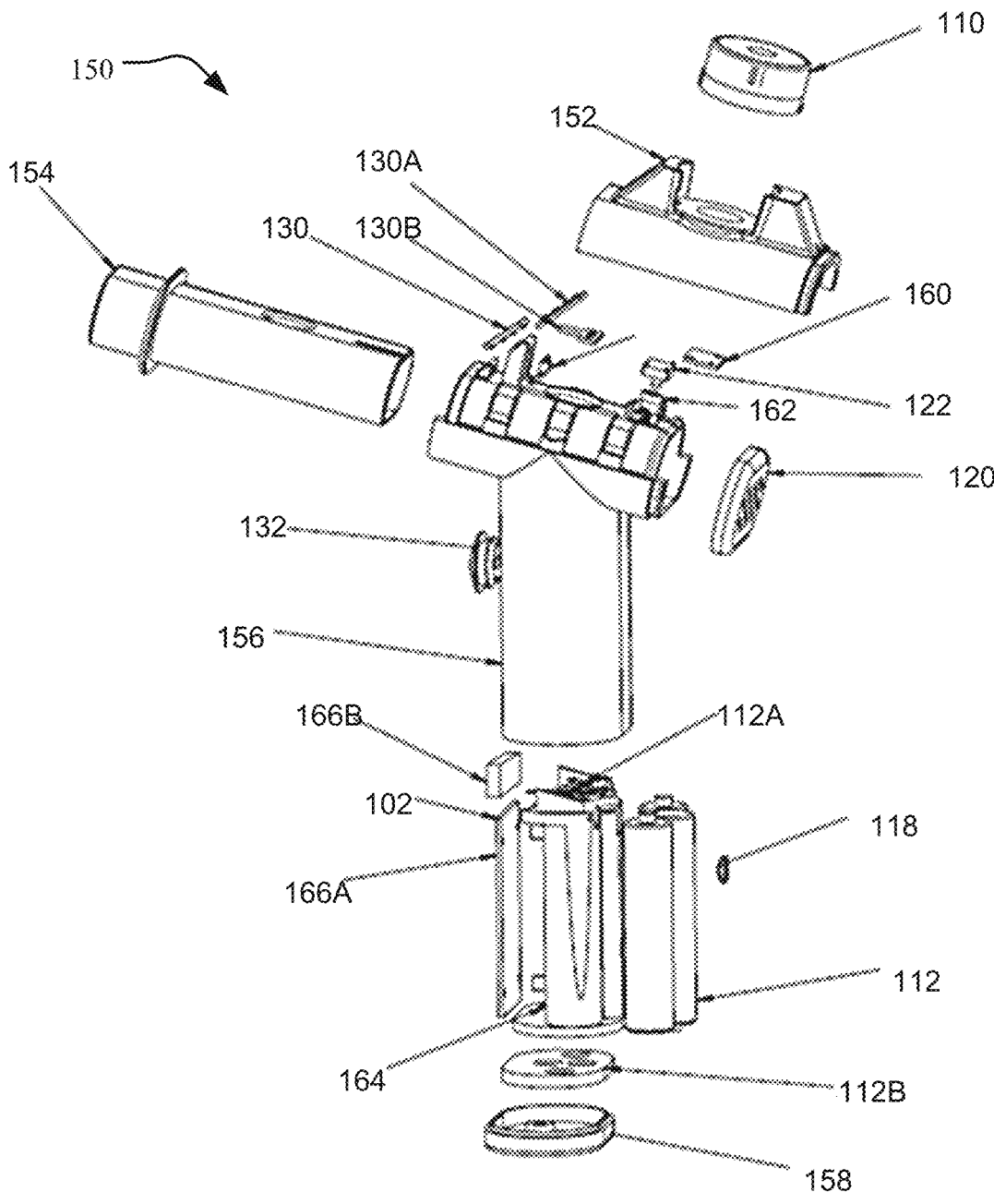
FIG. 2C is an exploded view of the droplet delivery device.

With reference to FIG. 2C, another implementation of a droplet delivery device of the disclosure is illustrated in an exploded view. Again, like components are indicated with like reference numbers. Droplet delivery device 150 is illustrated with a top cover 152, which provides a cover for the aerosol delivery mouthpiece tube 154 and interfaces with reservoir 110, a base handle 156, an activation button 132, and bottom cover for the handle 158.

A series of colored lights powered by an LED assembly are located in the front region of the ejector device. In this embodiment, the LED assembly 130, including, e.g., four LED's, 130A, and an electronics board 130B, on which the LED assembly 130 is mounted and provides an electrical connection to the main electronics board 102. The LED assembly 130 may provide the user with immediate feedback on functions such as, power, ON and OFF, to signal when breath activation occurs (as described further herein), to provide the user with feedback as to when an effective or ineffective dispense of a dose is delivered (as described further herein), or to provide other user feedback to maximize patient compliance.

The laminar flow element 120 is located opposite the patient use end of the mouthpiece tube 154, and a differential pressure sensor 122, pressure sensor electronics board 160, and pressure sensor O-ring 162 are located nearby.

The remaining components detailed in FIG. 2C are located in the device handle 156, which include the mount assembly 164 for power source 112 (e.g., three, AAA batteries), top and bottom battery contacts, 112A, 112B, and audio chip and speaker, 166A, 166B.

Again, with reference to FIG. 2C, a Bluetooth communication module 118 or similar wireless communication module is provided in order to link the droplet delivery device 150 to a smartphone or other similar smart devices (not shown). Bluetooth connectivity facilitates implementation of various software or App's which may provide and facilitate patient training on the use of the device. A major obstacle to effective inhaler drug therapy has been either poor patient adherence to prescribed aerosol therapy or errors in the use of an inhaler device. By providing a real time display on the smartphone screen of a plot of the patient's inspiratory cycle, (flow rate versus time) and total volume, the patient may be challenged to reach a goal of total inspiratory volume that was previously established and recorded on the smartphone during a training session in a doctor's office. Bluetooth connectivity further facilitates patient adherence to prescribed drug therapy and promotes compliance by providing a means of storing and archiving compliance information, or diagnostic data (either on the smartphone or cloud or other large network of data storage) that may be used for patient care and treatment.

Figure 2D:
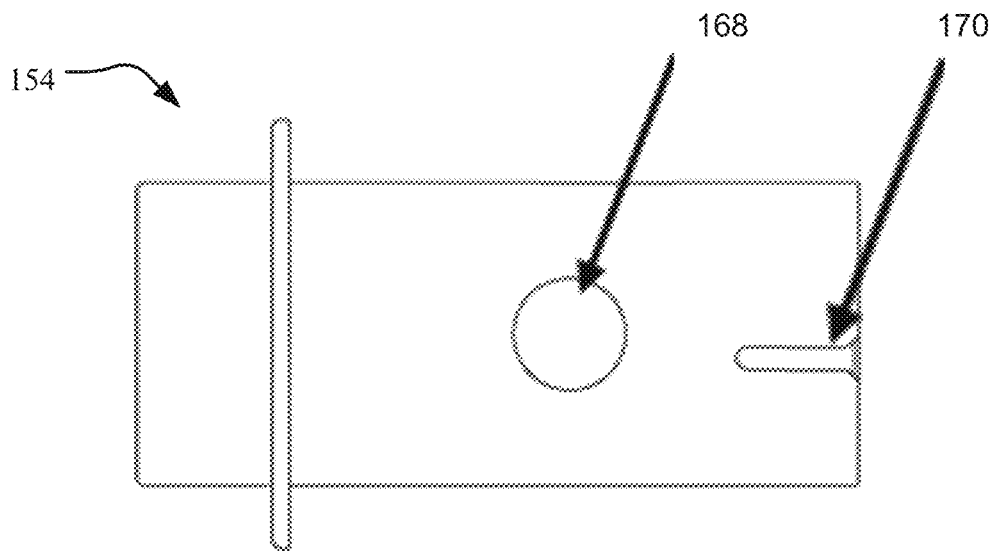
FIG. 2D is a topview of a mouthpiece tube, in accordance with an embodiment of the disclosure.

The aerosol delivery mouthpiece tube may be removable, replaceable and sterilizable. This feature improves sanitation for drug delivery by providing means and ways to minimize buildup of aerosolized medication within the mouthpiece tube by providing ease of replacement, disinfection and washing. In one embodiment, the mouthpiece tube may be formed using sterilizable and transparent polymer compositions such as polycarbonate, polyethylene or polypropylene, and not limited by example. With reference to FIG. 2D, a topview of an exemplary aerosol delivery mouthpiece tube 154 is illustrated, which includes a circular port 168 through which the aerosol spray passes from the ejector mechanism (not shown), as well as the location of a slot 170 that accommodates the pressure sensor (not shown). Materials selection for the aerosol delivery mouthpiece tube should generally allow effective cleaning and have electrostatic properties that do not interfere with or trap fluid droplets of interest. Unlike many spray devices with larger droplets and higher dispense velocities, the mouthpiece of the disclosure does not need to be long or specially shaped to reduce the speed of large droplets that would otherwise impact the back of the patients mouth and throat.

Figure 2E:
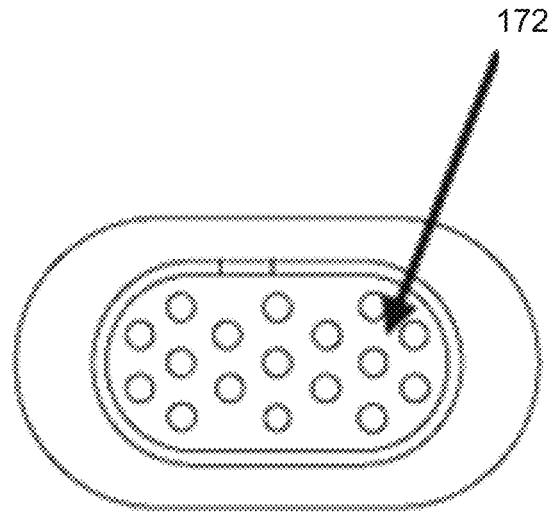
FIG. 2E is a front view of a mouthpiece tube with an air aperture grid or opening, in accordance with an embodiment of the disclosure.

In other embodiments, the internal pressure resistance of the droplet delivery device may be customized to an individual user or user group by modifying the mouthpiece tube design to include various configurations of air aperture grids or openings, thereby increasing or decreasing resistance to airflow through the device as the user inhales. For instance, with reference to FIG. 2E, an exemplary aperture grid 172 at the mouthpiece tube opening is illustrated. However, different air entrance aperture sizes and numbers may be used to achieve different resistance values, and thereby different internal device pressure values. This feature provides a mechanism to easily and quickly adapt and customize the airway resistance of the droplet delivery device to the individual patient's state of health or condition.

Figure 3A:
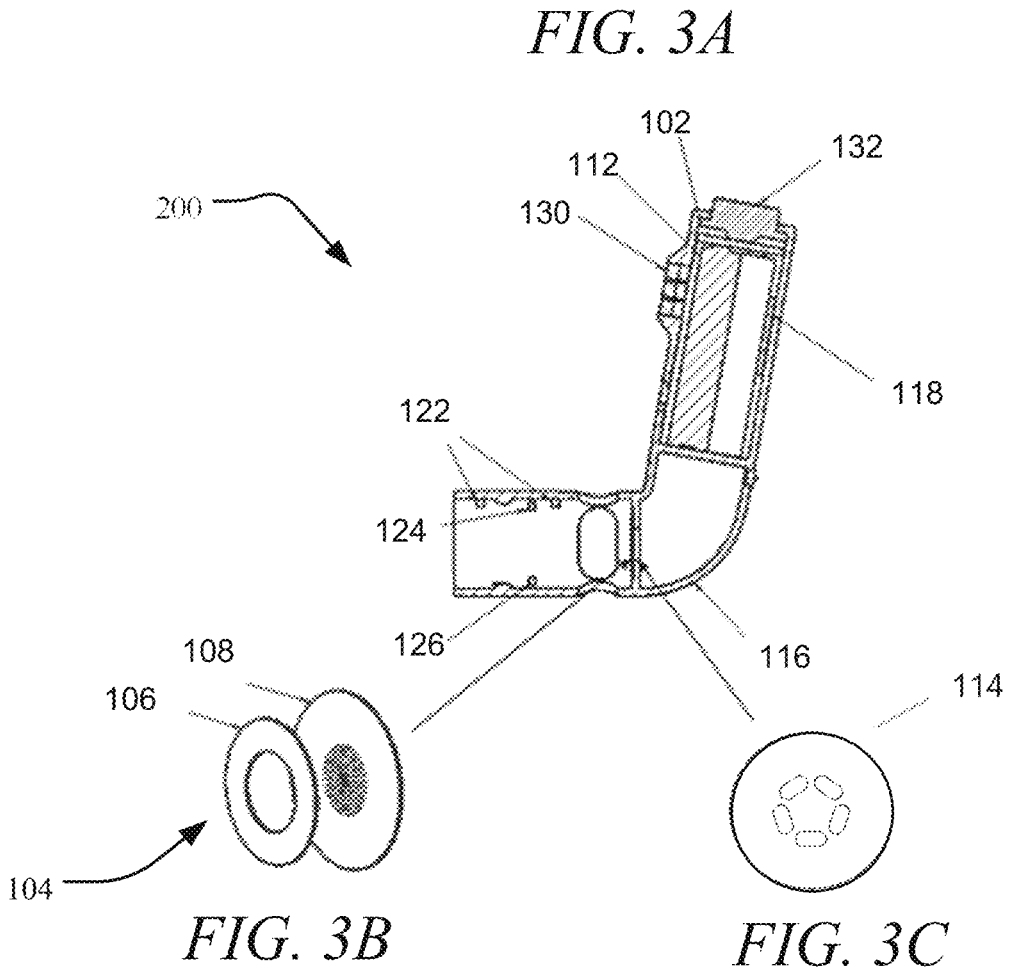
FIG. 3A is another embodiment of a droplet delivery device.

Referring to FIGS. 3A-3C, another implementation of a droplet delivery device of the disclosure is illustrated. Again, like components are illustrated with like reference numbers. In the embodiment shown, droplet ejector device 200 may include an ejector mechanism 104 that is vertically oriented. As illustrated, droplet ejector device 200 is comprised of electronics circuit board 102; ejector mechanism 104 including piezoelectric actuator 106 and aperture plate 108 (FIG. 3B); surface tension plate 114 (FIG. 3C), reservoir 110, which may optionally be coupled to the ejector mechanism 104 to form a combination reservoir/ejector mechanism module that is replaceable, disposable or reusable, power source 112 that is coupled to the piezoelectric actuator 106, and activation button 132. The power source 112, when activated will energize the piezoelectric actuator 106 to vibrate the aperture plate 108 to cause a stream of ejected droplets to be ejected through the aperture plate 108 in a predefined direction. The components may be packaged in a housing 116, which may be disposable or reusable. The housing 116 may be handheld and may be adapted for communication with other devices. For example, Bluetooth module 118 may be adapted for communication with the patient's smart phone, tablet or smart device. Device 200 may include one or more sensor or detector means 122, 124, 126 for device activation, spray verification, patient compliance, diagnostic means, or part of a larger network for data storage, and for interacting and interconnected devices used for subject care and treatment. The device may be unitary, two pieces or three pieces, e.g., with a disposable combination reservoir/ejector mechanism module, a disposable mouthpiece and disposable or reusable electronics unit.

Any suitable material may be used to form the housing of the droplet delivery device. In particular embodiment, the material should be selected such that it does not interact with the components of the device or the fluid to be ejected (e.g., drug or medicament components). For example, polymeric materials suitable for use in pharmaceutical applications may be used including, e.g., gamma radiation compatible polymer materials such as polystyrene, polysulfone, polyurethane, phenolics, polycarbonate, polyimides, aromatic polyesters (PET, PETG), etc.

In certain aspects of the disclosure, an electrostatic coating may be applied to the one or more portions of the housing, e.g., inner surfaces of the housing along the airflow pathway, to aid in reducing deposition of ejected droplets during use due to electrostatic charge build-up. Alternatively, one or more portions of the housing may be formed from a charge-dissipative polymer. For instance, conductive fillers are commercially available and may be compounded into the more common polymers used in medical applications, for example, PEEK, polycarbonate, polyolefins (polypropylene or polyethylene), or styrenes such as polystyrene or acrylic-butadiene-styrene (ABS) copolymers.

As mentioned above, in certain configurations of the disclosure, the reservoir and ejector mechanism may be integrated together into a combination reservoir/ejector mechanism module that may be removable and/or disposable. In certain embodiments, the combination reservoir/ejector mechanism module may be vertically orientated such that the surface tension plate may facilitate fluid contact between the fluid in the reservoir and the fluid contact surface of the aperture plate. In other configurations, the combination reservoir/ejector mechanism module be horizontally oriented within the device and positioned such that the fluid within the reservoir is in constant contact with the fluid contact surface of the aperture plate.

For instance, with reference to FIGS. 4A-E, the combination reservoir/ejector mechanism module 400 is illustrated including the piezoelectric actuator 106, aperture plate 108, surface tension plate 114, a guide 402 which facilitates and aligns insertion of the module 400 onto the ejector device (not shown), filter 404, and ejector mechanism housing 414. In certain embodiments, filter 404 is comprised of a sandwich structure in which a polymer, metal or other composite material structure includes a micro-size aperture 404B located between two superhydrophobic filters 404A, such as those provided by Nitto Denko, Temish, high performance breathable porous membranes. FIG. 4A shows an exploded view, FIG. 4B shows a top view, FIG. 4C shows a cross sectional view, and FIG. 4D shows an enlarged view of a portion of a module and mechanism for mechanical mounting of the ejector mechanism to the reservoir, in accordance with an embodiment of the disclosure. FIG. 4E shows a side view of an exemplary superhydrophobic filter and micronsized aperture for restricting evaporation, in accordance with an embodiment of the disclosure.

In certain embodiments, module 400 may further include a seal 404C, which seals the fill hole used to dispense fluid into the ampule. Other components include a polymer cap 406 which seals the top of the ampule, a housing cup 408 which includes the surface tension plate 114, an O-ring structure 410 which supports the aperture plate 108 and piezoelectric actuator 106, which make electrical contact to the electronics through connector pins 412.

Also included in the module 400 is an optional bar code (not shown) which may provide electrical contact and electrical feed to the piezoelectric actuator 106, as well as provide information on the drug type, initial drug volume, concentration, e.g.; dosing information such as single or multiple dosing regimens, dosing frequency and dosing times. Additional information that may be included on the barcode which may identify the type of aperture plate, target droplet size distribution and target site of action in the pulmonary airways or body, in general. Alternatively, this information may be carried on an electronic chip embedded in the module which can be read either via a wireless connection or via a signal carried by the piezoelectric power connection or via one or more additional physical contacts. Other information included on the barcode or chip may provide critical drug content information or cartridge identification which may prevent improper use of the device or accidental insertion of expired or improper medication, for example.

In certain embodiments, the droplet delivery devices of the disclosure may further include an ejector closure mechanism, which may provide a closure barrier to restrict evaporation of reservoir fluid through the aperture plate and may provide a protective barrier from contamination for the aperture plate and reservoir. As will be understood by those of skill in the art, together with the reservoir, the ejector closure mechanism may provide for a protective enclosure of the reservoir/ejector mechanism module to thereby minimize evaporative loss, contamination, and/or intrusion of foreign substances into the reservoir during storage.

Figure 5A:
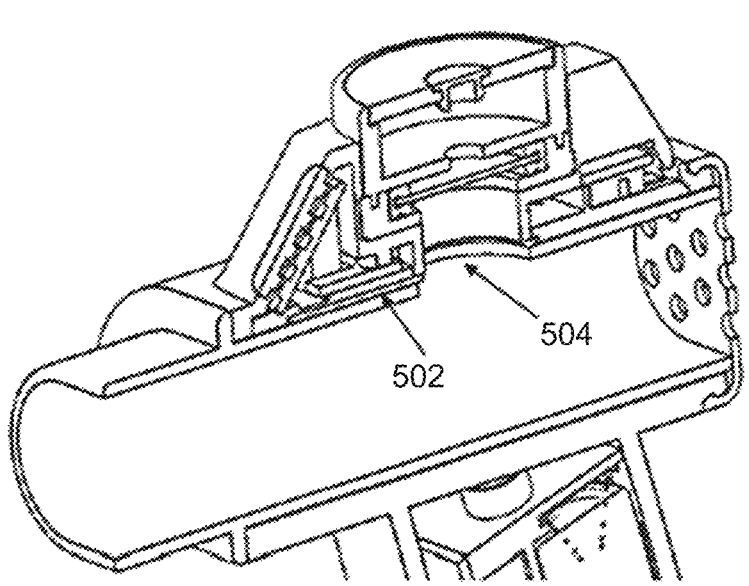
Figure 5B:
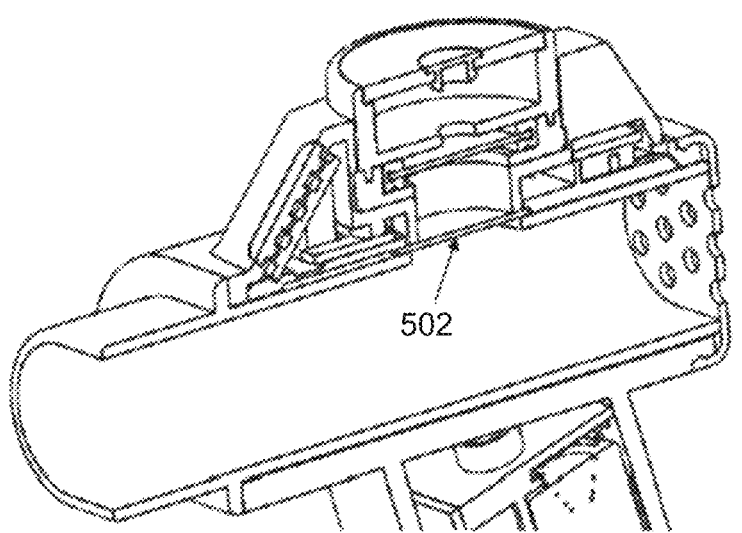

With reference to FIGS. 5A-5B, an exemplary ejector closure mechanism 502 is illustrated at the ejector spray exit port 504 (FIG. 5A showing ejector closure mechanism 502 in an open configuration and FIG. 5B showing ejector closure mechanism 502 in a closed configuration). The ejector closure mechanism can be either manually opened and closed or electronically actuated. In certain embodiments, the ejector closure mechanism may include one or more sensors to prevent operation of the ejector mechanism when the ejector closure mechanism is not open. In other embodiments, the ejector closure mechanism may be automatically powered when the droplet delivery device is powered one, and/or the ejector closure mechanism may automatically close at a predetermined time interval after actuation of a dose, e.g., 15 seconds, 30 seconds, 1 minute, 5 minutes, 10 minutes, etc.

Figure 5E:
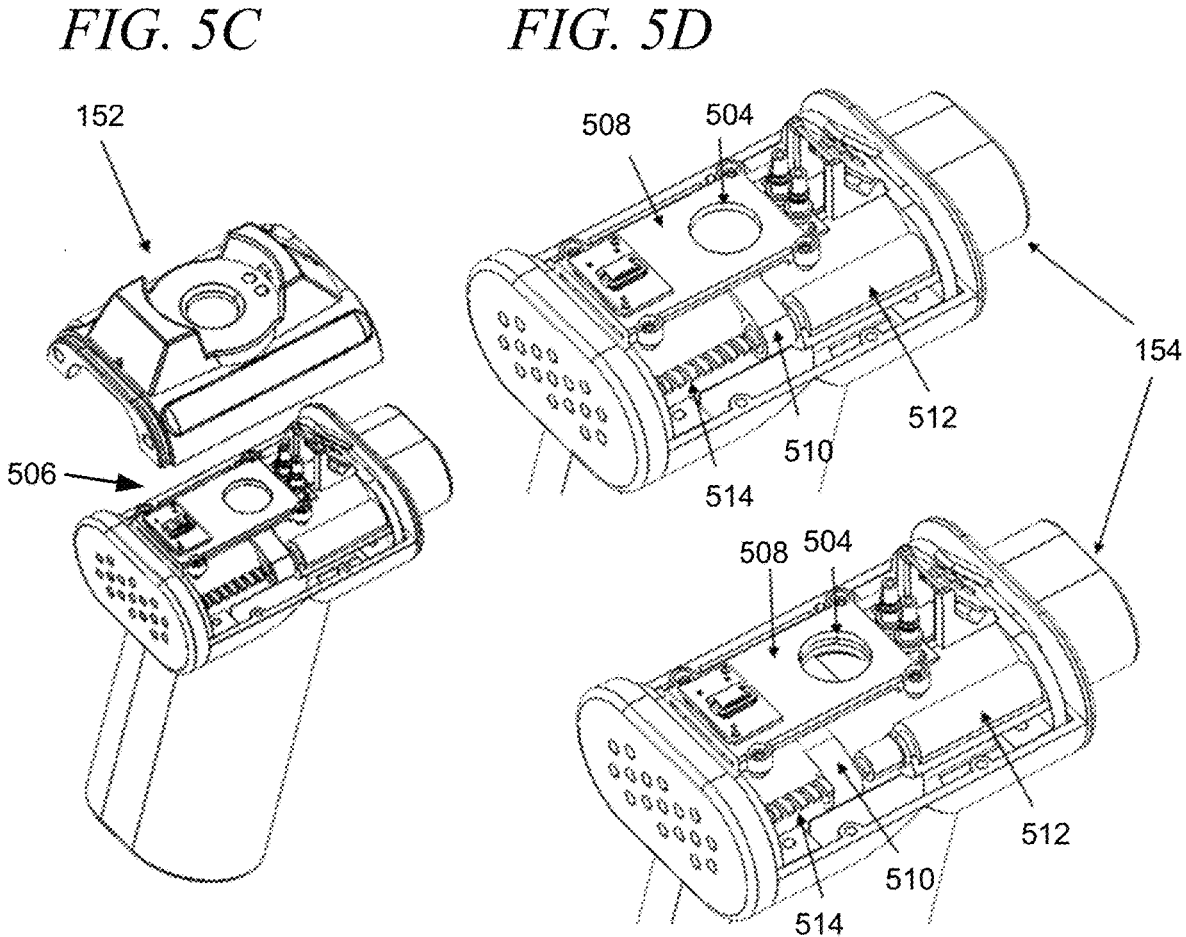
Figures 5F, 5G:
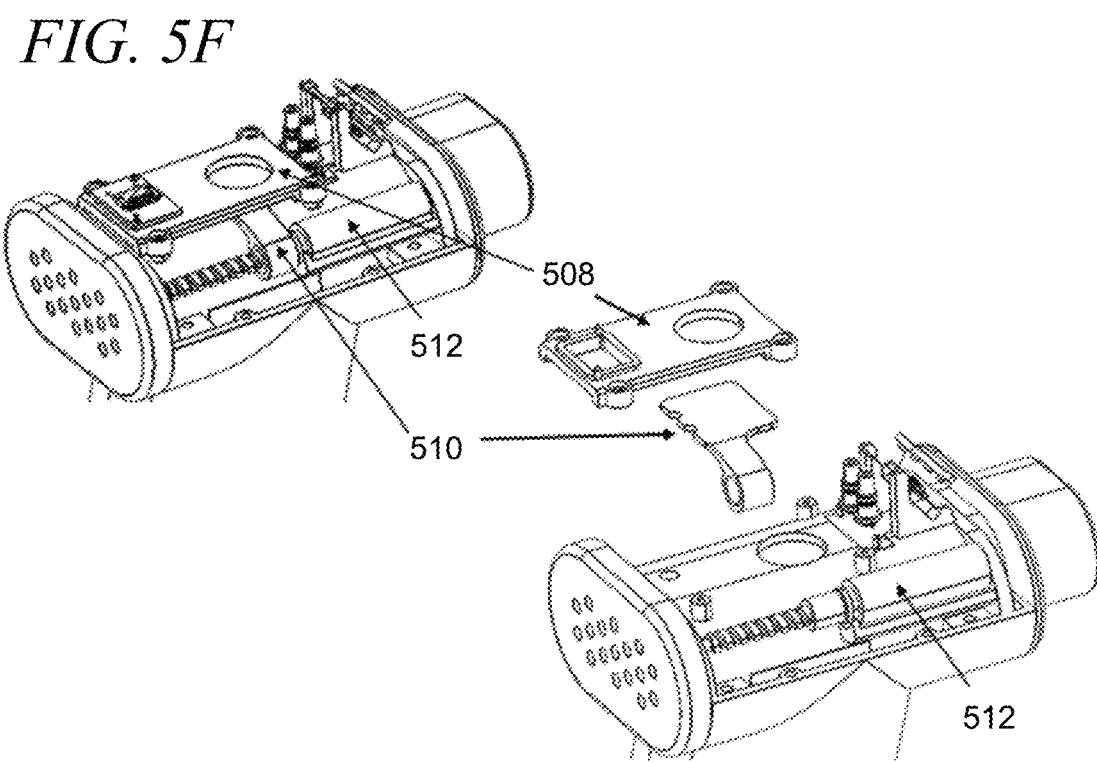

With reference to FIGS. 5C-5E, a more detailed view of an exemplary ejector closure mechanism is provided. Removal of housing top cover 152 exposes the ejector closure actuation mechanism 506 which includes a closure guide 508, sliding seal plate 510, and a motor mechanism 512, which may open and close the sliding seal plate 510 as the motor mechanism 512 is activated. Any suitable miniature motor mechanism may be used, e.g., a thread and screw motor that is piezoelectric driven and actuated such as an ultrasonic swiggle motor from SI Scientific Instruments (www.si-gmbh.de). This mechanism may provide assurance of maintaining a fully sealed reservoir/ejector mechanism module to thereby minimize evaporative losses through the aperture plate or contamination of the aperture plate. FIGS. 5F-5G provide a more detailed, exploded view of the ejector closure mechanism. The sliding seal plate 510 and closure guide 508 are shown in an exploded view.

As described herein, the droplet delivery device of the disclosure generally may include a laminar flow element located at the air entry side of the housing. The laminar flow element, in part, facilitates laminar airflow across the exit side of aperture plate and provides sufficient airflow to ensure that the ejected stream of droplets flows through the droplet delivery device during use. The laminar flow element allows for customization of internal device pressure resistance by designing openings of different sizes and varying configurations to selectively increase or decrease internal pressure resistance.

In certain embodiments, the laminar flow element is designed and configured in order to provide an optimum airway resistance for achieving peak inspirational flows that are required for deep inhalation which promotes delivery of ejected droplets deep into the pulmonary airways. Laminar flow elements also function to promote laminar flow across the aperture plate, which also serves to stabilize airflow repeatability, stability and insures an optimal precision in the delivered dose.

Without intending to be limited by theory, in accordance with aspects of the disclosure, the size, number, shape and orientation of holes in the laminar flow element of the disclosure may be configured to provide a desired pressure drop within the droplet delivery device. In certain embodiments, it may be generally desirable to provide a pressure drop that is not so large as to strongly affect a user's breathing or perception of breathing.

Figure 6A:
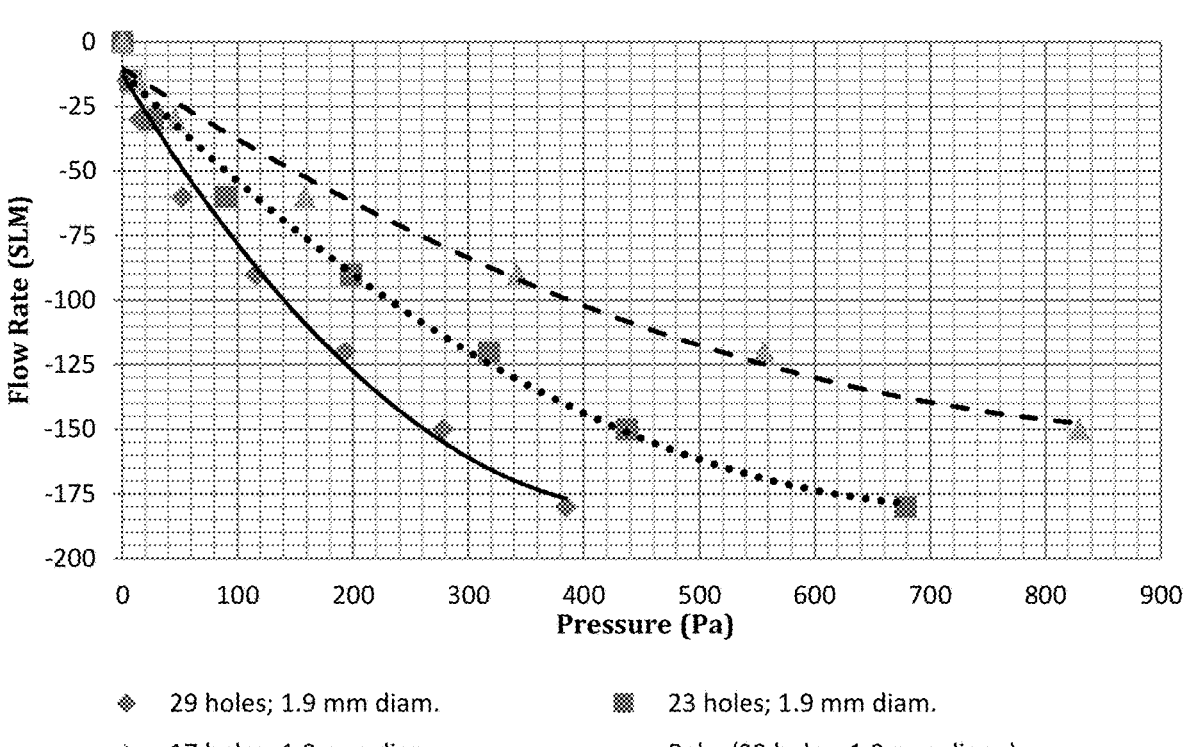
FIG. 6A is a plot of the differential pressure as a function of flow rates through the laminar flow elements mounted on droplet delivery device of the disclosure, as a function of number of holes.
Figure 6B:
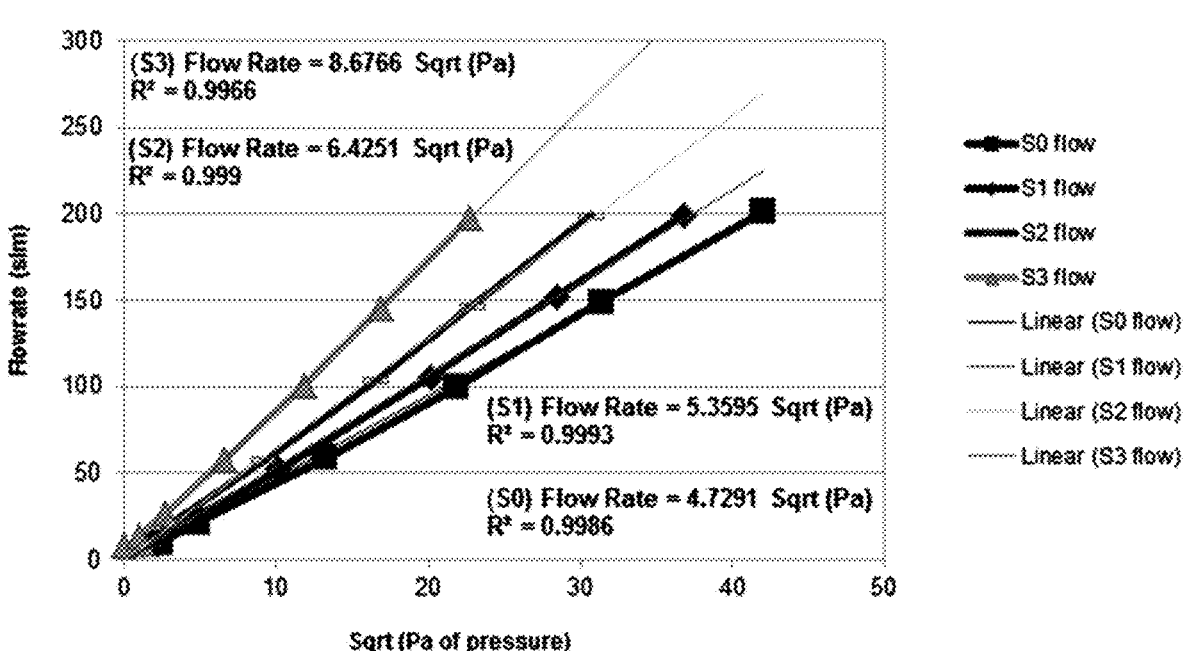
FIG. 6B is a plot of the differential pressure as a function of flow rates through the laminar flow element as a function of screen hole size and number of holes set at a constant, 17 holes.

In this regard, FIG. 6A illustrates the relationship between differential pressure and flow rate through exemplary laminar flow elements of the disclosure as a function of aperture hole diameter (0.6 mm, 1.6 mm and 1.9 mm), while FIG. 6B illustrates differential pressure as a function of flow rates through the laminar flow elements of the disclosure as a function of number of holes (29 holes, 23 holes, 17 holes). Laminar flow elements are mounted on droplet delivery devices similar to that provided in FIG. 2C.

Referring to the following table, the flow rate verses differential pressure as a function of hole size is shown to have a liner relationship, when flow rate is plotted as a function of the square root of differential pressure. The number of holes is held constant at 17 holes. These data provide a manner to select a design for a laminar flow element to provide a desired pressure resistance, as well as provide a model for the relationship between flow rate and differential pressure, as measured in a droplet delivery device similar to that provided in FIG. 2C.

| Inspiratory Flow Rate (SLM) = C(SqRt) (Pressure(Pa)) | | | | |
|---|---|---|---|---|
| Element # | Hole Size (mm) (17 holes) | Pressure at 10 slm (Pa) | Flow at 1000 Pa | Equation Constant (C) |
| 0 | 1.9 | 6 | 149.56 | 4.73 |
| 1 | 2.4 | 2.1 | 169.48 | 5.36 |
| 2 | 2.7 | 1.7 | 203.16 | 6.43 |
| 3 | 3 | 1.3 | 274.46 | 8.68 |

Figure 6C:
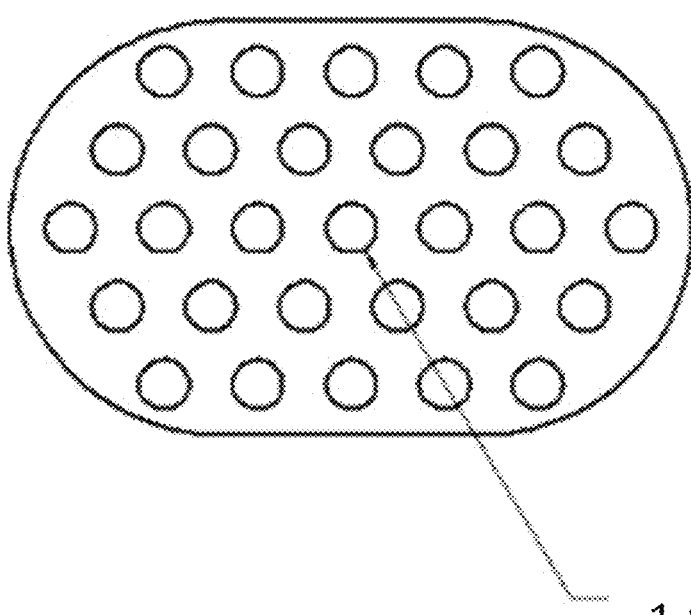
FIG. 6C is a diagram of an air inlet laminar flow screen with 29 holes, each 1.9 mm in diameter.

Referring to FIG. 6C, a non-limiting exemplary laminar flow element is illustrated with 29 holes, each 1.9 mm in diameter. However, the disclosure is not so limited. For example, the laminar flow element may have hole diameters ranging from, e.g., 0.1 mm in diameter to diameters equal to the cross sectional diameter of the air inlet tube (e.g., 0.5 mm, 1 mm, 1.5 mm, 2 mm, 2.5 mm, 3 mm, 3.5 mm, 4 mm, 4.5 mm, 5 mm, 5.5 mm, 6 mm, 6.5 mm, etc.), and number of holes may range from 1 to the number of holes, for example, to fill the laminar flow element area (e.g., 30, 60, 90, 100, 150, etc.). The laminar flow element may be mounted at the air inlet side of a droplet delivery device as described herein.

In certain implementations, the use of laminar flow elements having different sized holes, or the use of adjustable apertures may be required in order to accommodate the differences among the lungs and associated inspiratory flow rates of young and old, small and large, and various pulmonary disease states. For example, if the aperture is adjustable by the patient (perhaps by having a slotted ring that can be rotated), then a method may be provided to read the aperture hole setting and lock that position to avoid inadvertent changes of the aperture hole size, hence the flow measurement. Although pressure sensing is an accurate method for flow measurement, other embodiments may use, e.g., hot wires or thermistor types of flow rate measurement methods which lose heat at a rate proportional to flow rate, moving blades (turbine flow meter technology) or by using a spring-loaded plate, without limitation of example.

As described herein, the droplet delivery device of the disclosure generally may include an ejector mechanism including a piezoelectric actuator coupled directly or indirectly to an aperture plate, the aperture plate having a plurality of openings formed through its thickness. The plurality of openings may have a variety of shapes, sizes and orientations. With reference to FIGS. 7A-7B, exemplary ejector mechanisms of the disclosure are illustrated. FIG. 7A illustrates components of one configuration of an ejector mechanism of the disclosure wherein the piezoelectric actuator 106 may be directly coupled to the aperture plate, and FIG. 7B illustrates another configuration of an ejector mechanism of the disclosure wherein the piezoelectric actuator 106 may be indirectly coupled to the aperture plate 108 via an actuator plate 108b. In the embodiment of FIG. 7B, the piezoelectric actuator 106 is directly coupled to the actuator plate 108b, which is then directly coupled to the aperture plate 108. Upon activation, piezoelectric actuator 106 oscillates the actuator plate 108b, which then in turn oscillates the aperture plate 108 to generate the ejected stream of droplets.

The aperture plate may have any suitable size, shape or material. For example, the aperture plate may have a circular, annular, oval, square, rectangular, or a generally polygonal shape. Further, is accordance with aspects of the disclosure, the aperture plate may be generally planar or may have a concave or convex shape. In certain embodiments, the aperture plate may have a generally domed or half-spherical shape. By way of non-limiting example, with reference to Unlike the predicted and experimentally verified Eigenmodes associated with piezoelectric actuated circular and planar aperture plates, the Eigenmodes associated with domed-shaped aperture plates do not change shape or Eigenmodes with increasing excitation frequency, but retain the domed-shape of the resting aperture plate morphology.

Figure 12A:
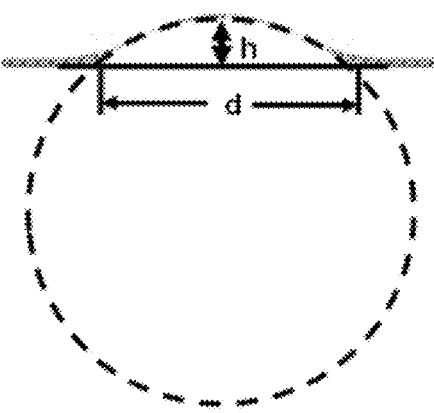
FIGS. 12A-12B illustrate the relationship between aperture plate dome height and active area diameter, in accordance with embodiments of the disclosure.
Figure 12B:
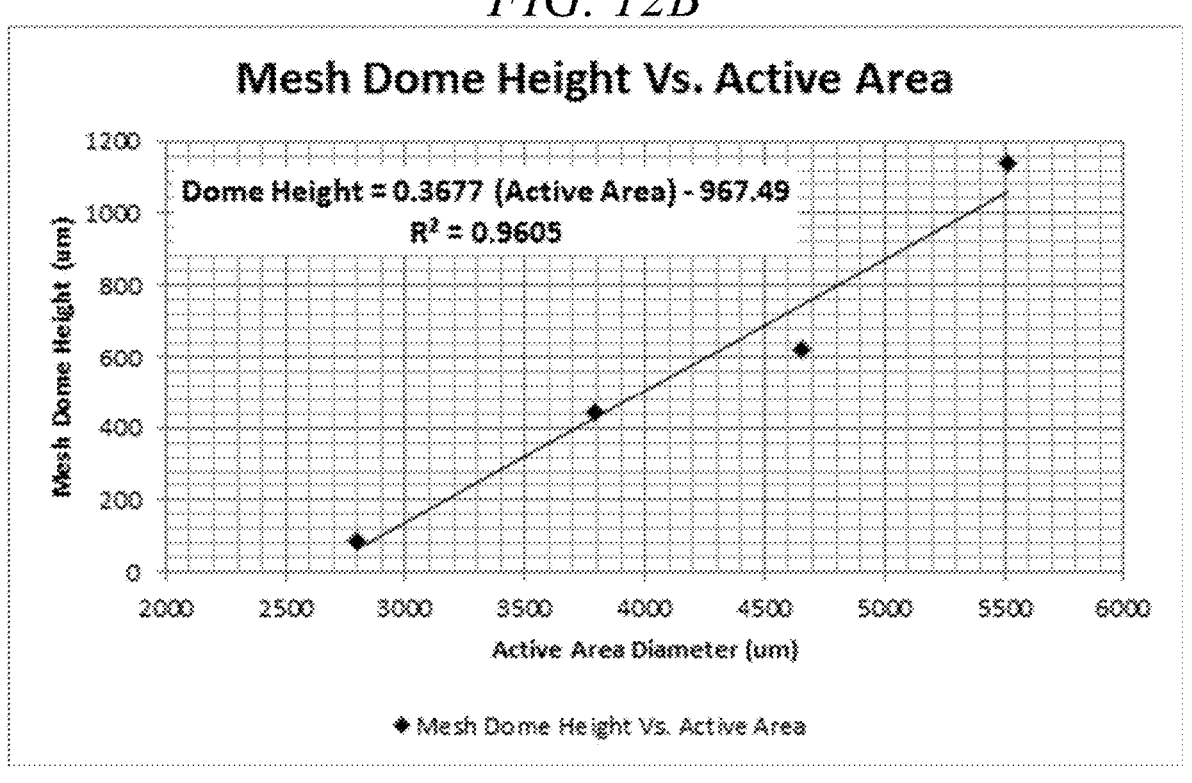

In certain implementations of the disclosure, design parameters that define the domed shape geometry of an exemplary aperture plate include dome height, active area (region including the plurality of openings), and shape and geometry of the dome. Referring to FIG. 12A-12B, the dome height (h) and dome diameter (d) are defined by the arc formed by drawing a circle whose diameter includes the verteces of the perimeter of the active area (FIG. 12A). The resulting equation which defines the parameters dome height and active area (base of dome) are shown in FIG. 12B, which illustrates the relation between aperture plate dome height and active area diameter.

As indicated in the table below, performance comparisons of aperture plates with planar versus domed shapes with regard to droplet generation efficiency as measured by ml of fluid ejected per minute shows that the domed shape provides a significant improvement in performance.

| | Active Area diameter (mm) | Active Area (mm2) | Exit Hole Diameter (um) | Drive Frequency (kHz) | Excitation Voltage (Vpp) | Ejected Volume (ml/min) |
|---|---|---|---|---|---|---|
| Planar shape | 6 | 28.27 | 4 | 113 | 40 | 0.5 |
| Domed shape | 2 | 3.14 | 3 | 109 | 30 | 0.7 |

Figures 8A, 8B:
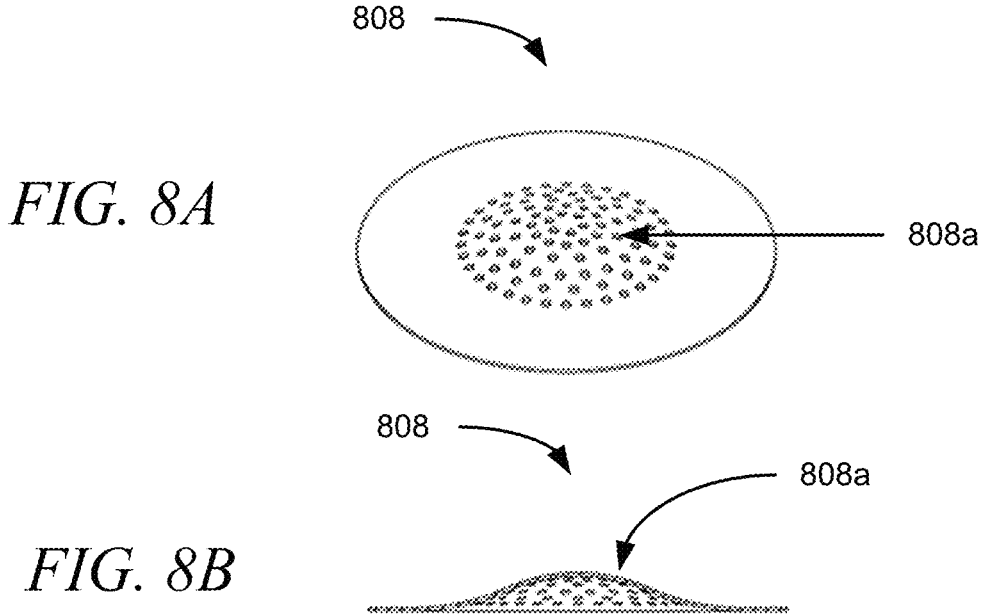
FIGS. 8A-8B depict perspective and side views of an exemplary domed-shaped aperture plate design, in accordance with embodiments of the disclosure.

FIG. 8A-8B, an exemplary aperture plate 808 is illustrated wherein openings 808a are located in a region having a generally domed-shape.

Figure 10A:
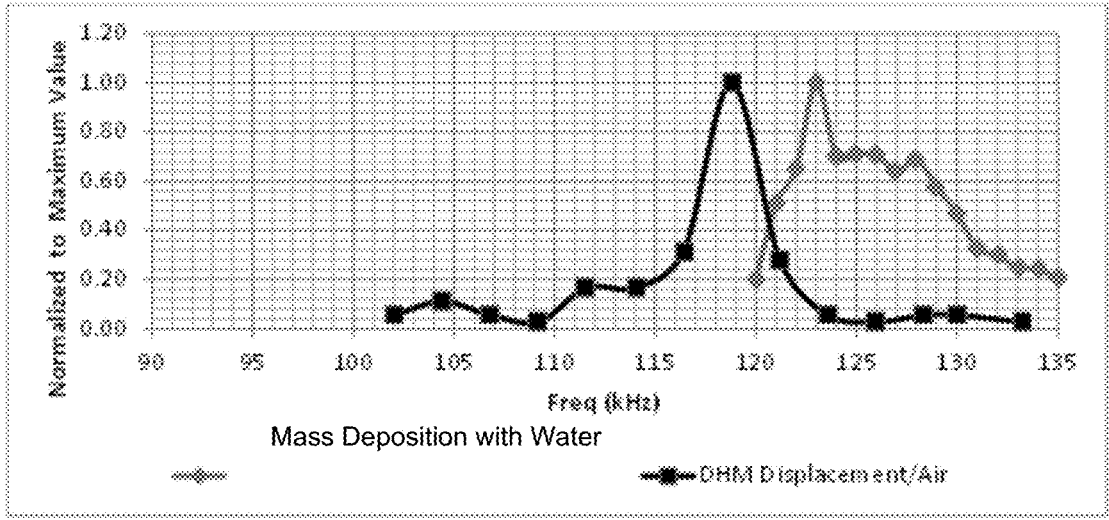
FIGS. 10A-10B are frequency sweep plots displaying medium damping influence on resonant frequency for planar (FIG. 10A) and dome-shaped aperture plates (FIG. 10B), in accordance with embodiments of the disclosure.
Figure 10B:
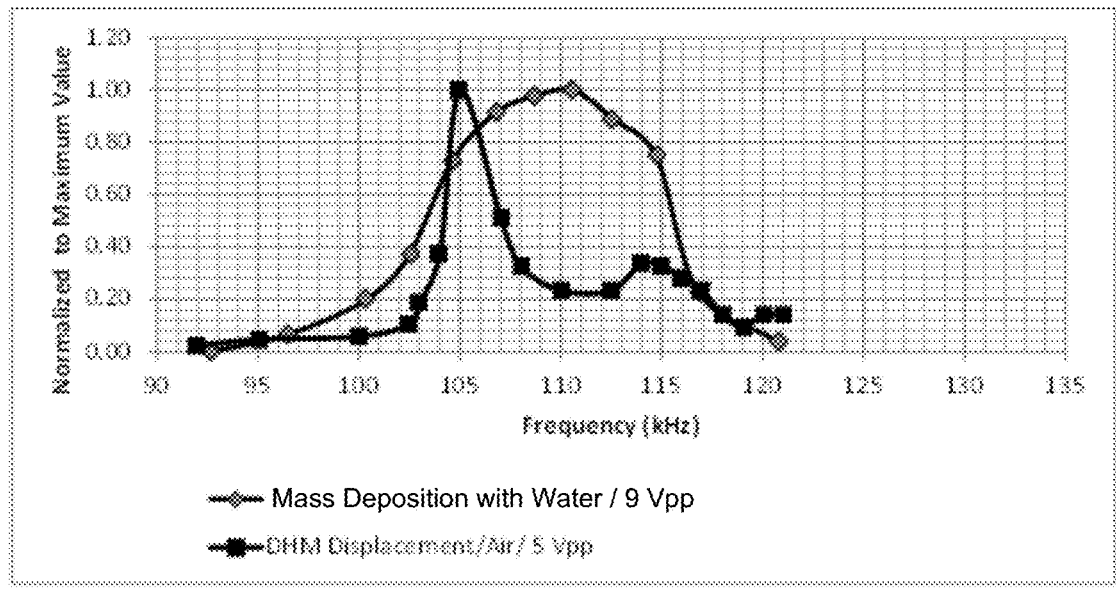

In this regard, in certain aspects of the disclosure, it was unexpectedly found that improved ejector mechanism performance may be obtained with aperture plates having a generally domed-shape. Referring to FIGS. 10A-10B, a comparison of the medium damping influence of air verses distilled water on resonant frequency for planar (FIG. 10A) versus domed-shaped aperture plates (FIG. 10B) is provided. These plots suggest that ejector mechanisms using domed-shaped aperture plates are more stable and less sensitive to viscosity, and mass loading and medium damping effects, in comparison to ejector mechanism using planar aperture plates. Ejector mechanisms using domed-shaped aperture plates provide improved performance by maintaining a stable and optimum resonance frequency. In this regard, a droplet delivery device of the disclosure comprising an aperture plate having a generally domed shape will deliver a more accurate, consistent, and verifiable dose to a subject, with a droplet size distribution that is suitable for successful delivery of medication to the subject's pulmonary system.

Figure 11:
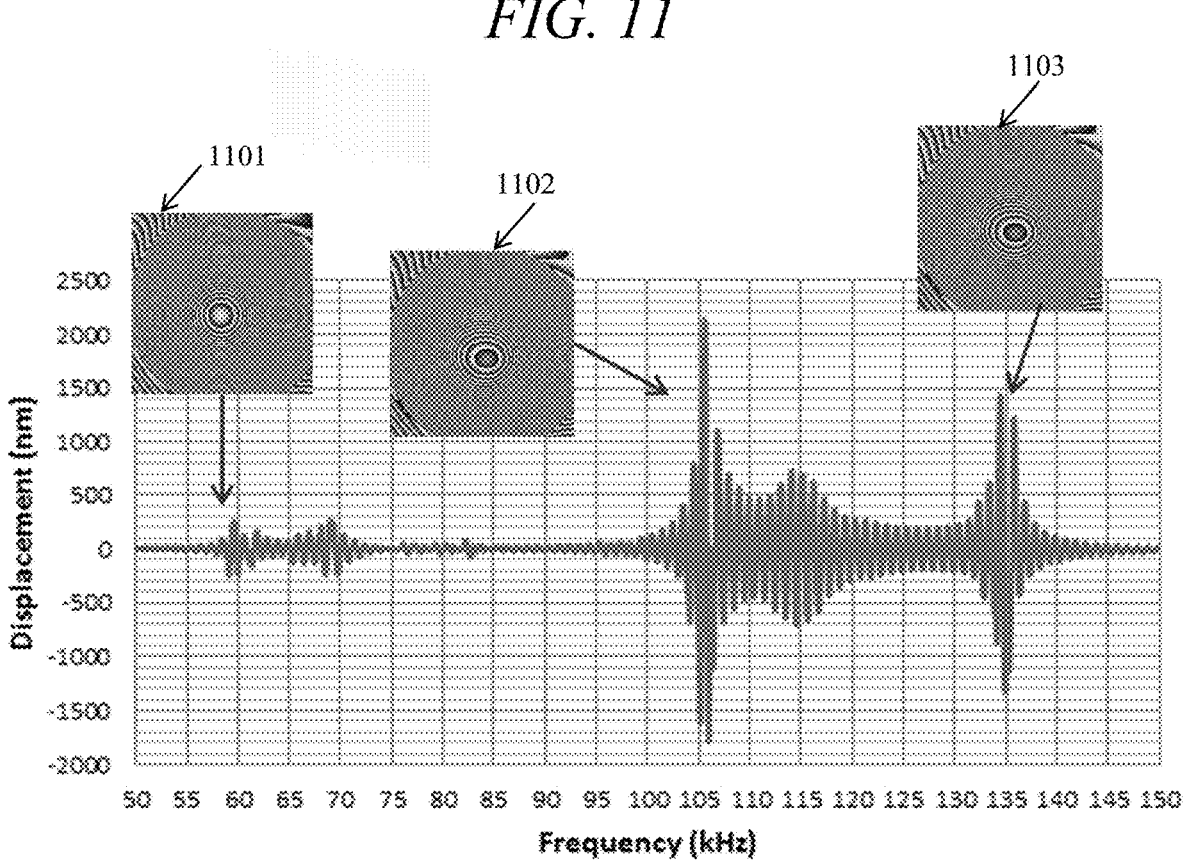
FIG. 11, including insets 1101, 1102 and 1103 illustrate a graph of a DHM-based frequency sweep versus amplitude of displacement of a domed-shaped aperture plate from 50 kHz to 150 kHz and excitation voltage; 5 Vpp. Enlarged in insets 1101, 1102 and 1103 are Eigen mode shapes associated with resonance frequencies 59 kHz (1101), 105 kHz (1102 and 134 kHz (1103).

Referring to FIG. 11, Digital Holographic Microscopy (DHM) was applied to identify the resonance frequencies of a domed-shaped aperture plate in accordance with an aspect of the disclosure. Amplitude of displacement at resonance, and capture of the instantaneous Eigenmode shapes for the vibrating, circular, domed-shaped aperture plates are illustrated, as well as the corresponding graph of the frequency sweep versus amplitude of displacement for the dome-shaped aperture plate from 50 kHz to 150 kHz and excitation voltage; 5 Vpp. With reference to insets of FIG. 11, the Eigenmode shapes associated with resonance frequencies 59 kHz (1101), 105 kHz (1102), and 134 kHz (1103), are shown in call-out images for the domed-shaped aperture plate.

These data indicate that the planar surface ejects 0.5 mL/min over an active surface area of 28.3 $mm^2$ footprint (area) and the domed surface ejects 0.7 mL/min from just a 3.1 $mm^2$ active surface area footprint for similar openings. In other words, the domed surface ejects 12.6 times more mass per unit area of active surface area footprint as compared to the planar surface.

The aperture plate of the disclosure may be formed from any suitable material known in the art for such purposes. By way of non-limiting example, the aperture plate may be composed of a pure metal, metal alloy or high modulus polymeric material, such as, and not limited by example, Ni, NiCo, Pd, Pt, NiPd, or other metals or alloy combinations, polyether ether ketone (PEEK), polyimide (Kapton), polyetherimide (Ultem), polyvinylidine fluoride (PVDF), ultra-high molecular weight polyethylene (UHMWPE), as well as a range of filler materials blended into polymers to enhance physical and chemical properties may be used for aperture plate designs and fabrication. Filler materials can include but are not limited to glass and carbon nanotubes. These materials may be used to increase the yield strength and the stiffness or modulus of elasticity. In one embodiment, the aperture plate may be obtained from Optnics Precision Co. LTD. model No. TD-15-05B-OPT-P90-MED.

In certain embodiments, it may be desirable to provide coatings or surface modification to the aperture plates (chemical or structural) in order to enhance microfluidic properties, render surfaces either hydrophilic or hydrophobic or render surfaces antimicrobial.

In certain implementations of the disclosure an aperture plate formed from the high modulus polymeric may be processed to reduce residual stresses that may accumulate in its morphology and thickness during film formation and fabrication. For example, annealing of PEEK film is a standard procedure suggested by Victrex to obtain optimized crystallinity and to allow relaxation of intrinsic stresses.

(www.victrex.com). The systems and methods for releasing residual stresses in high modulus polymeric materials may provide increased yield strength of an aperture plate formed from such materials so as to optimize its stability in the oscillations of the aperture plate as well as minimize plastic deformation of the entrance and exit orifice geometries of the nozzle plate during actuation. In this regard, the systems and methods for releasing residual stresses in the high modulus polymeric aperture plate may insure delivery and administration of a repeatable, consistent dose of medicament.

Further, PEEK, due to its desirable mechanical performance in dynamic loading and its resistance up to high temperatures, is easily laser micromachined and excimer laser ablated, making it a suitable material for fabrication of aperture plates. By way of a non-limiting example, laser excimer treatment of polymer surfaces, and PEEK surfaces in particular, may be used for surface treatment of PEEK aperture plates in order to improve adhesive bonding of the piezoelectric ceramic to the PEEK aperture plate. (P. Laurens, et al., Int. J. Adhes. (1998) 18). In addition, laser ablation and fine machining of PEEK may be used to form parallel grooves or other surface structures, which may lead to the formation of superhydrophobic regions on selected surface areas of the PEEK aperture plates, which may inhibit the drug solution or suspension from wetting selected regions of the aperture plate.

By way of non-limiting example, the plurality of openings may range in average diameter from about 1 μm to about 200 μm, about 2 μm to about 100 μm, about 2 μm to about 60 μm, about 2 μm to about 40 μm, about 2 μm to about 20 μm, about 2 μm to about 5 μm, about 1 μm to about 2 μm, about 2 μm to about 4 μm, about 10 μm to about 40 μm, about 10 μm to about 20 μm, about 5 μm to about 10 μm, etc. Further, in certain embodiments, various openings on an aperture plate may have the same or different sizes or diameters, e.g., some may have an average diameter in a range of about 1 μm to about 2 μm and others may have a diameter of about 2 μm to about 4 μm or about 5 μm to about 10 μm, etc. For instance, holes of differing sizes may be used to generate droplets within a varied size range to target different areas of the pulmonary system, e.g., to target the tongue, oral cavity, pharynx, trachea, upper airways, lower airways, deep lunges, and combinations thereof.

Aperture plate thickness may range from about 10 μm to about 300 μm, about 10 μm to about 200 μm, about 10 to about 100 μm, about 25 μm to about 300 μm, about 25 μm to about 200 μm, about 25 μm to about 100 μm, etc. Further, the number of openings in the aperture plate may range from, e.g., about 5 to about 5000, about 50 to about 5000, about 100 to about 5000, about 250 to about 4000, about 500 to about 4000, etc. It certain embodiments, the number of openings may be increased or decreased by increasing or decreasing the aperture plate pitch (i.e., opening center-to-center distance). In this regard, an increase in the packing density, i.e. reducing the pitch distance, and increasing the number of opening in the aperture plate leads to an increase in the total droplet ejected volume.

In certain implementations, the openings in the aperture plate may have a generally cylindrical shape, tapered, conical, or hour-glass shape. In certain embodiments, the openings may have a generally fluted shape, with a larger opening at one surface of the aperture plate, a smaller opening at the opposite surface of the aperture plate, and a capillary therebetween. The larger and smaller of the openings may be oriented towards the fluid entrance or fluid exit surface of the aperture plate, as desired.

Figure 9:
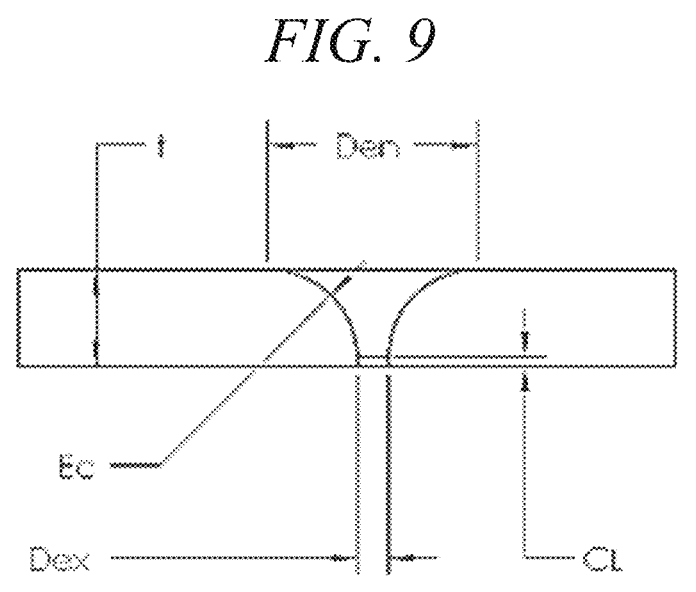

In the embodiment shown in FIG. 9, the aperture plate is oriented with the larger opening oriented towards the fluid entrance, and the smaller opening oriented towards the fluid exit. Without intending to be limited by theory, the aperture plate opening shape, capillary length, and the fluid viscosity determines resistance to flow through the aperture plate opening and can be optimized to provide efficient ejection of droplets.

Referring to FIG. 9, the openings in the aperture plate include a fluid entrance side opening whose diameter ($D_{en}$) is larger than the diameter of the fluid exit side opening ($D_{ex}$). The walls of the fluid entrance chamber are fluted and contoured such that the cross sectional profile of the entrance cavity form a radius of curvature ($E_c$) that is equal to the aperture plate thickness (t) minus the capillary length ($C_L$) as defined by the following equation:

$$E_c = t - C_L$$

where the fluid entrance side opening diameter ($D_{en}$) is equal to 2× the entrance cavity radius of curvature, plus the fluid exit side opening diameter ($D_{ex}$):

$$D_{en} = 2(E_c) + D_{ex}$$

In certain embodiments, optimization of the aspect ratio of the fluid entrance to the fluid exit diameters, in combination with capillary lengths, allows for formation of ejected droplets of fluids having relatively high viscosities.

Any suitable method may be used to manufacture the aperture plates and the plurality of openings within the apertures plates, as may be known in the art and as may suitable for the particular material of interest. By way of example, micromaching, pressing, laser ablation, LIGA, thermoforming, etc. may be used. In particular, laser ablation of polymers is an established process for industrial applications. Excimer laser micromachining is particularly well suited for fabrication of polymeric aperture plates. However, the disclosure is not so limited and any suitable method may be used.

As described herein, the ejector mechanism of the disclosure also comprises a piezoelectric actuator. Piezoelectric actuators are well known in the art as electronic components used as sensors, droplet ejectors or micro pumps, for example. When a voltage is applied across a piezoelectric material, the crystalline structure of the piezoelectric is affected such that the piezoelectric material will change shape. When an alternating electric field is applied to a piezoelectric material, it will vibrate (contracting and expanding) at the frequency of the applied signal. This property of piezoelectric materials can be exploited to produce effective actuators, to displace a mechanical load. As voltage is applied to a piezoelectric actuator, the resulting change in the piezoelectric material's shape and size displaces the load.

As described herein, in certain aspects, the piezoelectric actuator drives the oscillation of the aperture plate which produces the vibration that leads to the formation of the ejected stream of droplets. As an alternating voltage is applied to electrodes on the surface of the piezoelectric actuator, the aperture plate oscillates and a stream of droplets are generated and ejected from the openings in the aperture plate along a direction away from the fluid reservoir.

The piezoelectric actuator may be formed from any suitable piezoelectric material or combination of materials. By way of non-limiting example, suitable piezoelectric materials include ceramics that exhibit the piezoelectric effect such as lead zirconate titanate (PZT), lead-titanate (PbTiO2), lead-zirconate (PbZrO3), or barium titanate (Ba-TiO3). Further, the piezoelectric actuator may have any suitable size and shape, so as to be compatible to oscillate the aperture plate. By way of example, the piezoelectric actuator may have a generally annulus or ring shape, with a center opening that accommodates the active area (the region with the plurality of openings) of the aperture plate so as to allow the ejected stream of droplets to pass through the aperture plate.

In this regard, the use of axisymmetric piezoelectric actuators in the form of an annulus or ring to produce motion in a generally circular substrate plate for a variety of microfluidic applications is well known. A range of actuating voltages may be used as a periodic voltage signal applied in a variety of waveforms, e.g., sinusoidal, square or other implementations, and the direction of the voltage differential may be periodically reversed with the period of oscillation dependent on the resonant frequency of the piezoelectric material, for example to +15V to −15V, or a range peak-to-peak from 5V to 250V. In embodiments of the disclosure, any suitable voltage signal and waveform may be applied to obtain the desired vibration and actuation of the aperture plate.

In piezoelectric actuated devices, the frequency and amplitude of the signal driving the piezoelectric actuator has a significant effect on the behavior of the piezoelectric actuator and its displacement. It is also well known that when the piezoelectric element is at resonance, the piezoelectric device will achieve the greatest displacement of its mechanical load as well as achieve its highest operating efficiency. In addition, a variety of factors can impact the magnitude of displacement of the aperture plate. Factors such as the drive signal of the piezoelectric actuator, the selected resonant frequency, and Eigen mode. Other factors include losses due to the piezoelectric material which originate from its dielectric response to an electrical field and its mechanical response to applied stress, or conversely, the charge or voltage generation as a response to the applied stress.

In addition, the electrical and mechanical response of the piezoelectric actuator is also a function of fabrication methodology, the configuration and dimensions of the piezoelectric actuator, the position and placement of the mechanical mounting of the piezoelectric actuator onto the aperture plate and droplet delivery device, and the piezoelectric electrode size and mounting, for example.

Figure 13:
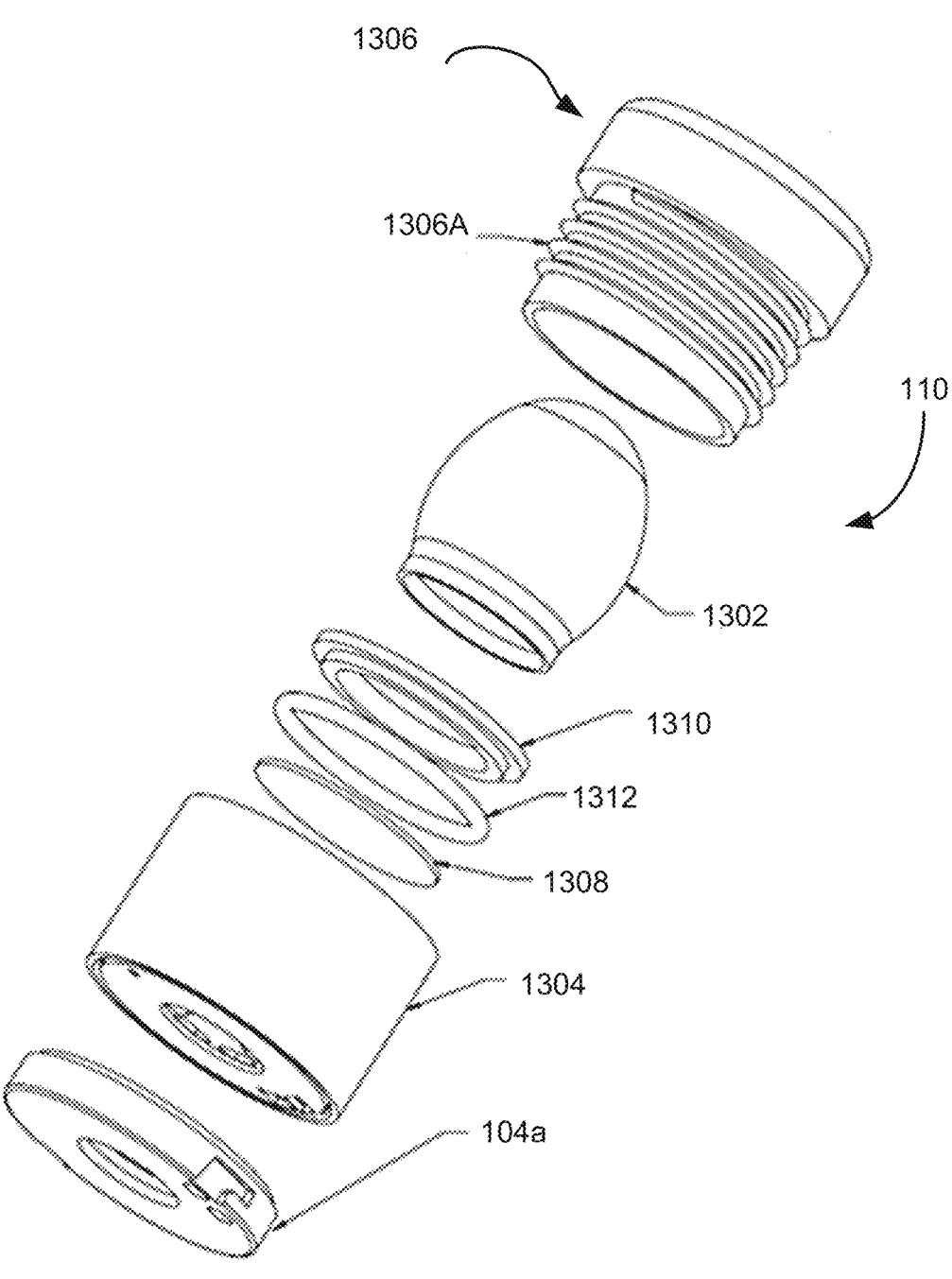
FIG. 13 is an exploded view of reservoir including a flexible drug ampule, in accordance with an embodiment of the disclosure.

In another aspect of the disclosure, the reservoir may be configured to include an internal flexible drug ampoule to provide an airtight drug container. With reference to FIG. 13, an exemplary reservoir 110 is illustrated including a flexible drug ampule 1302 packaged within a hard shell structure 1304, a lid closure 1306 that may include a screw closure 1306A design (illustrated), a snap-in design or other alternate closure system (not shown), and an ejector mechanism housing 104A. The reservoir with flexible drug ampoule also includes foil lidding 1308, a retainer ring 1310, which provides a rigid structure to support the flexible ampule as well as provide a slot to house an O-ring 1312, which prevents leakage once the foil lidding 1308 is punctured to release its contents. In certain embodiments, hard shell structure 1302 may include one or more puncture elements (not shown) that are turned or otherwise put into position to puncture foil lidding 1308 once reservoir 110 is put into position on the base of the droplet delivery device. Once the foil lidding 1308 is perforated, the fluid within the flexible drug ampule 1302 is able to flow out to the ejector mechanism.

In accordance with embodiments of the disclosure, the flexible drug ampule may be formed using conventional form-fill-seal processes. Medical film materials that are available for its structure are shown below and include primarily micro-thick (e.g., 2-4 mil), low density polyethylene film.

| Manufacturer | Product Name | Description |
|---|---|---|
| The Dow Chemical Company | LDPE 91003 Health+ and LDPE 91020 Health | Low density polyethylene film |
| Lyondell Basell Industries | Purell PE 3420F | Low density polyethylene film |
| Borealis Group | Bormed LE6609-PH | Steam sterilizable polyethylene (above 110 C.) |
| Alcan Packaging | Pouch laminate | High barrier lidding |
| Pharmaceutical Packing Inc. | Product Code 92036 | coextruded composite of PET, adhesive, aluminum, polyethylene |
| Texas Technologies | SV-300X | 3 mil nylon, EVOH, poly coex |
| SAFC Biosciences | Bioeaze | Ethyl vinyl acetate film |

In another aspect of the disclosure, the droplet delivery device may comprise a surface tension plate placed in proximity to the aperture plate on the fluid contact side of the aperture plate. As described above, the surface tension plate, at least in part, directs and focuses fluid to the aperture plate. More particularly, in certain embodiments, the surface tension plate may be on the on the fluid contact side of the aperture plate so as to provide for a uniform distribution of fluid onto the aperture plate from the reservoir. In certain aspects of the disclosure, as will be described in further detail herein, the distance of placement of the surface tension plate from the aperture plate provides for an optimization of performance of the ejector mechanism, as measured by ejected droplet mass rate.

Figure 14A:
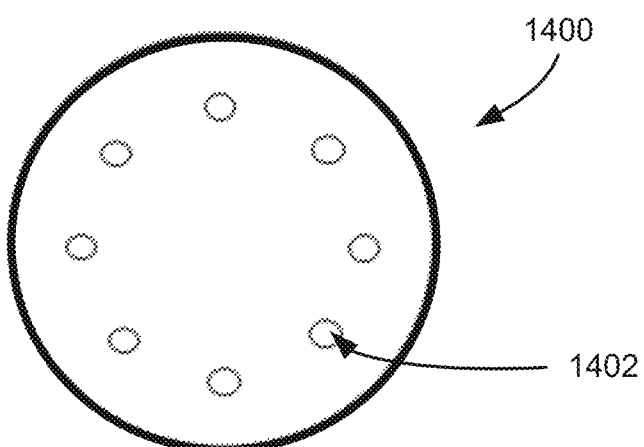
FIGS. 14A-14B are top views of exemplary surface tension plates, in accordance with embodiments of the disclosure.
Figure 14B:
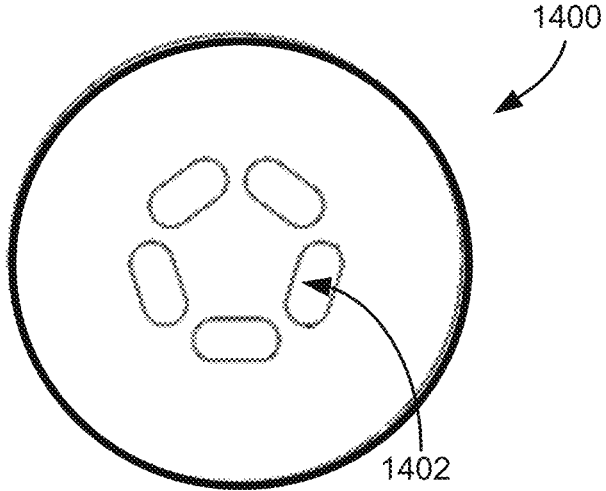

Without intending to be limited, the surface tension plate may have a grid of perforations or holes of various sizes and configurations that may have circular, square, hexagonal, triangular or other cross-sectional shapes. In certain embodiments, the perforations or holes may be located along the perimeter, the center, or throughout the entirety of the surface tension plate. Any suitable size and configuration of perforations or holes may be used such that the desired hydrostatic pressure and capillary action is achieved, as described herein. FIGS. 14A-14B illustrate exemplary perforation or hole 1402 configurations of various surface tensions plates 1400 of the disclosure. Any suitable material known in the art for pharmaceutical application may be used such that it does not interact to components of the droplet delivery device or the fluid to be delivered. For instance, pharmaceutically inert polymers known in the art for such purposes such as polyethylenes and nylons may be used.

In certain embodiments, as illustrated in FIGS. 2A-2B, the surface tension plate may be located in proximity to and behind the aperture plate, generally on the fluid contact side of the aperture plate. Further, in certain embodiments, the surface tension plate may be included as a component of a combination reservoir/ejector mechanism module.

Without intending to be limited by theory, the surface tension plate generates hydrostatic pressure behind the aperture plate, whose magnitude is dependent on the spacing between the surface tension plate and the aperture plate. For example, hydrostatic pressure exerted by fluid increases as the spacing between the surface tension plate and the aperture plate decreases. Furthermore, as the surface tension plate distance from the aperture plate decreases, there is an increase in hydrostatic pressure that is manifested as capillary rise in fluid between the surface tension plate and aperture plate. In this manner, the placement of a surface tension plate on the fluid contact side of the aperture plate can help provide for a constant supply of fluid to the active area of the aperture plate, regardless of the orientation of the inhaler device.

Figure 15A:
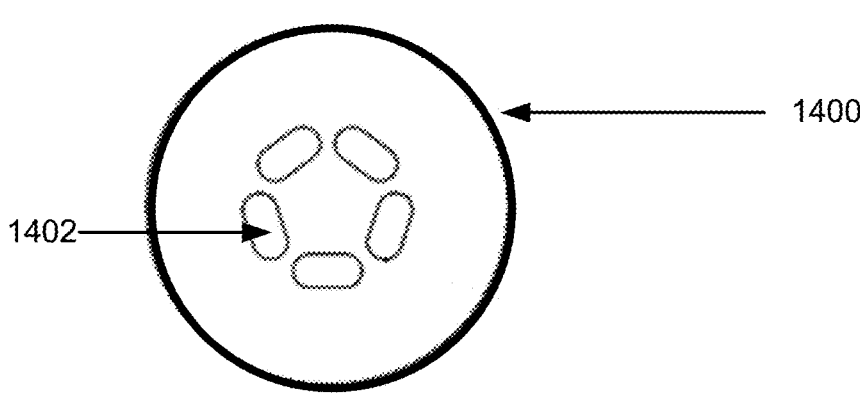
FIG. 15A shows an exemplary top view of a surface tension plate in accordance with an embodiment of the disclosure.
Figure 15B:
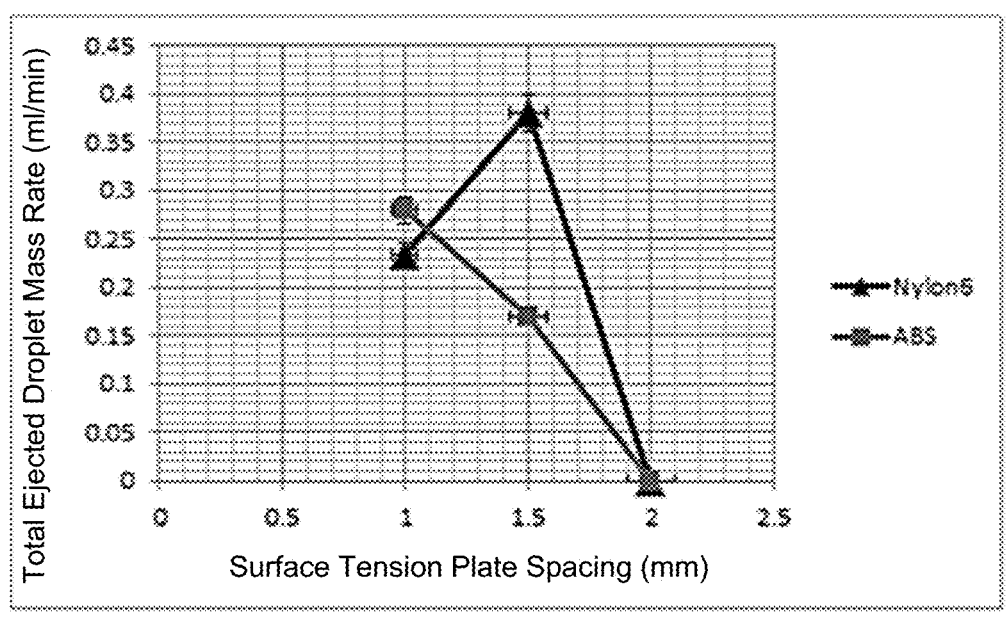
FIG. 15B illustrates the effect of surface tension plate distance from aperture plate and surface tension plate composition on mass deposition, (averages of five, 2.2 sec actuations).

Referring to FIG. 15B, ejected droplet mass rate, as ml/min, is measured gravimetrically by weighing the filled reservoir before and after actuation. The plot displayed in FIG. 15B represents averages of five (5), 2.2 second actuations (sprays) generated using an ejector mechanism including a surface tension plate 1400 with perforations 1402 configured as illustrated in FIG. 15A and a domed shaped aperture plate (not shown). The effect of polymer composition of the surface tension plate on ejector mechanism performance was also tested. Surface tension plates were formed using nylon6 or acrylonitrile butadiene styrene (ABS) copolymer. These compositions were chosen in order to investigate the effect of critical surface tension, water contact angle and spacing between the surface tension plate and aperture plate, on ejector mechanism spray performance.

| Material | Critical Surface Tension (dynes/cm) | Water Contact Angle (degrees) |
|---|---|---|
| Nylon6 | 43.9 | 62.6 |
| ABS | 38.5 | 80.9 |

As illustrated in FIG. 15B, surface tension plates composed of nylon6 demonstrated an unexpected increase in droplet mass rate when placed 1.5 mm away from the dome-shaped aperture plate, as compared to surface tension plates composed of ABS.

While the droplet delivery devices of the disclosure are not so limited, based on surface energy differences between materials of construction, as well as the inverse relationship between hydrostatic forces and distance between the surface tension plate and the aperture plate; surface tension plate distances greater than about 2 mm may not provide sufficient capillary action or hydrostatic force to ensure a constant supply of fluid to the aperture plate. As such, in certain embodiments, the surface tension plate may be placed within about 2 mm of the aperture plate, within about 1.9 mm of the aperture plate, within about 1.8 mm of the aperture plate, within about 1.7 mm of the aperture plate, within about 1.6 mm of the aperture plate, within about 1.5 mm of the aperture plate, within about 1.4 mm of the aperture plate, within about 1.3 mm of the aperture plate, within about 1.2 mm of the aperture plate, within about 1.1 mm of the aperture plate, within about 1 mm of the aperture plate, etc.

In another embodiment of the disclosure, the droplet delivery device may include two or more, three or more, four or more reservoirs, e.g., a multiple or dual reservoir configuration. In certain embodiments, the multiple or dual reservoir may be a combination multiple or dual reservoir/ejector module configuration, which may be removable and/or disposable. The multiple or dual reservoir can deliver multiple medications, flavors, or a combination thereof for polypharmacy.

In certain aspects, this system and methods provides a multiple or dual reservoir configuration that can deliver multiple medications prescribed to a patient, and which may be delivered through the same device. This may be particularly useful for subjects that take medications for multiple indications, or that require multiple medications for the same indication. In accordance with the disclosure, the droplet delivery device may be programed to administer the proper medication in the proper dosage according to the proper administration schedule, e.g., based on barcode or embedded chip information programmed at the pharmacy.

Figures 16A, 16B:
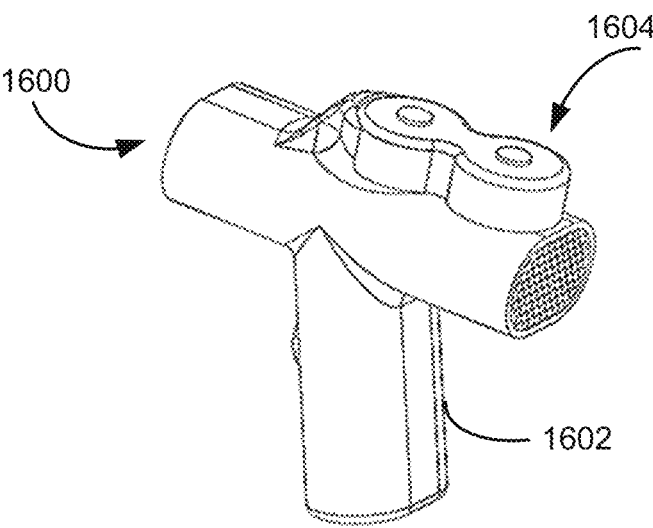
FIG. 16A illustrates a cross-section of a dual combination reservoir/ejector mechanism module, in accordance with an embodiment of the disclosure.
FIG. 16B illustrates a droplet delivery device with a dual combination reservoir/ejector mechanism module, in accordance with an embodiment of the disclosure.

By way of non-limiting example, FIGS. 16A-16B illustrate an exemplary combination dual reservoir/ejector mechanism module and droplet delivery device in accordance with an embodiment of the disclosure. As shown in FIG. 16B, droplet delivery device 1600 includes device base 1602 (comprising a disposable mouthpiece and disposable or reusable electronics unit) and combination dual reservoir/ejector mechanism module 1604. Combination dual reservoir/ejector mechanism module 1604 is shown in further detail in FIG. 16A, including surface tension plate 1606, aperture plate 1608, piezoelectric actuator 1610, optional barcode or embedded chip (e.g., to provide dosing instruction, medication identification, etc.), and module insertion guide 1614. As illustrated, each dual reservoir/ejector mechanism module is generally configured with similar components.

More specifically, the combination dual reservoir/ejector mechanism module may have aperture plates that are similar in design and able to generate ejected droplets with similar droplet size distributions that are targeted for similar regions of the pulmonary airways. Alternatively, use of multiple medications or polypharmacy, may require delivery of medications to different areas of the pulmonary airways. Under these circumstances, each reservoir of the dual reservoir/ejector mechanism module may have an aperture plate with different opening configurations (e.g., different entrance and/or exit opening sizes, spacings, etc.) to deliver different droplet size distributions targeting different regions of the pulmonary airways.

In other embodiments, the disclosure also provides a single or dual disposable/reusable drug reservoir/ejector module that can deliver multiple medications, flavors, or combinations thereof for polypharmacy in which the aperture plate may include openings with multiple size configurations (e.g., different entrance and/or exit opening sizes, spacings, etc.). Aperture plates with openings having multiple size configurations generate droplets of different size distributions, thereby targeting different regions of the pulmonary airways. Although many-sized-hole combinations are possible, by way of non-limiting example, various combinations and densities of openings having average exit diameters of e.g., about 1 μm, about 1 μm, about 3 μm, about 4 μm, about 10 μm, about 15 μm, about 20 μm, about 30 μm, about 40 μm, etc.

By way of non-limiting example, one opening may have an average exit diameter of 4 μm and an octagonal array of 8 larger openings having an average exit diameter of 20 μm. In this manner, the aperture plate may deliver both larger droplets (about 20 μm in diameter) as well as smaller droplets (about 4 μm in diameter), which can target different regions of the pulmonary airways and which, for example, may simultaneously deliver flavors to the throat and medication to the deep alveolar passageways.

Another aspect of the present disclosure as described herein, provides droplet delivery device configurations and methods to increase the respirable dose of an ejected stream of droplets by filtering and excluding larger droplets (having a MMAD larger than about 5 µm) from the aerosol plume by virtue of their higher inertial force and momentum (referred to herein as "inertial filtering"). In the event that droplet particles having MMAD larger than 5 µm are generated, their increased inertial mass may provide a means of excluding these larger particles from the airstream by deposition onto the mouthpiece of the droplet delivery device. This inertial filter effect of the drug delivery device of the disclosure further increases the respirable dose provided by the device, thus providing improved targeting delivery of medication to desired regions of the airways during use.

Without intending to be limited by theory, aerosol droplets have an initial momentum that is large enough to be carried by the droplet plume emerging from the aperture plate. When a gas stream changes direction as it flows around an object in its path, suspended particles tend to keep moving in their original direction due to their inertia. However, droplets having MMAD larger than 5 µm generally have a momentum that is sufficiently large to deposit onto the sidewall of the mouthpiece tube (due to their inertial mass), instead of being deflected and carried into the airflow.

Inertial mass is a measure of an object's resistance to acceleration when a force is applied. It is determined by applying a force to an object and measuring the acceleration that results from that force. An object with small inertial mass will accelerate more than an object with large inertial mass when acted upon by the same force.

To determine the inertial mass of a droplet particle, a force of F, Newtons is applied to an object, and the acceleration in $m/s^2$ is measured. Inertial mass, m, is force per acceleration, in kilograms. Inertial force, as the name implies is the force due to the momentum of the droplets. This is usually expressed in the momentum equation by the term $(\rho v)v$. So, the denser a fluid, and the higher its velocity, the more momentum (inertia) it has.

area of droplets 5 µm and less in diameter. Region 1 represents a region of laminar flow, while region 2 is an area of turbulent flow due to the generation of entrained air. FIG. 17B illustrates inertial filtering provided by an exemplary droplet delivery device of the disclosure for filtering and excluding larger droplets from the aerosol plume. Droplets undergo a 90 degree change in spray direction (4, 5) as droplets emerge from the ejector mechanism and are swept by the airflow (3) through the laminar flow element before inhalation into the pulmonary airways. Larger droplets above 5 µm (6) are deposited on the sidewall of the mouthpiece tube via inertial filtering.

In certain embodiments, larger droplets may be allowed to pass through the droplet delivery device within the effects of inertial filtering or with varied effects of inertial filtering. For instance, the incoming airstream velocity may be increased (e.g., through use of the mini-fan described herein) so larger droplet particles may be carried into the pulmonary airways. Alternatively, the exit angle of the mouthpiece tube may be varied (increased or decreased) to allow for deposition of droplets of varying sizes on the sidewalls of the mouthpiece. By way of example, with reference to FIGS. 17C-17D, if the angle of the mouthpiece is changed, the larger or smaller droplets will deposit or pass through the mouthpiece with or without impacting on the sidewalls of the mouthpiece. FIG. 17C illustrates an embodiment with a standard 90 degree turn, while FIG. 17D illustrate a greater than 90 degree turn. The embodiment of FIG. 17D would allow droplets having a slightly larger diameter to pass without impacting on the sidewall of the mouthpiece.

In another aspect of the disclosure, in certain embodiments, the droplet delivery devices provide for various automation, monitoring and diagnostic functions. By way of example, as described above, device actuation may be provided by way of automatic subject breath actuation. Further, in certain embodiments, the device may provide automatic spray verification, to ensure that the device has generated the proper droplet generation and provided to proper dosing to the subject. In this regard, the droplet $$P = \frac{\pi \rho V d^3}{6} \qquad\qquad F = \frac{d(mv)}{dt}$$

Momentum - p
The product of the mass and velocity
is known as the linear momentum.

$$p = m \cdot v \quad \left[ kg \frac{m}{s} \right] \qquad\qquad N \cdot s$$

The first derivation of the momentum with time is Force $$F = \frac{d(mv)}{dt}$$

If m = m(t) and v = v(t) then the derivation is:

$$F = \frac{dm}{dt} v + m \frac{dv}{dt} = \frac{dm}{dt} v + m \cdot a$$

Angular Momentum - L $$L = I \cdot \omega \quad \left[ kg \frac{m^2}{s} \right] = [N \cdot m \cdot s] = \frac{J}{s} \qquad\qquad \frac{J}{s}$$

I - Moment of inertia

Figure 17A:
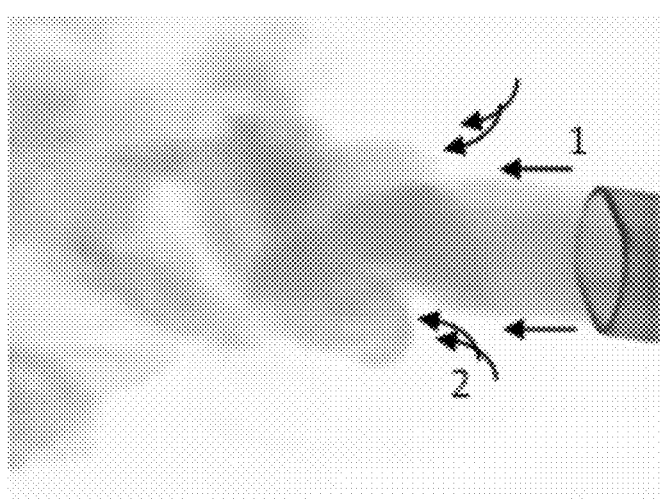
FIG. 17A is a negative image recorded for droplet generation by droplet delivery device, in accordance with an embodiment of the disclosure.
Figure 17B:
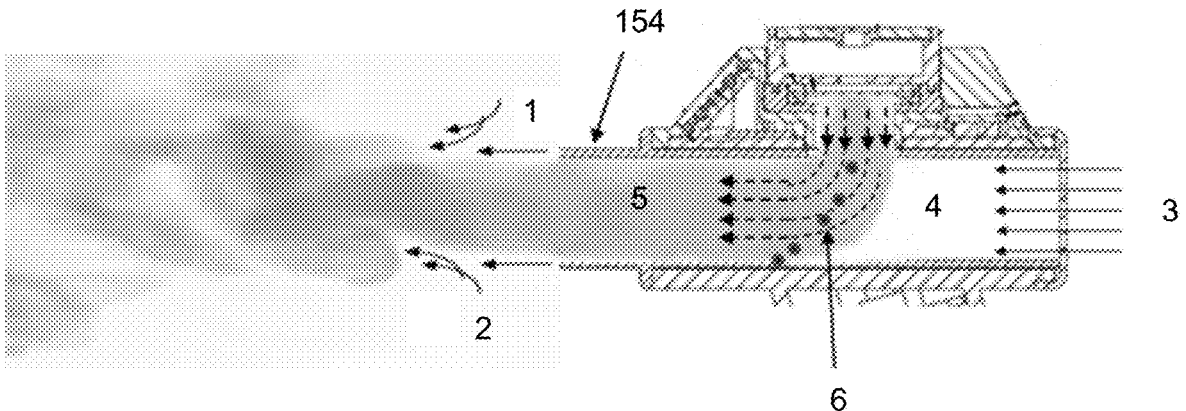
FIG. 17B illustrates a view of inertial filtering for filtering and excluding larger droplets from the aerosol plume, showing droplet flow from a droplet delivery device of the disclosure, with region 1 representing a region of laminar flow and region 2 representing a region of turbulent flow due to the generation of entrained air. Droplets undergo a 90 degree change in spray direction (4-5) as droplets emerge from the ejector mechanism and are swept by the airflow (3) through the laminar flow elements before inhalation into the pulmonary airways.
Figure 17C:
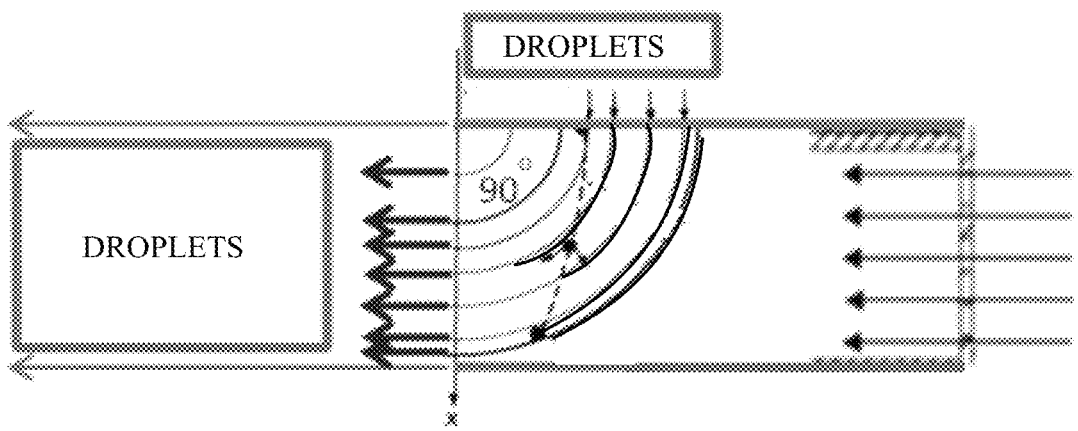
FIGS. 17C-17D depict inertial filter with a mechanism to select droplet size distribution by varying droplet exit angle.
Figure 17D:
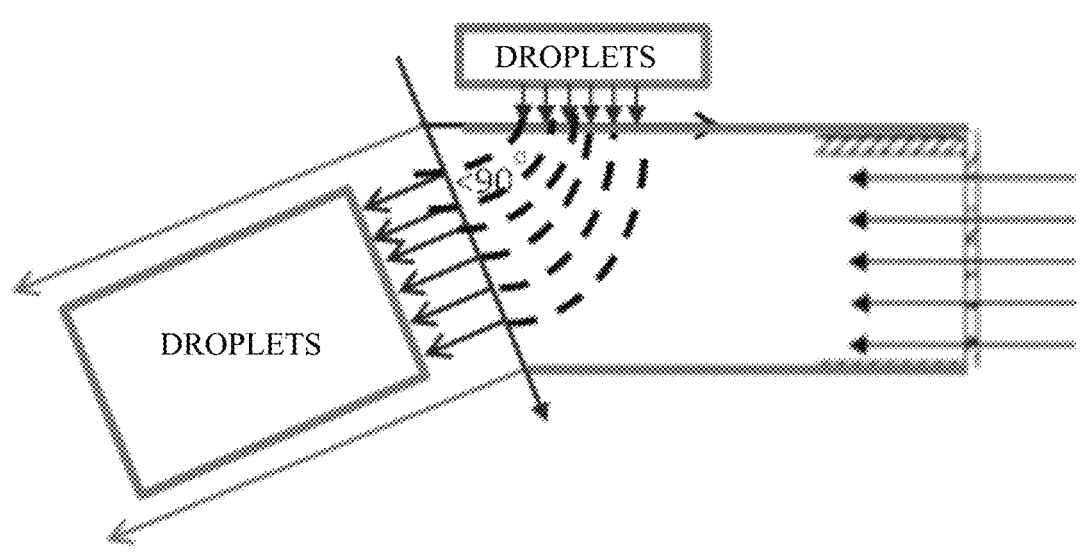

With reference to FIGS. 17A-B, FIG. 17A illustrates a negative image recorded of a stream of droplets generated by a droplet delivery device similar to that of FIGS. 2A-2B. The image provides empirical evidence for the mechanism for generating entrained air from ejected droplets as a consequence of the combined momentum transfer from the droplets to the surrounding air and the large specific surface delivery device may be provided with one or more sensors to facilitate such functionality.

More specifically, in certain embodiments, the droplet delivery device may provide automatic spray verification via LED and photodetector mechanisms. With reference to FIGS. 2A-2C, an infra-red transmitter (e.g., IR LED, or UV LED<280 nm LED), 126 and infra-red or UV (UV with <280 nm cutoff) photodetector 124 are mounted along the droplet ejection side of the device to transmit an infra-red or UV beam or pulse, which detects the plume of droplets and thereby may be used for spray detection and verification. The IR or UV signal interacts with the aerosol plume and can be used to verify that a stream of droplets has been ejected as well as provide a measure of the corresponding ejected dose of medicament. Examples include but not limited to, infrared 850 nm emitters with narrow viewing angles of either, 8, 10 and 12-degrees, (MTE2087 series) or 275 nm UV LED with a GaN photodetector for aerosol spray verification in the solar blind region of the spectra. Alternatively in some applications, the sub 280 nm LEDs (e.g. 260 nm LEDs) can be used to disinfect the spacer tube 128.

By way of example, the concentration of a medicament in the ejected fluid may be made, according to Beer's Law Equation (Absorbance=e L c), where, e is the molar absorptivity coefficient (or molar extinction coefficient) which is a constant that is associated with a specific compound or formulation, L is the path length or distance between LED emitter and photodetector, and c is the concentration of the solution. This implementation provides a measure of drug concentration and can be used for verification and a means and way to monitoring patient compliance as well as to detect the successful delivery of medication.

Figure 18A:
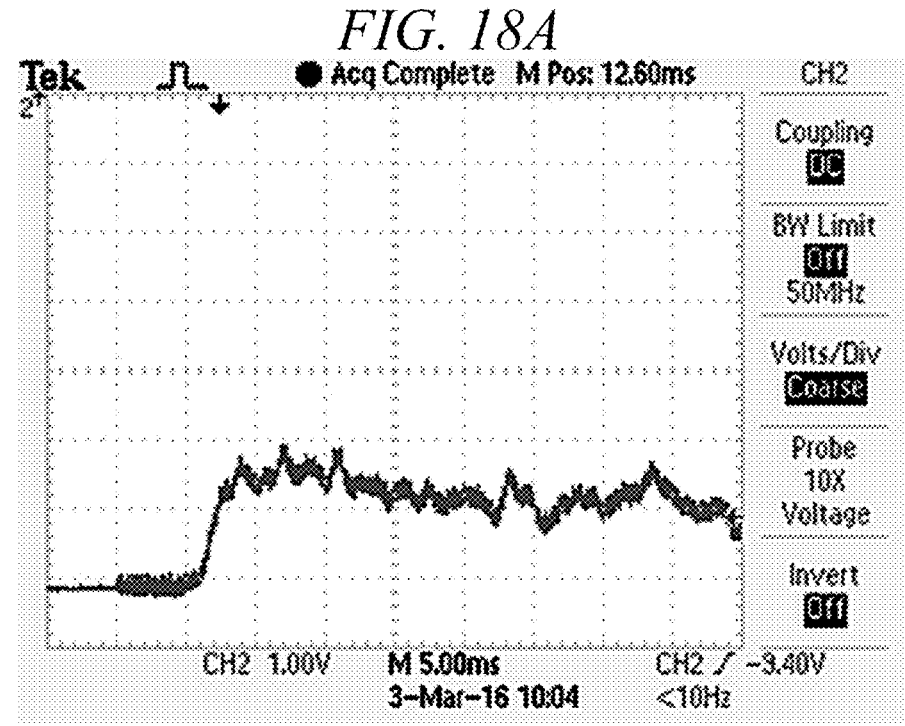
FIGS. 18A-18B are examples of spray verification using (FIG. 18A) deep red LED (650 nm) and/or (FIG. 18B) near IR LED (850 nm) laser and photodiode detectors.
Figure 18B:
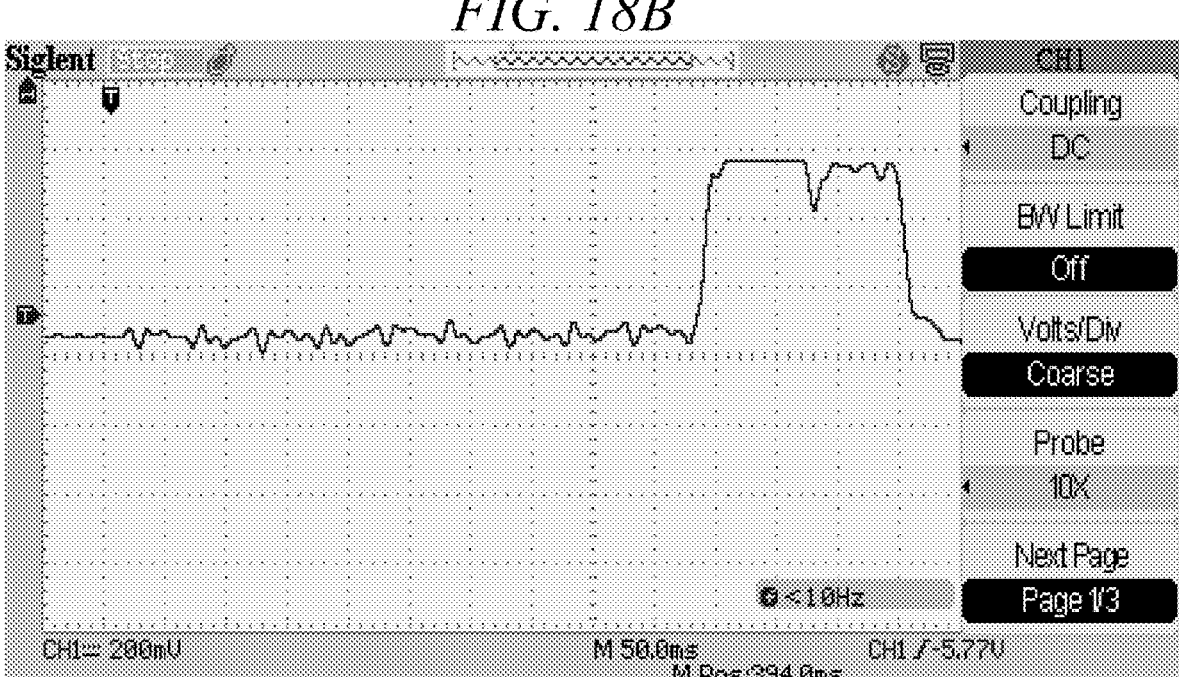

Referring to FIGS. 18A-18B, results are illustrated from exemplary droplet delivery devices including LEDs 126 and photodetectors 124 (with reference to FIGS. 2A-2C), and enabled with automatic spray verification using (FIG. 18A) deep red LED (650 nm) and/or (FIG. 18B) near IR LED (850 nm) laser. Correct generation of a stream of droplets may be confirmed by aerosol plume measurement. By way of non-limiting example, aerosol plume measurement may be implemented at locations in the device mouthpiece tube between the exit end of mouthpiece and the ejector mechanism, across the face of the ejector mechanism, or at both positions. The aerosol plume may be optically measured via light transmission across the diameter of the mouthpiece for an absorption measurement, or by scattering with the photodetector at 90 degrees to the optical illumination so that scattering from the aerosol plume increases the light received at the photodetector.

In yet other embodiments, spray verification and dose verification may be achieved by formulating the fluid/drug to include a compound that fluoresces (or the fluid/drug may naturally fluoresce). Upon delivery of the stream of droplets, the fluorescence may be measured using standard optical means. The light source used for measurement may be modulated, to minimize the effects of external light. When mounted, so that the light path is parallel to and directly across the aperture plate, the generation of droplets by the aperture plate may be directly measured. This direct measurement can allow direct confirmation that the aperture plate is primed and working correctly. When mounted between the droplet exit and the aperture plate, the aerosol plume may be monitored as it passes through the droplet delivery device. The optical means may be any conventional LED with a relatively narrow beam and a half-angle less than twenty degrees. Alternatively, a laser diode may be used to produce a very narrow, collimated beam that will reflect off individual droplets. Various wavelengths from the near UV to the near IR have been used to successfully measure aerosol plume absorption in transmission mode. By using very short wavelength LEDs that are less than 280 nm, interference from sunlight or other conventional light sources can be avoided by placing a filter on the detector than attenuates wavelengths longer than 275 nm. Similarly, if a fluorescing material is added to the fluid/drug, an optical bandpass filter may be placed in front of the detector in order to avoid interference from the stimulation light or external light. Restriction of the ambient light may also be accomplished by utilizing vanes or shades as part of the air-restriction aperture between the device and ambient air.

In another aspect of the disclosure, the droplet delivery device may be used in connection with or integrated with breathing assist devices such as a mechanical ventilator or portable Continuous Positive Airway Pressure (CPAP) machine, to provide in-line dosing of therapeutic agents with the breathing assistance airflow.

For example, mechanical ventilators with endo-tracheal (ET) tubes are used to block secretions from entering the lungs of an unconscious patient and/or to breathe for the patient. The ET tube seals to the inside of the trachea just below the larynx with an inflatable balloon. However, common undesirable side-effects that result from use of mechanical ventilators include ventilator-assisted pneumonia (VAP), which occurs in about ⅓ of patients who are on ventilators for 48 hours or more. As a result, VAP is associated with high morbidity (20% to 30%) and increased health care systems costs. (Fernando, et al., Nebulized antibiotics for ventilation-associated pneumonia: a systematic review and meta-analysis. *Critical Care* 19:150 2015).

Tobramycin administration through the pulmonary route is generally regarded as superior to intravenous administration for treating VAP, with nebulizers being typically used to deliver the antibiotics through generation of a continuous stream of droplets into the ventilator airflow. The main benefit of inhaled versus oral or intravenous administered antibiotics is the ability to deliver a higher concentration of the antibiotic directly into the lungs. However, continuous generation of nebulizer mist provides imprecise dosing that cannot be verified between inhalation and exhalation cycles.

Figure 19:
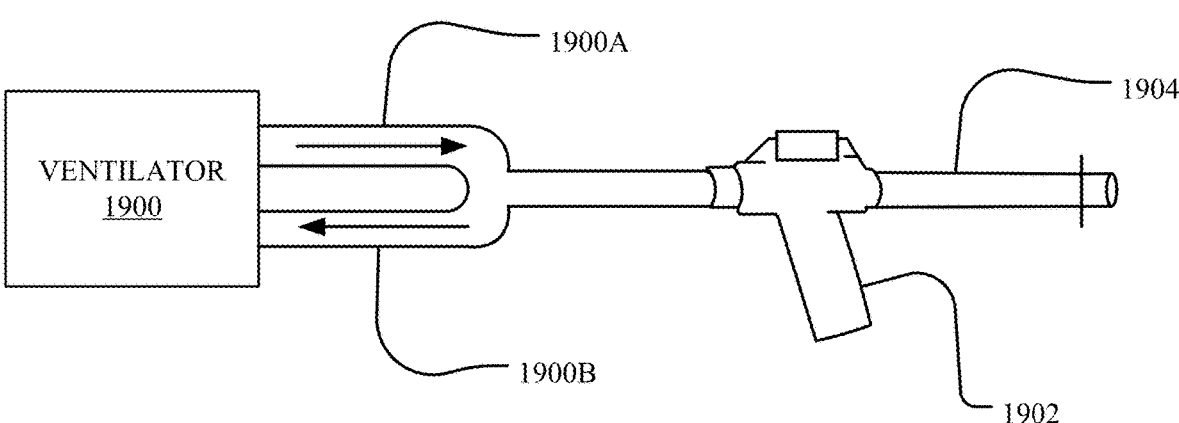
FIG. 19 illustrates a system comprising a droplet delivery device in combination with a mechanical ventilator, in accordance with certain embodiments of the disclosure.

As such, with reference to FIG. 19, an embodiment of the disclosure is provided wherein a droplet delivery device 1902 is placed in-line with a ventilator 1900, (for example a GE Carescape R860). The droplet delivery device 1902 generates a stream of droplets as described herein, which includes a therapeutic agent such as tobramycin, that enters into the ventilator airstream near to the patient end of the endotracheal tube 1904. FIG. 19 provides an example of a standalone device 1902 operating with a ventilator 1900. The ventilator 1900 supplies a stream of inhalation air 1900A and removes a stream of exhalation air 1900B in separate tubes that merge to a single endotracheal tube 1904 close to the patient to minimize mixing of inhalations and exhalations and dead volume. The droplet delivery device 1902 may be placed close to the patient end of the endotracheal tube 1904 in order to minimize loss of droplets that may stick to the tube sidewall. The patient end of the endotracheal tube 1904 is placed in a patient's throat and held in place with a balloon near the end of the tube (not shown).

Actuation of the droplet delivery device is initiated at the start of an inhalation cycle. The droplet delivery device can be battery powered and self-initiating, breath actuated or connected to electronics that are part of the ventilator. The system may be configured so that dosing frequency and duration may be set either within the ventilator or the device. Similarly, droplet ejection timing and duration can be determined by the device or initiated by the ventilator. For example, the device may be programmed to dispense for half a second once every ten breaths on a continuous basis or perhaps once a minute. A device may operate in a standalone manner or communicate the timing of dispenses and flow-rates to the ventilator by a direct electrical connection or via Bluetooth or a similar wireless protocol.

Another aspect of the disclosure provides a system which may also be used with conventional portable CPAP machines to deliver therapeutic agents, e.g., where continuous or periodic dosing during the course of the night is valuable. In another embodiment, the droplet delivery devices of the disclosure many be used in connection with a portable CPAP machine to prevent and treat cardiac events during sleep.

Typically CPAP machines use a mask to supply positive air pressure to a patient while sleeping. Applications of the droplet delivery devices in conjunction with CPAP machines may provide an efficient method for continuous dosing of therapeutic agents such as antibiotics, cardiac medications, etc., for outpatient treatment of diseases, conditions, or disorders, such as pneumonia, atrial fibrillation, myocardial infarction, or any disease, condition, or disorder where continuous or periodic nighttime delivery of a medicine is desired.

In sleep apnea (SA) there are periods of not breathing and an associated decline in blood oxygen level. Not surprisingly, cardiac failure or "heart attacks" are associated with sleep apnea. This association is thought to be due to both the stress on the heart related to low oxygen levels and the increased stress on the heart as the body requires increased blood pressure and cardiac output from the heart. Additionally, there is increased risk of sleep apnea in older and overweight adults. Thus those with SA have a higher risk of heart attacks than the general population because the SA stresses the heart and because the risk factors associated with SA are very similar to the risk factors for heart attacks.

The Journal of New England in 2016 published a four-year study of the effects of CPAP on 2700 men with sleep apnea and found that CPAP significantly reduced snoring and daytime sleepiness and improved health-related quality of life and mood. (R. Doug McEvoy, et al. CPAP for Prevention of Cardiovascular Events in Obstructive Sleep Apnea, *N. ENGL. J. MED.* 375; 10 nejm.org Sep. 8, 2016). However, the use of CPAP did not significantly reduce the number of cardiac events. The article noted that "Obstructive sleep apnea is a common condition among patients with cardiovascular disease, affecting 40 to 60% of such patients."

Many of these cardiac events can be lessened by administration of the proper medication. For example, beta blockers such as Metoprolol can lessen atrial fibrillation and the effects of myocardial infarction to sufficient extent as to prevent death in such an episode.

In certain aspects of the disclosure, the need to lessen adverse cardiac events in the population of people using CPAP devices by sensing the presence of the event and administering an ameliorating drug via pulmonary delivery is addressed. Specifically, a cardiac event may be detected by conventionally available means to detect and evaluate cardiac condition. These include heart rate monitors (such as electrical sensors held in place by an elastic band across the chest or optical monitoring at the earlobe, finger or wrist), automated blood pressure cuffs, or blood-oxygen saturation monitors on the finger or ear). When the monitor detects an adverse condition a specific dose of appropriate drug is administered by a droplet delivery device of the disclosure via the CPAP tube or mask so that the drug is inhaled and carried to the blood stream via deep inhalation into the lung. Pulmonary administration is optimized both by the generation of droplets less than 5 microns in size and delivery of the droplets at the beginning of an inhalation cycle.

Figure 20:
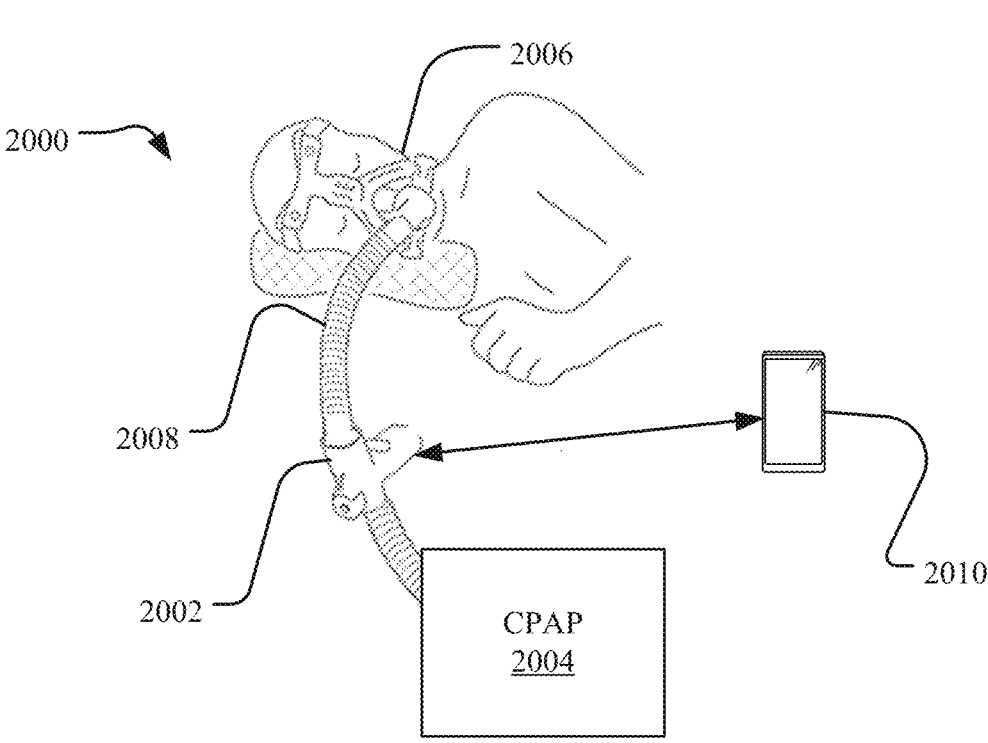
FIG. 20 illustrates a system comprising a droplet delivery device in combination with a CPAP machine, e.g., to assist with cardiac events during sleep, in accordance with certain embodiments of the disclosure.

Referring to FIG. 20, a schematic representation and example for the use of a system 2000 including droplet delivery device 2002 of the disclosure with a CPAP machine 2004 to assist with cardiac events during sleeping. In certain aspects of the disclosure described herein, the patient is shown sleeping with a CPAP mask 2006 in place and pressurized air is delivered to the mask 2006 by the CPAP machine 2004. Cardiac condition is monitored by optical measurement of the heartbeat either at finger, toe, ear lobe or the wrist (not shown). The droplet delivery device 2002 may be placed in-line with the tube 2008 between the CPAP machine 2004 and the CPAP mask 2006, or alternative may be placed at the airflow entrance of CPAP mask 2006 (not shown). Breathing is monitored by airflow measurement in the tube 2008 from the CPAP machine 2004 to the CPAP mask 2006. Airflow rate and direction can be measured by measuring the pressure on either side of a screen which adds a slight amount of airflow restriction. Typically there will be continuous positive airflow which increases in flow rate at inspiration. A controller detects abnormal cardiac condition such as an increase in atrial fibrillation and triggers ejection of droplets of an anti-arrhythmic drug at the start of an inhalation cycle as detected by airflow in the CPAP supply tube. Information may be recorded and stored in a patient's smartphone 2010, and various alerts may be sounded if a cardiac event is detected (e.g., transmitted via Bluetooth or other wireless communication methodology), if desired. Further, the patient's condition and drug dispenses may be monitored via a smartphone app, providing the patient and his medical provider with an accurate record of the patient's condition.

Other diseases commonly associated with sleep apnea, use of a mechanical ventilator, or a CPAP machine may also benefit from a system which non-invasively monitors patient condition and provides pulmonary administration of the appropriate ameliorating medication via a droplet delivery device of the disclosure. For example, those with diabetes frequently are concerned that low blood sugar from a slight insulin overdose will lead to unconsciousness. In this case, abnormally low heartrate, breathing or blood pressure can be detected and sugar or insulin administered via droplets to the pulmonary system.

EXAMPLES

Example A: Automatic Breath Actuation

Referring to FIGS. 1B-1G, droplet delivery device configurations disclosed including various sensor orientations that provide for automatic breath actuation of the ejector mechanism and automatic spray verification. The sensors trigger actuation of an aerosol plume during a peak period of a patient's inhalation cycle. In certain implementations the coordination of a patient's peak period of inhalation may assure optimum deposition of the aerosol plume and associated drug delivery into the pulmonary airways of the patient. Although a number of arrangements are possible, FIG. 1B shows an exemplary sensor configuration. SDPx series (SDP31 or SDP32 pressure sensors) from Sensirion (www.sensirion.com) may be used.

Example B: Droplet Size Distribution

Droplet size distribution and related functionality was evaluated for exemplary droplet delivery devices of the disclosure, including Anderson Cascade Impactor testing, total drug mass output rates, total drug respirable mass, delivery efficiencies and reproducibility. FIGS. 21A-21E provide a summary of the test results.

Test Design

A study was conducted at ARE Labs, Inc. to evaluate the aerosol characteristics and delivered dose of Albuterol sulfate using the Pneuma™ inhaler device. The study was designed to evaluate device performance of a single Pneuma™ inhaler. A series of three (3) individual tests were conducted with a new disposable drug cartridge for each test. The testing platform utilizes an eight-stage nonviable Anderson Cascade Impactor (Thermo Fisher Scientific; Waltham, MA) equipped with a calibrated AALBORG model GFM47 mass flow meter (AALBORG Instruments and Controls; Orangeburg, NY) for flow rate measurement. A valved Gast rotary vane vacuum pump (Gast Manufacturing; Benton Harbor, MI) was used to A droplet delivery device of the disclosure similar to that shown in FIGS. 2A-2C was tested in triplicate with a new reservoir charged with 750 μl of 5000 mg/ml Albuterol sulfate for each of the three (3) conducted tests. A fraction of the drug (100 μl) was extracted from the stock preparation solution of the albuterol sulfate using a calibrated micro pipette, diluted in mobile phase, and analyzed via HPLC for drug concentration. At the conclusion of each test, the mouthpiece was rinsed with mobile phase and collected for HPLC analysis to determine the mass fraction of non-respirable aerosolized drug captured in the mouthpiece via inertial filtering. Following each test, impactor stage samples were extracted and recovered in solvent and analyzed for the active pharmaceutical ingredient (API) using a Dionex Ultimate 3000 nano-HPLC with UV detection (Thermo Scientific, Sunnyvale, CA).

The cascade impactor testing procedure involved fitting the mouthpiece into the Impactor USP throat with a mouthpiece connection seal. The vacuum pump supplying sample air flow to the cascade impactor was turned on and the pump control valves adjusted to supply 28.3 L/min total flow through the impactor and inhaler body during aerosol tests.

At the initiation of each test, a new reservoir was filled with 750 μl of the stock Albuterol sulfate solution with a calibrated micropipette. The device was connected to the impactor USB throat, turned on, and actuated ten (10) times for each test. At the conclusion of the test period, the device, impactor, and dilution air sources were turned off. The mouthpiece was rinsed in order to extract drug, and all stages of the cascade impactor were rinsed with a quantity of appropriate solvent (HPLC mobile phase). Extracted samples were placed in labeled and sterile HPLC vials, capped, and analyzed for drug content via HPLC with UV detection. The mouthpiece was extracted of residual drug and analyzed for drug content via HPLC to measure mouthpiece drug deposition in relation to the total collected on the impactor stages.

All system flow rates and impactor sample flows were monitored throughout each test period. Following each test, the impactor slides were placed in labeled sterile Petri dishes, and impactor stages were extracted of drug using 2 ml of mobile phase applied with a calibrated micropipette. All extracted samples from the mouthpiece and impactor were placed in labeled sterile amber HPLC sample vials, and stored refrigerated at approximately 2° C. until HPLC analysis.

Impactor collection stages for all tests were rinsed with DI water and ethanol, and air dried prior to each inhaler test trial to avoid contamination. A new inhaler drug cartridge was used for each of the three individual tests.

Drug Analysis

All drug content analysis was performed using a Dionex Ultimate 3000 nano-HPLC equipped with a Dionex UVD-3000 multi-wavelength UV/VIS Detector using a micro flow cell (75 μm×10 mm path length, total analytical volume 44.2 nl). The column used for the albuterol sulfate was a Phenomenex Luna (0.3 mm ID×150 mm) C18, 100A (USP L1) column with a column flow rate of 6 μl/min at a nominal pressure of 186 bar. Total HPLC run time was 6 minutes per sample with approximately 5 minutes flush between each sample. Sample injection was performed with a 1 μl sample loop in full loop injection mode. Detection was with UV at 276 nm for albuterol sulfate.

HPLC Method and Standards

US Pharmacopeial monograph USP29nf24s_m1218 was followed as a reference method for analysis of albuterol sulfate. Briefly, the method involved dilution of an appropriate formulation of albuterol sulfate in mobile phase; 60% buffer and 40% HPLC grade methanol (Acros Organics). Buffer formulation contains reverseosmosis filtered deionized water with 1.13 gr of sodium 1-hexanesulfonate (Alfa Aesar) in 1200 ml of water, with 2 ml glacial acetic acid (Acros Organics) added. The mobile phase solution was mixed and filtered through a 0.45 μm filter membrane. The final mobile phase is a 60:40 dilution of Buffer: MEOH.

Statistical Analysis

Mean and standard deviation were calculated for all triplicate trial sets for each component of: inhaler drug fill, total delivered dose, course particle dose, course particle fraction, respirable particle dose, respirable particle fraction, fine particle dose, fine particle fraction, aerosol MMAD and GSD. The number of trials provided for 95% confidence levels for all data sets.

Results

The table below provides a summary of the mass fraction of droplets collected on each droplet size stage of the Anderson Cascade Impactor testing (Albuterol, 0.5%, Anderson Cascade, 28.3 lpm, 10 actuations). As shown, over 75% of the droplets of an average diameter of less than about 5 μm, and over 70% have an average diameter of less than about 4 μm.

| STAGE NO. | Cut Diam. μm | Recovery Mass, ug | Mass/Stage % | Cum. % > | Cum. % < |
|---|---|---|---|---|---|
| Pre-separator | 10 | | 0.00 | 0.00 | 100.00 |
| 0 | 9 | 94.624 | 11.05 | 11.05 | 88.95 |
| 1 | 5.8 | 109.084 | 12.73 | 23.78 | 76.22 |
| 2 | 4.7 | 44.263 | 5.17 | 28.95 | 71.05 |
| 3 | 3.3 | 57.880 | 6.76 | 35.71 | 64.29 |
| 4 | 2.1 | 97.704 | 11.41 | 47.11 | 52.89 |
| 5 | 1.1 | 272.744 | 31.84 | 78.95 | 21.05 |
| 6 | 0.7 | 107.733 | 12.58 | 91.53 | 8.47 |
| 7 | 0.4 | 41.530 | 4.85 | 96.38 | 3.62 |
| FILTER | | 31.021 | 3.62 | 100.00 | 0.00 |
| | Sum | 856.58 ug | | | |

The table below provides an alternative format of the summary of Cascade impactor testing results, providing the results based on likely area of droplet impact in the mouthpiece/throat/coarse, respirable droplets, and fine droplets (Albuterol, 0.5%, Anderson Cascade, 28.3 lpm, 10 actuations).

| | |
|---|---|
| Mouthpiece Losses = | 109.4 mcg |
| Cascade Throat Losses = | 40.8 mcg |

-continued

| | | |
|---|---|---|
| Total Cascade Recovery = | 897.4 | mcg |
| Mouthpiece Losses | 12.2% | |
| Cascade Throat Losses | 4.6% | |
| Coarse Particles (>4.7 um) = | 203.7 | mcg |
| Coarse Particules Fraction (>4.7 um) = | 22.7% | |
| Respirable Dose (0.4-4.7 um) = | 621.9 | mcg |
| Respirable Fraction (0.4-4.7 um) = | 69.3% | |
| Fine Particles (<0.4 um) = | 31.0 | mcg |
| Fine Particule Fraction (<0.4 um) = | 3.5% | |
| Respiratory Delivery Rate (0.4-4.7 um) = | 62.2 | mcg/Actuation |
| MMAD = | 1.93 | um |
| Geometric StdDev (GSD) = | 1.96 | um |
| Mean +/- SD, N = | 30 | |

Figure 21A:
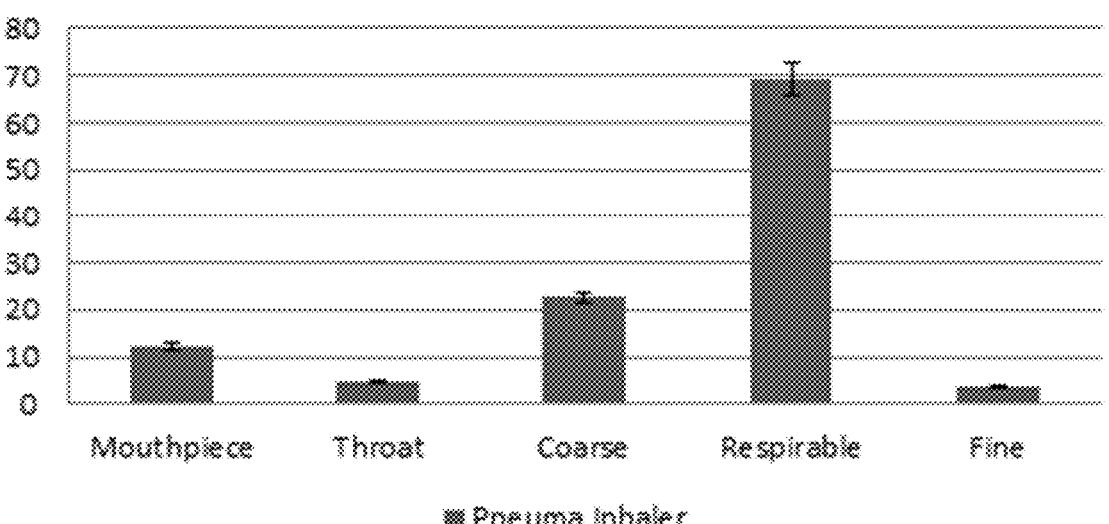
FIG. 21A provides a summary of the mass fraction collected during Anderson Cascade Impactor testing a droplet delivery device of disclosure.
Figure 21B:
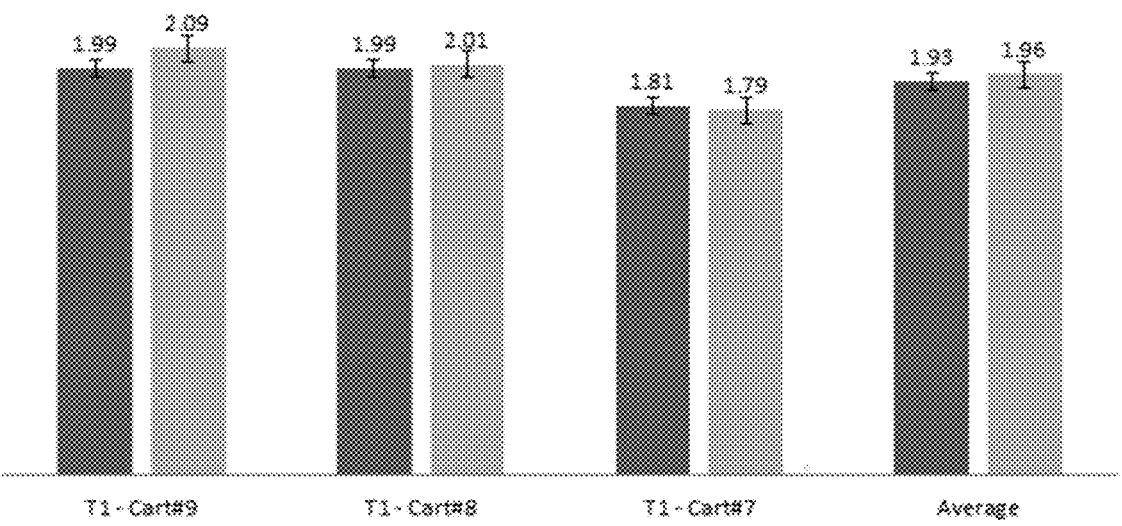
FIG. 21B is a summary of MMAD and GSD droplet data obtained during Anderson Cascade impactor testing of a droplet delivery device of the disclosure (3 cartridges, 10 actuations per cartridge; Albuterol, 0.5%, 28.3 lpm; 30 actuations total).
Figure 21C:
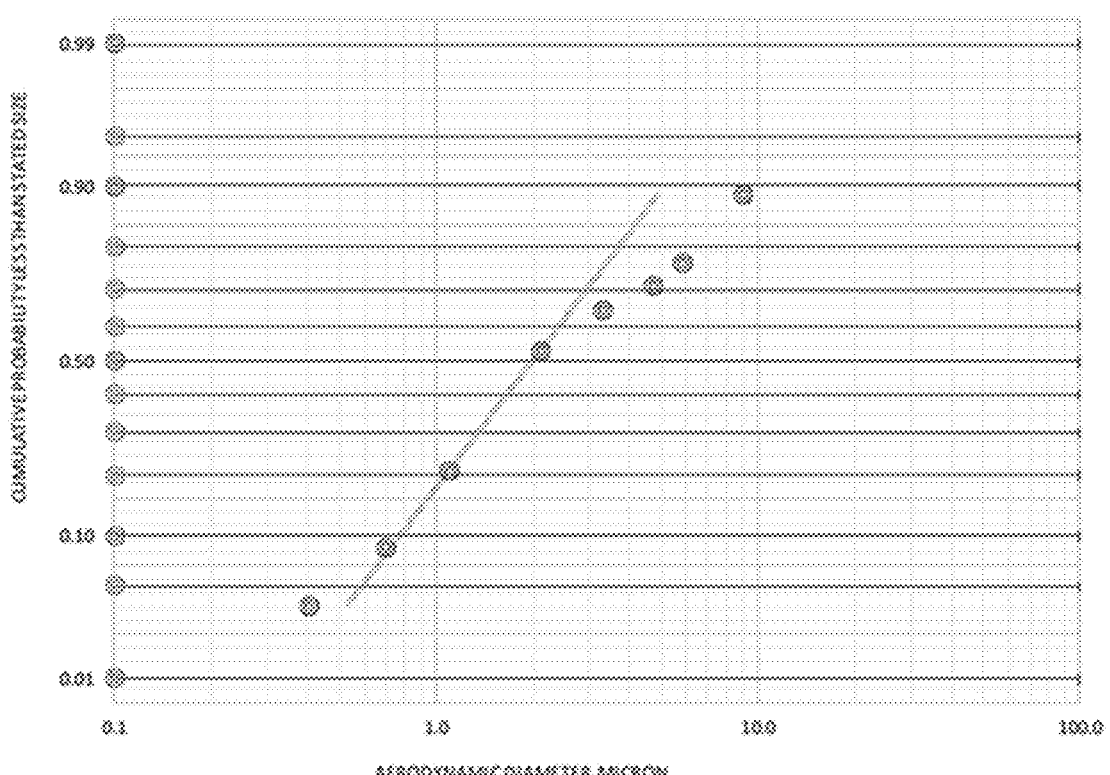
FIG. 21C and FIG. 21D are cumulative plots of the aerodynamic size distribution of data displayed in FIG. 21A.
Figure 21D:
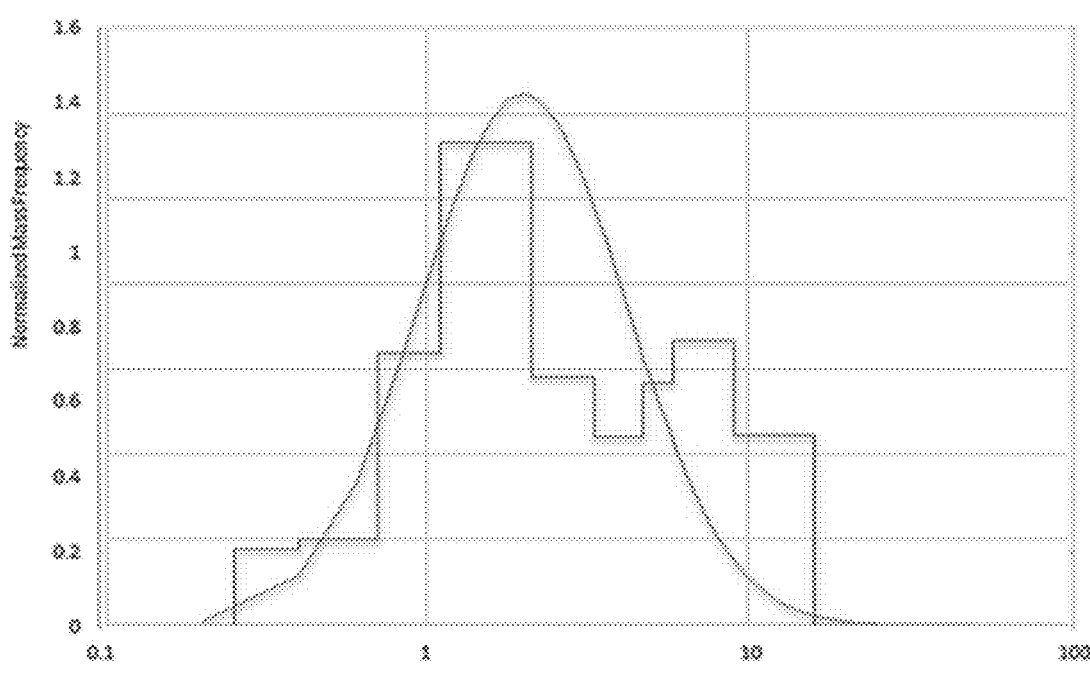
Figure 21E:
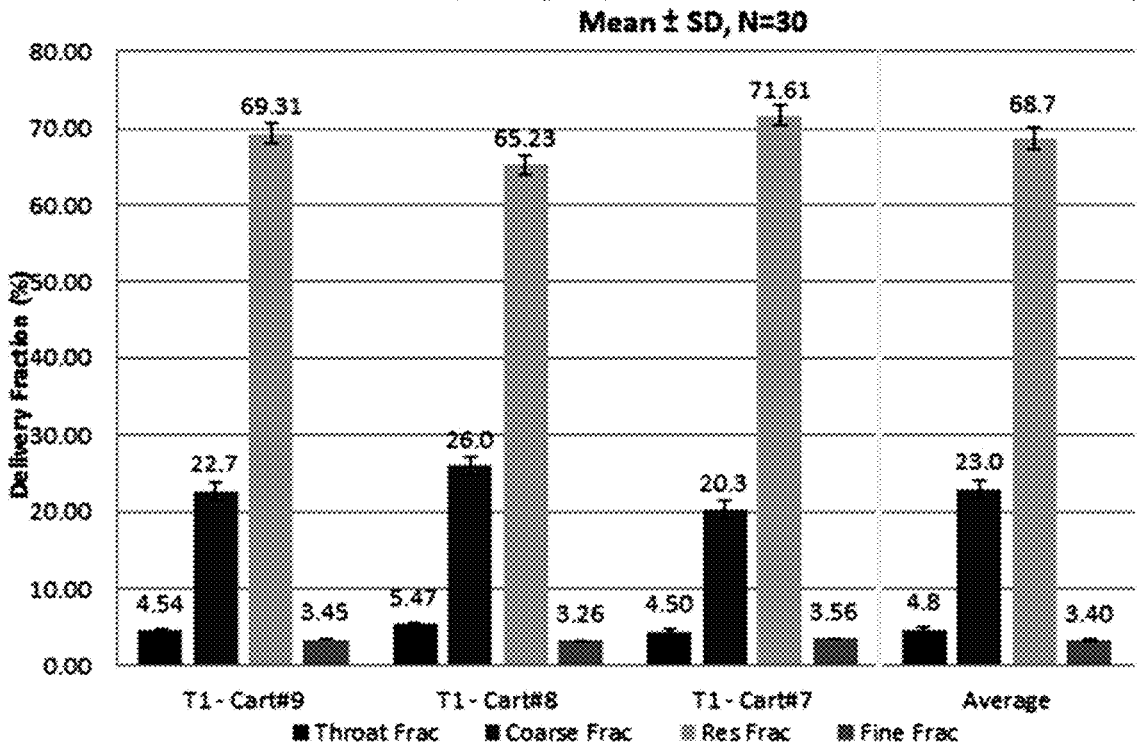
FIG. 21E is a summary of Throat, Coarse, Respirable and Fine Particle Fraction. Anderson Cascade Impact testing a droplet delivery device of disclosure (3 cartridges 10 actuations per cartridge; Albuterol, 0.5%, 28.3 lpm; 30 actuations total).

FIGS. 21A-21ED illustrate the same data in various compilations. FIG. 21A illustrates percentages of droplets deposited in the mouthpiece, throat, coarse, respirable, and fine. FIG. 21B illustrates the MMAD and GSD for all trial runs, and the average (3 cartridges 10 actuations per cartridge; Albuterol, 0.5%, 28.3 lpm; 30 actuations total). FIGS. 21C and 21D illustrate cumulative plots of the aerodynamic size distribution of the data from FIG. 21B. FIG. 21E illustrates throat, coarse, respirable and fine particle fraction in each trial run, and the average (3 cartridges 10 actuations per cartridge; Albuterol, 0.5%, 28.3 lpm; 30 actuations total).

Figure 22A:
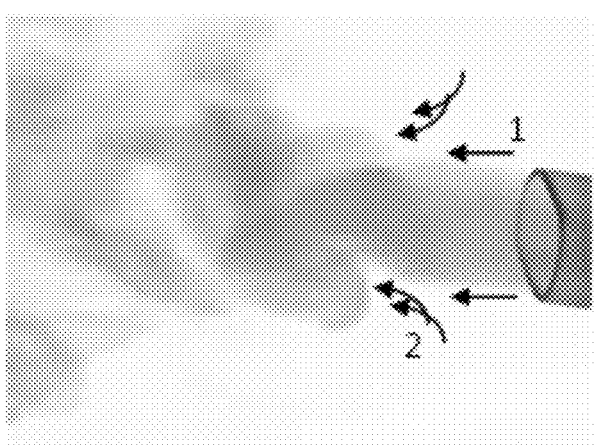
FIGS. 22A-22B are comparison of aerosol plumes from a droplet delivery device of the disclosure (FIG. 22A) and Respimat Soft Mist Inhale (FIG. 22B).
Figure 22B:
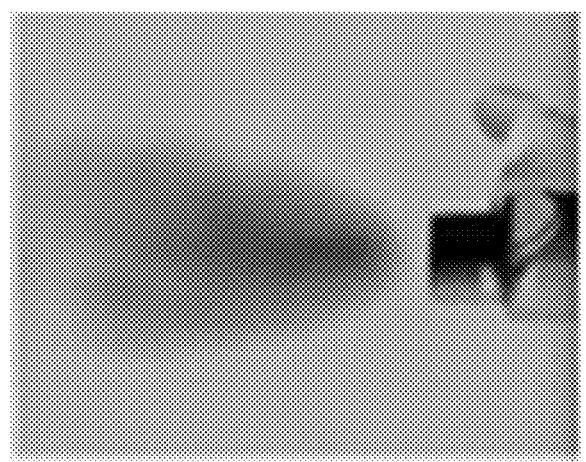

Example C: Comparative Droplet Generation Versus Combivent® Respimat® and Proair® HFA An in vitro study was conducted to evaluate and compare the droplet delivery device of the present disclosure with two predicated devices, the Combivent® Respimat® inhaler (Boehringer Ingelheim Pharmaceuticals Inc., Ridgefield CT) and the PROAIR® HFA (Teva Respiratory, LLC Frazer, PA). Initially, with reference to FIGS. 22A-22B, a comparison of the aerosol plumes generated from the droplet delivery device of the disclosure (the test device) and Respimat Softmist® Inhaler is illustrated. In FIG. 22A, the aerosol plume produced by the test device has two distinct flow patterns that are associated laminar flow (1) turbulent flow (2). As previously stated herein, turbulent flow and the formation of eddy currents are produced when droplets have MMAD diameters less than 5 μm and lead to the generation of entrained air. Contrasted to this, in FIG. 22B, the plume formed by the Respimat Softmist® Inhaler displays an aerosol plume is characteristic of droplets with high velocities and a wide range of droplet sizes having a high momentum and kinetic energy.

The devices were tested dosing Albuterol sulfate aerosol size distribution and mass delivery characteristics. As described herein, the droplet delivery device of the disclosure is a breath-actuated piezoelectric actuated device with removable and replaceable reservoir. In this example, the reservoir is designed to contain a therapeutic inhalation drug volume to provide 100-200 breath actuated doses per use. The predicate device Combivent Respimat is a propellant free, piston actuated, multidose metered inhaler, while the ProAIr HFA device is a CFC free, propellant based metered dose inhale.

A single test device body, and three (3) reservoir/ejector mechanism modules were tested. All predicate devices were tested in triplicate, for a total nine (9) Cascade Impactor trials. The devices of the disclosure were tested in triplicate with a new drug reservoir charged with 750 μl of 0.5% Albuterol sulfate for each of the three (3) tests.

Particle size distributions were measured using the Anderson Cascade Impactor (ACI) sampling at a constant 28.3 lpm during each test. The Anderson Cascade Impactor test is as described above in Example B, and can be used to determine the coarse particle mass, coarse particle fraction, respirable particle mass, respirable particle fraction, fine particle mass, and fine particle fraction of test aerosols. ACI data can also be used to calculate the Mass Median Aerodynamic Diameter (MMAD) and Geometric Standard Deviation (GSD) of the aerosol size distribution. Droplet classifications are defined as following: Coarse particle fraction, >4.7 μm; Respirable particle fraction, 0.4-4.7 μm; Fine particle fraction, <0.4 μm.

The predicate Combivent® Respimat® inhaler was tested using Combivent® Respimat® cartridges containing 20 mcg ipratropium bromide and 100 mcg albuterol equivalent to 120 mcg dose of albuterol sulfate delivery per actuation. The predicate PROAIR® HFA inhaler was evaluated with cartridges containing 108 mcg albuterol sulfate equivalent to 90 mcg delivered dose per actuation, while the droplet delivery device of the disclosure was evaluated using albuterol sulfate at a concentration of 5000 μg/ml equivalent to 0.5% albuterol and 85 mcg delivered dose per actuation.

Results from cascade impactor test trials for each inhaler tested in triplicate for Albuterol sulfate are as follows (FIGS. 23A-23B):

Average MMAD for: Test Device, 1.93±0.11, Combivent® Respimat®, 1.75±0.19, and PROAIR® HFA 2.65±0.05 μm for dispensing Albuterol sulfate.

Average GSD, for: Test Device: 1.96±0.16, Combivent® Respimat®, 2.79±0.25, and PROAIR® HFA, 1.48±0.02.

Figure 23A:
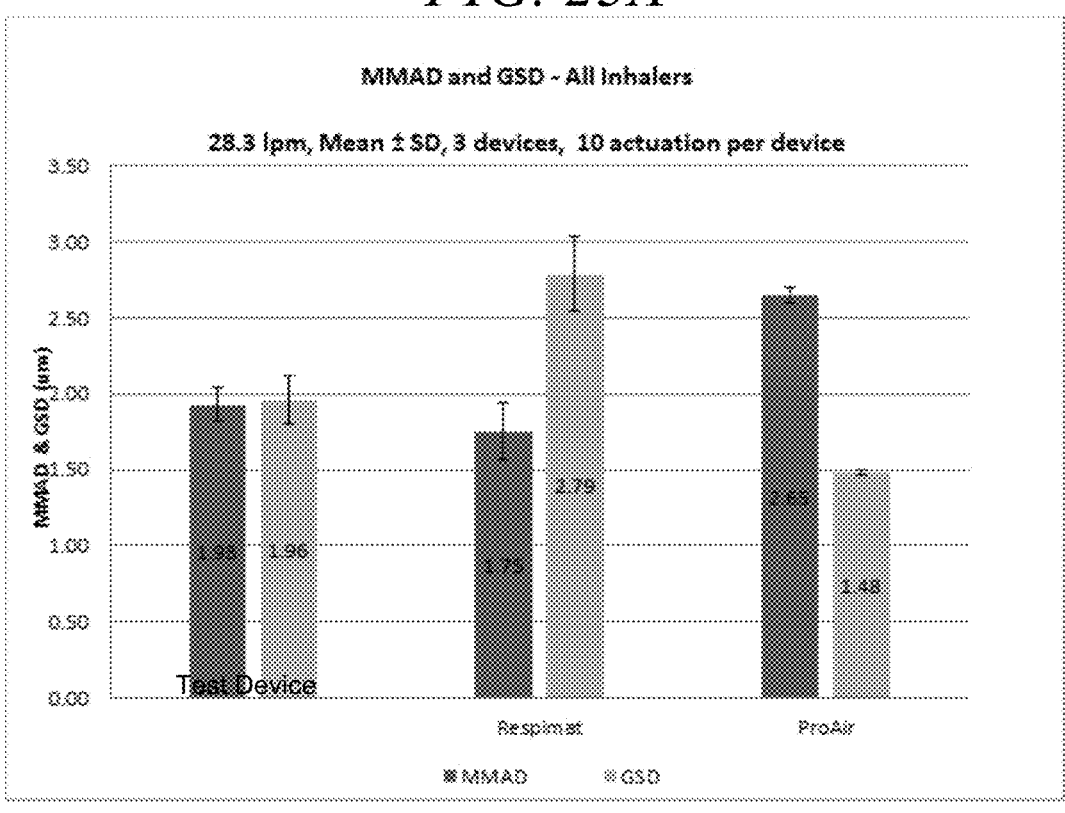
FIG. 23A is a comparison of MMAD and GSD data for a droplet delivery device of the disclosure, Respimat, and ProAir Inhaler Devices (Anderson Cascade Impactor Testing, 28.3 lpm, Mean+/−SD, 3 devices, 10 actuations per device).
Figure 23B:
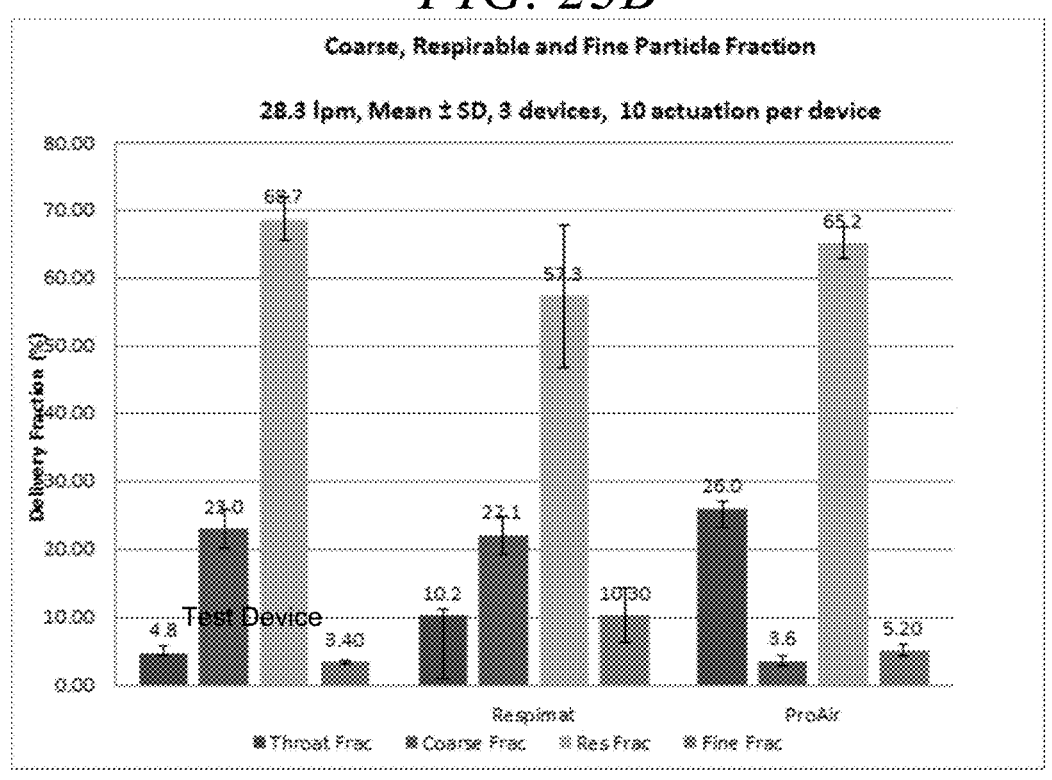
FIG. 23B is a summary of Coarse, Respirable and Fine Fractions for a droplet delivery device of the disclosure, Respimat, and ProAir Inhaler Devices (Anderson Cascade Impactor Testing, 28.3 lpm, Mean+/−SD, 3 devices, 10 actuations per device).

A summary and comparison of Cascade Impactor Testing of the test device, Combivent Respimat® and Proair® HFA inhalers is shown in in the tables below and in FIGS. 23A-23B. These data show the test device provides the highest respirable particle fraction for devices tested, (FIG. 23B) with a mean±standard deviation:

For the Test device, 68.7%±3.2%,
Combivent® Respimat®, 57.3%±10.5, and
PROAIR® HFA, 65.2%±2.4%.

| Features | Drug | Test Device | Respimat | ProAir |
|---|---|---|---|---|
| Number of Actuations | Albuterol | 1 | 1 | 1 |
| Actual Drug Concentration (μg/act) | Albuterol | 85.0 | 120.0 | 108.0 |
| Mouth (μg/act) | Albuterol | 24.3 +/- 12.6 | 22.6 +/- 1.9 | 16.1 +/- 4.3 |
| Total Cascade Recovery (μg/act) | Albuterol | 81.9 +/- 10.3 | 109.3 +/- 15 | 121.9 +/- 7.0 |
| Cascade Throat (μg/act) | Albuterol | 4.0 +/- 0.8 | 12.1 +/- 11.9 | 31.8 +/- 5.0 |
| Throat Fraction (%) | Albuterol | 4.8% +/- 0.5% | 10.2% +/- 9.2% | 26% +/- 2.9% |
| Coarse Particle Dose (μg/act) >4.7μ | Albuterol | 19.0 +/- 4.2 | 23.9 +/- 1.9 | 4.5 +/- 1.0 |

-continued

| Features | Drug | Test Device | Respimat | ProAir |
|---|---|---|---|---|
| Coarse Particle Frac (%) >4.7µ | Albuterol | 23% +/- 2.9% | 22.1% +/- 2.8% | 3.6% +/- 0.7% |

| Features | Drug | Pneuma Inhaler | Respimat | ProAir |
|---|---|---|---|---|
| Respirable Particle Dose (µg/act) (0.4-4.7 µm) | Albuterol | 56.2 +/- 6 | 61.7 +/- 5.5 | 79.4 +/- 2.7 |
| Respirable Particle Frac (%) (0.4-4.7 µm) | Albuterol | 68.7% +/- 3.2% | 57.3% +/- 10.5% | 65.2% +/- 2.4% |
| Fine Particle Dose (µg/act) (<0.4 µm) | Albuterol | 2.8 +/- 0.3 | 11.7 +/- 6.1 | 6.3 +/- 0.9 |
| Fine Particle Frac (%) (<0.4 µm) | Albuterol | 3.4% +/- 0.2% | 10.3% +/- 4.1% | 5.2% +/- 0.9% |
| MMAD (µm) | Albuterol | 1.93 +/- 0.11 | 1.75 +/- 0.19 | 2.65 +/- 0.05 |
| GSD (µm) | Albuterol | 1.96 +/- 0.16 | 2.79 +/- 0.25 | 1.48 +/- 0.02 |
| Confidence level of testing | The test and number of samples tested provide 95% confidence level. 3 cartridges/devices each 10 actuations. Total N = 30 actuations | | | |

| PNEUMA INHALER | Total Spray Mass Ejected from Cartridge (ml/min) |
|---|---|
| DEVICE #3 - B2D4; CARTRIDGE - B3C1 | 0.46 |
| DEVICE #2 - B2D3; CARTRIDGE - B3C5 | 0.46 |
| DEVICE # 1- B2D2; CARTRIDGE - B3C3 | 0.5 |
| Avg. | 0.47 |
| StDev | 0.02 |

Example D: Clinical Study—Albuterol Sulfate and Ipratropium Bromide

Using an exemplary ejector device of the disclosure (test device), a cross over clinical trial was conducted comparing the acute bronchodilatory effects of the test device using albuterol sulfate and ipratropium bromide versus no treatment in a group of patients with chronic obstructive pulmonary disease.

Up to 75 patients with COPD will be enrolled. To be eligible for the study, subjects at visit 1 must: 1) be previously diagnosed with COPD; 2) have at least a 10 pack year smoking history; 3) be prescribed one or more inhaled bronchodilators; 4) exhibit post bronchodilator FEV1≥25% and <70% predicted normal value using appropriate reference equations.

The study is a crossover, single center, 1 day lung function study to measure the acute bronchodilation effect of standard dose albuterol sulfate and ipratropium bromide using an test device of the disclosure in a group of COPD patients.

Subjects may undergo up to a 1 week screening period. If the patient is not using long acting beta agonists or long acting muscarinic antagonists and has not used a short acting bronchodilator in the previous 6 hours, no washout period is necessary and can immediately proceed with visit 2. If the subject is using a long acting beta agonist they will be washed out for 48 hours. If the subject is using a long acting muscarinic antagonist the washout period will be one week. During the washout period subjects will be allowed to continue to use inhaled corticosteroids (ICS), short acting beta agonists (SABA), short acting muscarinic antagonists (SAMA), leukotriene inhibitors, and phosphodiesterase 4 inhibitors. Subjects experiencing COPD exacerbations during the washout period will be excluded from the trial. Subjects who successfully complete the screening period will be included in the trial.

As described herein, the test devices include piezoelectric actuated ejector mechanisms integrated with reservoir. The reservoir mounts to a device housing. The device housing has 2 areas 1) a mouthpiece tube and 2) a handle. The patient breathes in through the mouthpiece tube to activate the ejector mechanism. The mouthpiece tube detaches from the housing and can be sterilized and reused or disposed of after patient use.

The primary efficacy endpoints will include change in FEV1 during 2 time periods: the 20 minutes before receiving a dose of albuterol sulfate and ipratropium bromide using the ejector device of the disclosure, and the 20 minutes after receiving a dose of albuterol sulfate and ipratropium bromide from the ejector device of the disclosure. Safety endpoint will include vital signs and changes in FEV1. The statistical analysis will include an analysis of the change in FEV1 using T-tests.

Interim results demonstrate the use of the ejector device of the disclosure provides a significant bronchodilatory effect versus no treatment. For instance, with partial enrollment, the following average FEV1 readings were obtained:

| Timepoint | FEV1 (Liters)* |
|---|---|
| Baseline 1 | 1.3733 |
| Baseline 2 (+20 minutes) | 1.4133 |
| Treatment 1 (+20 minutes after treatment) | 1.6688 |
| Treatment 2 (+60 minutes after treatment) | 1.6844 |
| Treatment 3 (+120 minutes after treatment) | 1.6522 |

*Mean baseline FEV1 for the group is 1.29 liters. Mean change in 20 min FEV1 is 220 cc with a p = 0.000012.

As shown in the table above, treatment with the ejector device of the disclosure improved FEV1 by an average of about 260-275 cc. This improvement is 1.2 to 2 times the increase in broncodilatory effect typically observed using standard manual inhalers with the same dose of active drug.

Example E: Clinical Study—Albuterol Sulfate

Using an exemplary droplet delivery device of the disclosure (test device), a cross over clinical trial was conducted comparing the acute bronchodilatory effects of the test device using albuterol sulfate versus the ProAir® HFA Inhaler in a group of patients with chronic obstructive pulmonary disease (COPD).

Up to 75 patients with COPD will be enrolled. To be eligible for the study, subjects at visit 1 must: 1) be previously diagnosed with COPD; 2) have at least a 10 pack year smoking history; 3) be prescribed one or more inhaled bronchodilators; 4) exhibit FEV1<70% or at least 10% lower than the predicted normal value using appropriate reference equations.

This is a crossover, single center, 2 to 3 day lung function study to measure the acute bronchodilation effect of standard dose albuterol sulfate using the test device in a group of COPD patients and to compare this to the same drug given with a predicate device, the ProAir HFA Inhaler, but at half the dose administered with the predicate device.

Subjects may undergo up to a 1 week screening period. If the patient is not using long acting beta agonists or long acting muscarinic antagonists and has not used a short acting bronchodilator in the previous 6 hours, no washout period is necessary and can immediately proceed with visit 2. If the subject is using a long acting beta agonist, they will be washed out for 48 hours. If the subject is using a long acting muscarinic antagonist, the washout period will be up to one week. During the washout period subjects will be allowed to continue to use inhaled corticosteroids (ICS), short acting beta agonists (SABA), short acting muscarinic antagonists (SAMA), leukotriene inhibitors, and phosphodiesterase 4 inhibitors. Subjects experiencing COPD exacerbations during the washout period will be excluded from the trial. Subjects who successfully complete the screening period will be included in the trial.

As described herein, the test devices include piezoelectric actuated ejector mechanisms integrated with reservoir. The reservoir mounts to a device housing. The device housing has 2 areas 1) a mouthpiece tube and 2) a handle. The patient breathes in through the mouthpiece tube to activate the ejector mechanism. The mouthpiece tube detaches from the housing and can be sterilized and reused or disposed of after patient use.

The primary efficacy endpoints will include change in FEV1 during 2 time periods: the 20 minutes before receiving a dose of albuterol sulfate and the 20 minutes after receiving a dose of albuterol sulfate using the test device of the disclosure. Safety endpoint will include vital signs and changes in FEV1. The statistical analysis will include an analysis of the change in FEV1 using T-tests.

Results demonstrate the use of the test device of the disclosure provides a significant bronchodilatory effect versus no treatment, and a similar but slightly improved bronchodilatory effect versus treatment with twice the dose using a predicate device, the ProAir HFA device. More particularly, there was a statistically significant improvement in FEV1 (120 ml) with the device at a 100 microgram dose of albuterol compared to no treatment. Further, it was unexpectedly found that the average improvement was 11.9 ml greater than the improvement seen with twice the dose of 200 micrograms using the predicate device, the ProAir HFA inhaler. In this regard, the test device of the disclosure was able to achieve a similar but slightly improved clinical efficacy at half the dose of the predicate device. The test device was able to delivery concentrated doses of a COPD medication and provide meaningful therapeutic efficacy, as compared to standard treatment options.

The below tables provide detailed data:

| Test Device | | | ProAir HFA | | |
|---|---|---|---|---|---|
| Baseline | Pre 20 min | Difference | Baseline | Pre 20 min | Difference |
| 0.54 | 0.49 | −0.05 | 0.65 | 0.64 | −0.01 |
| 1.3 | 1.33 | 0.03 | 1.14 | 1.21 | 0.07 |
| 0.92 | 1 | 0.08 | 1.09 | 1.02 | −0.07 |
| 1.26 | 1.32 | 0.06 | 1.18 | 1.3 | 0.12 |
| 1.59 | 1.64 | 0.05 | 1.33 | 1.39 | 0.06 |
| 0.63 | 0.68 | 0.05 | 0.76 | 0.74 | −0.02 |
| 0.68 | 0.84 | 0.16 | 0.8 | 0.76 | −0.04 |
| 1.09 | 1.01 | −0.08 | 1.28 | 1.23 | −0.05 |
| 0.85 | 0.85 | 0 | 1.13 | 1.13 | 0 |
| 1.22 | 1.16 | −0.06 | 1.08 | 1.07 | −0.01 |
| 1.28 | 1.24 | −0.04 | 2.14 | 2.11 | −0.03 |
| 2.15 | 2.13 | −0.02 | 1.18 | 1.16 | −0.02 |
| 0.98 | 1.04 | 0.06 | 1.36 | 1.46 | 0.1 |
| 1.35 | 1.43 | 0.08 | 0.89 | 0.95 | 0.06 |
| 1.05 | 1.24 | 0.19 | 1.46 | 1.48 | 0.02 |
| 1.41 | 1.53 | 0.12 | 0.97 | 1 | 0.03 |
| 0.53 | 0.41 | −0.12 | 0.86 | 1.03 | 0.17 |
| 0.68 | 0.63 | −0.05 | 0.63 | 0.65 | 0.02 |
| 1.45 | 1.77 | 0.32 | 1.67 | 1.7 | 0.03 |
| 2.04 | 2.15 | 0.11 | 1.08 | 1.07 | −0.01 |
| 0.97 | 1 | 0.03 | 1.9 | 1.95 | 0.05 |
| | | mean change 0.04381 | | | mean change 0.022381 |

| Test Device | | | ProAir HFA | | |
|---|---|---|---|---|---|
| Pre 20 min | 20 Post | Difference | Pre 20 min | 20 Post | Difference |
| 0.49 | 0.76 | 0.27 | 0.64 | 0.82 | 0.18 |
| 1.33 | 1.33 | 0 | 1.21 | 1.23 | 0.02 |
| 1 | 1.03 | 0.03 | 1.02 | 1 | −0.02 |
| 1.32 | 1.41 | 0.09 | 1.3 | 1.43 | 0.13 |
| 1.64 | 1.8 | 0.16 | 1.39 | 1.77 | 0.38 |
| 0.68 | 0.82 | 0.14 | 0.74 | 0.86 | 0.12 |
| 0.84 | 0.92 | 0.08 | 0.76 | 0.91 | 0.15 |
| 1.01 | 1.09 | 0.08 | 1.23 | 1.29 | 0.06 |
| 0.85 | 1.05 | 0.2 | 1.13 | 1.15 | 0.02 |
| 1.16 | 1.36 | 0.2 | 1.07 | 1.13 | 0.06 |
| 1.24 | 1.33 | 0.09 | 2.11 | 2.42 | 0.31 |
| 2.13 | 2.31 | 0.18 | 1.16 | 1.47 | 0.31 |
| 1.04 | 1.02 | −0.02 | 1.46 | 1.56 | 0.1 |
| 1.43 | 1.46 | 0.03 | 0.95 | 1.17 | 0.22 |
| 1.24 | 1.39 | 0.15 | 1.48 | 1.66 | 0.18 |
| 1.53 | 1.41 | −0.12 | 1 | 0.92 | −0.08 |
| 0.41 | 1.17 | 0.76 | 1.03 | 0.52 | −0.51 |
| 0.63 | 0.67 | 0.04 | 0.65 | 0.72 | 0.07 |
| 1.77 | 1.79 | 0.02 | 1.7 | 1.94 | 0.24 |
| 2.15 | 2.25 | 0.1 | 1.07 | 1.09 | 0.02 |
| 1 | 1.05 | 0.05 | 1.95 | 2.27 | 0.32 |
| | mean change | 0.120476 | | mean change | 0.108571 |

Example F: Delivery of Large Molecules—Local and Systemic Delivery

Using an exemplary droplet delivery device of the disclosure, testing is conducted to verify that large molecules including epidermal growth factor receptor (EGFR) monoclonal antibody, bevacizumab (Avastin), adalimumab (Humira) and etanercept (Enbrel) is not denatured or degraded by ejection through the device of the disclosure, and to verify that local pulmonary delivery and/or systemic delivery of the active agent is achieved.

Droplet Characterization: To verify droplet generation, droplet impactor studies may be performed, as described herein.

Gel Electrophoresis: To determine the stability of active agent after droplet generation, the generated stream of droplets including the active agent is collected and the molecular weight of the active agent is verified using gel electrophoresis. Gel electrophoresis will show that there is negligible change in the electrophoretic mobility, and hence the molecular weight, of the post-aerosol active agent from that of the control, i.e., whole EGFR antibodies, bevacizumab, adalimumab, or etanercept. The gel will also show that is no evidence of smaller fragments of the protein on the gel, further confirming that the aerosol generation will not cause any appreciable protein degradation. In addition, the gel will show no apparent aggregation of the antibody or protein, which is significant as many inhalation devices have been reported to be prone to protein aggregation and hence unsuitable for the pulmonary delivery of large macromolecules such as proteins and antibodies.

Size Exclusion Chromatography (SEC): Alternately, to determine the stability of active agent after droplet generation, the generated stream of droplets including the active agent may be collected and SEC-HPLIC may be employed to monitor for any changes in large molecule aggregation and protein fragment content. Soluble protein aggregates and protein fragment content may be calculated by comparing respective peak area under the SEC-HPLC curve of dispensed protein solutions with controls (solutions remaining in the device reservoir).

Drug solutions for testing include Enbrel, (ENBREL® single-use prefilled syringes in 25 mg (0.51 mL of a 50 mg/mL solution of etanercept), and insulin, (Humalog, 200 units/ml, 3 ml kwikpens)

ENBREL® (etanercept) is a dimeric fusion protein consisting of the extracellular ligand-binding portion of the human 75 kilodalton (p75) tumor necrosis factor receptor (TNFR) linked to the Fc portion of human IgG1. The Fc component of etanercept contains the CH2 domain, the CH3 domain and hinge region, but not the CH1 domain of IgG1. Etanercept is produced by recombinant DNA technology in a Chinese hamster ovary (CHO) mammalian cell expression system. It consists of 934 amino acids and has an apparent molecular weight of approximately 150 kilodaltons.

SEC is performed with a Yarra™ 3 μm SEC-2000 LC column 300×7.8 mm, SecurityGuard cartridge kit and SecurityGuard cartridges GFC-2000, 4×3 mm ID. Fifty microliters of Enbrel from the syringe (ENBREL® single-use prefilled syringes in 25 mg/0.51 mL of a 50 mg/mL solution of etanercept) is diluted (4:1) (4 parts, 200 mcl of the mobile phase buffer solution to 1 part, 50 mcl Enbrel from syringe). Fifty microliter of the diluted Enbrel is injected and separation was performed at a flow rate of 1.0 ml/min. The mobile phase buffer system included a PHOS. BUFF. SALINE. (PBS) solution and 0.025% NaN$_3$, pH 6.8. UV detection is performed at 280 nm.

To calculate and compare effects of droplet generation through an ejector mechanism of the disclosure, the total area under the curve of the UV signal at 280 nm versus elution time for controls is compared with the aerosolized samples, which is set to 100%.

Fifty microliters (mcl) of insulin, (Humalog, 200 units/ml, 3 ml Kwikpens) is directly drawn from the Kwikpen and injected into the SEC column for analysis while 200 mcl of the Kwikpen solution is directly injected into the ampule/cartridge before actuation and aerosol generation with the test device. Aerosol collection and SEC is performed in a similar fashion as for the Enbrel analysis and aerosol collection.

An ampule/cartridge is filled with either 0.20 ml of Enbrel® (50 mg/ml) diluted 4:1 (10 mg/ml) (4 parts (200 mcl) of PBS and 0.025% NaN$_3$ and 1 part (50 mcl of Enbrel solution from the syringe). After 20 actuations and aerosolization, about 150 mcl of the aerosolized Enbrel solution is recovered and collected in the polypropylene tube located below the ejector mechanism. The control consists of the diluted Enbrel solution, 50 mcl of which is injected into the SEC column for analysis.

Insulin solutions from a Humalog, 200 units/ml, 3 ml Kwikpen is drawn with a syringe and 200 mcl is injected directly into the reservoir/ejector mechanism module and mounted onto a test device before actuation. Aerosol emerging from the test device is collected by placing a 0.5 ml polypropylene test tube directly below the aperture plate. Twenty actuations aerosolization resulted in the recovery of about 150 mcl of the aerosol insulin spray. Fifty microliters of the collected aerosol spray is injected onto the SEC column for analysis, while 50 mcl of the Kwikpen insulin solution is injected onto the SEC column for control samples.

Results; Enbrel

Figures 24A, 24B:
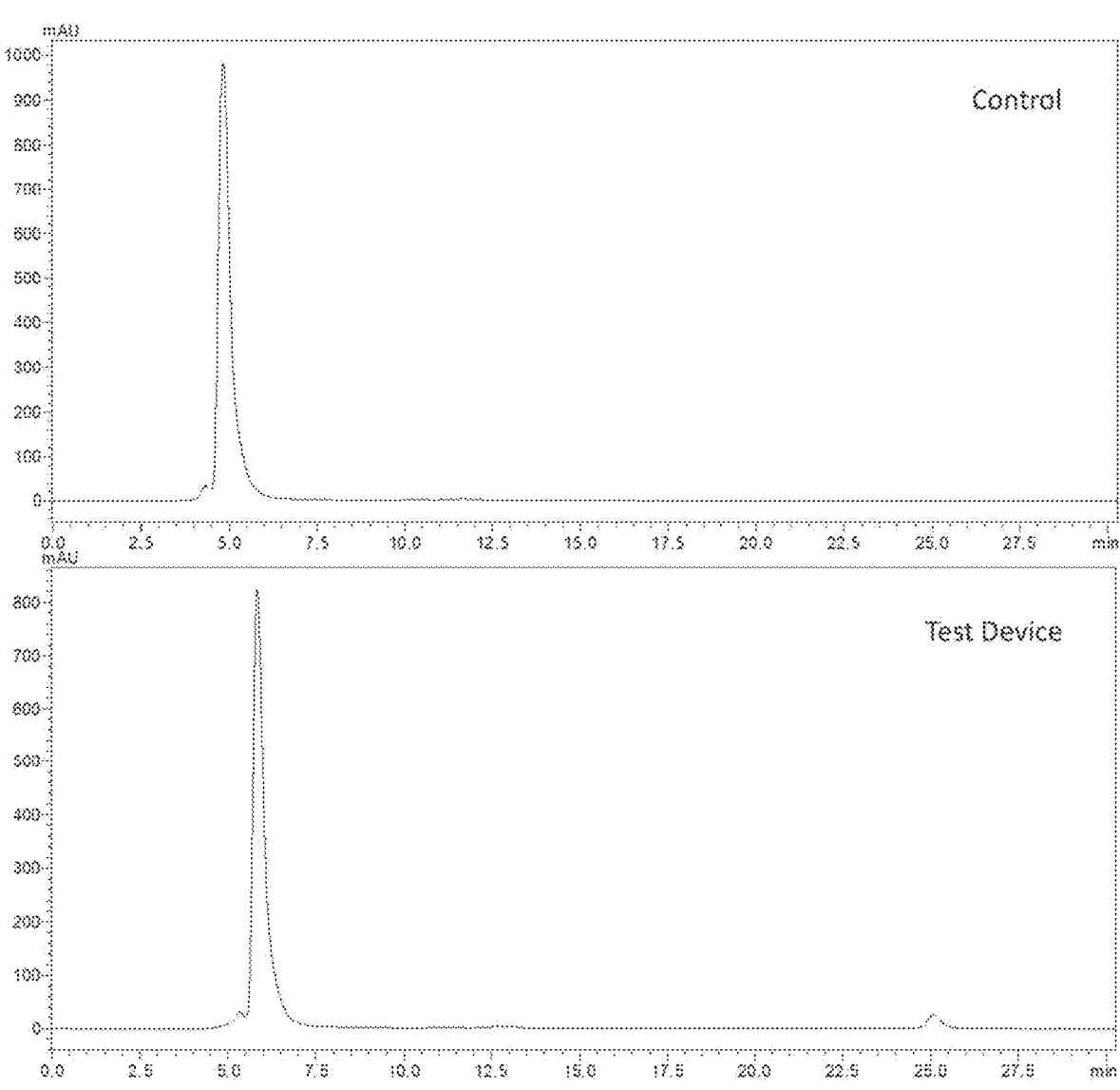
FIGS. 24A-24B, show SEC chromatographs of control (FIG. 24A) and aerosolized Enbrel solutions (FIG. 24B) produced using a droplet delivery device of the disclosure.

Referring to FIG. 24A-24B, are SEC chromatographs of Enbrel® diluted 4:1, (10 mg/ml) control (FIG. 24A) and aerosolized Enbrel solutions (FIG. 24B) collected from the test device after actuation. A single main peak is evident in chromatographs of the aerosolized Enbrel solution with an elution time of about 25 minutes. The tables below compare areas under the UV curves for the various peaks emerging at specified elution times (min) for controls and aerosolized Enbrel solutions.

Enbrel Stability Studies: Aerosol Generation using Test Device

| | Peak Area % | | | | |
| | Peak 1 (Ret Time) | Peak 2 (Ret Time) | Peak 3 (Ret Time) | Peak 4 (Ret Time) | Peak 5 (Ret Time) |
|---|---|---|---|---|---|
| control 1 | 2.428 (4.336) | 96.676 (4.827) | 0.373 (11.628) | 0 | 0 |
| control 2 | 3.041 (5.326) | 95.909 (5.785) | 0.351 (12.605) | 0 | 0 |
| Aerosolized S1 | 2.796 (5.372) | 90.789 (5.853) | 0.424 (12.675) | 0.357 (13.051) | 5.130 (25.139) |
| Aerosolized S1 | 3.476 (5.338) | 92.112 (5.821) | 0.361 (12.625) | 0.352 (13.020) | 3.428 (25.082) |

| | Peak 4 | Peak 5 |
|---|---|---|
| Aerosolized S1 | 0.357 | 5.123 |
| Aerosolized S2 | 0.352 | 3.428 |
| Avg. | 0.3545 | 4.2755 |
| Std. Dev. | 0.0035 | 1.1985 |

These data demonstrate that the test device can deliver 95.4% of Enbrel that is structurally unchanged after delivering an aerosol dose, while only 4.6% of the dose leads to formation of molecular fragments with elution times of 13 and 25 minutes.

Gravimetric analysis was performed by weighing the Enbrel solution filled ampule before and after dosing. The average of five doses (actuations) were analyzed with an average of 4.25 mg+/−0.15 mg. The total delivered dose of Enbrel per actuation is therefore 42.5 mcg per actuation. In comparison, actuation of distilled water with the same ampule resulted in a delivered dose of 9.26 mg.+/−1.19 mg.

Results; Insulin

Figures 25A, 25B:
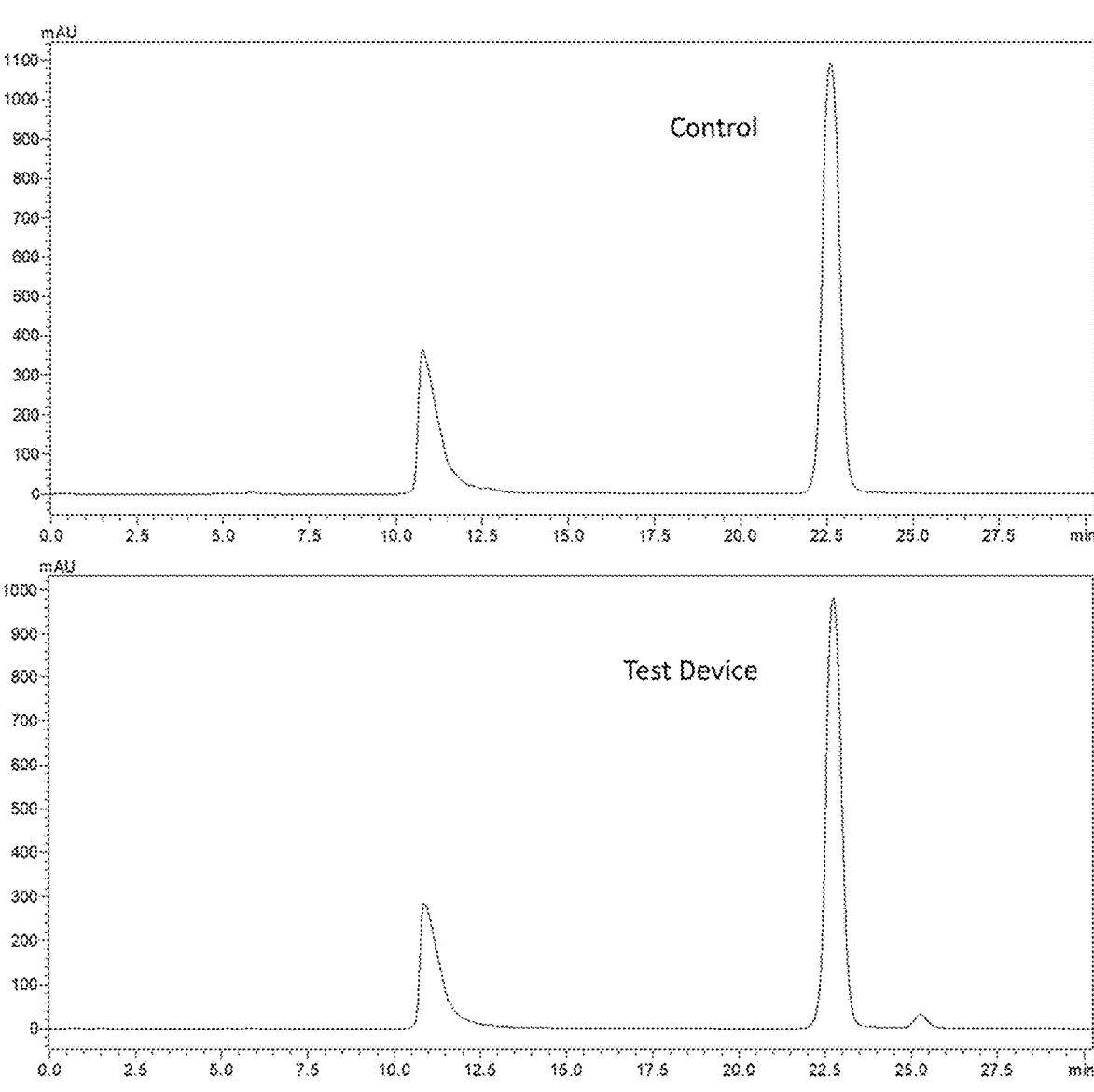
FIGS. 25A-25B, show SEC chromatographs of control (FIG. 25A) and aerosolized Insulin solutions (FIG. 25B) produced using a droplet delivery device of the disclosure.

Referring to FIGS. 25A-25B, are SEC chromatographs of Insulin from Kwikpen (200 U/ml; 34.7 mcg/U; 6.94 mg/ml) as control (FIG. 25A) and aerosolized from the test device (FIG. 25B). About 150 mcl of aerosolized Insulin solutions were collected from the test device after actuation. A single major peak is evident in the chromatograph of the aerosolized Insulin solution with an elution time of about 25 minutes. The tables below compare areas under the UV curves for the various peaks emerging at specified elution times for controls and aerosolized Insulin solutions. Retention times are in minutes.

Insulin Stability Studies: Aerosol Generation using Pneuma Inhaler Device

| | Peak Area % | | |
| | Peak 1 (Ret Time) | Peak 2 (Ret Time) | Peak 3 (Ret Time) |
|---|---|---|---|
| control 1 | 29.926 (10.786) | 69.630 (22.603) | 0 |
| Aerosolized S1 | 28.721 (10.823) | 67.807 (22.508) | 2.797 (25.017) |
| Aerosolized S2 | 27.881 (10.878) | 69.780 (22.726) | 2.184 (25.247) |

| | Peak 3 |
|---|---|
| Aerosolized S1 | 2.797 |
| Aerosolized S2 | 2.184 |
| Avg. | 2.4905 |
| Std. Dev. | 0.4335 |

These data demonstrate that the test device can deliver 97.5% of the ejected dose of Insulin that is structurally unchanged while 2.5% of the ejected dose forms a fragment which elutes at ~25 minutes.

Gravimetric analysis was performed by weighing the Insulin solution filled ampule before and after dosing. The average of five doses (actuations) were analyzed with an average of 5.01 mg+/−0.53 mg. The total delivered dose of Insulin per actuation is therefore 34.8 mcg per actuation.

Antibody/Protein Binding Assay: The activity of the aerosolized antibody or protein is demonstrated by testing its ability to bind to its antigen or target on a cell surface, i.e., EGFR, TNFα, etc. Flow cytometry data of cells incubated with either aerosolized or non-aerosolized active agent will reflect activity. Specifically, the data will show a shift in the fluorescence intensity of the cells incubated with non-aerosolized fluorescently labelled active agent compared to that for the untreated cells. A similar shift will be obtained with cells incubated with aerosolized active agent, suggesting that the post-aerosolized active agent retains its immunoactivity and hence its ability to bind to its target receptor on the cell surface.

Clinical/In Vivo Testing: Using an exemplary ejector device of the disclosure, as generally shown in FIGS. 1A-1E, a clinical trial is conducted to assess pharmacokinetic data following administration of large molecule active agents. pK data will verify that large molecule active agents are successfully systematically administered.

What is claimed is:

1. An electronically actuated droplet delivery device comprising:

a housing including a mouthpiece located at an airflow exit side of the housing;

a fluid reservoir disposed within or in fluid communication with the housing;

an electronically actuated aperture plate having a plurality of openings formed through its thickness wherein the aperture plate is in fluid communication with the fluid reservoir;

an electronic actuator operably coupled to oscillate the aperture plate at a frequency that generates an ejected stream of droplets; and an ejector closure coupled to the housing that opens and closes relative to the aperture plate.

2. The droplet delivery device of claim 1, wherein the ejector closure includes a sliding seal plate.

3. The droplet delivery device of claim 2, wherein the ejector closure is operably coupled to a motor.

4. The droplet delivery device of claim 3, wherein the ejector closure resists fluid evaporation from the aperture plate when in a closed position.

5. The droplet delivery device of claim 4, wherein the ejector closure is operably coupled to a sensor to prevent actuation of the aperture plate when the ejector closure is not open.

6. The droplet delivery device of claim 3, wherein the ejector closure is operably coupled to a sensor to prevent actuation of the aperture plate when the ejector closure is not open.

7. The droplet delivery device of claim 3, wherein the ejector closure is configured to close after a predetermined time interval following actuation of a dose of droplets.

8. The droplet delivery device of claim 3, wherein the ejector closure is configured to open when the droplet delivery device is powered on.

9. The droplet delivery device of claim 2, wherein the ejector closure resists fluid evaporation from the aperture plate when in a closed position.

10. The droplet delivery device of claim 9, wherein the ejector closure is operably coupled to a sensor to prevent actuation of the aperture plate when the ejector closure is not open.

11. The droplet delivery device of claim 2, wherein the ejector closure is operably coupled to a sensor to prevent actuation of the aperture plate when the ejector closure is not open.

12. The droplet delivery device of claim 2, wherein the ejector closure is configured to close after a predetermined time interval following actuation of a dose of droplets.

13. The droplet delivery device of claim 2, wherein the ejector closure is configured to open when the droplet delivery device is powered on.

14. The droplet delivery device of claim 1, wherein the ejector closure is operably coupled to a motor.

15. The droplet delivery device of claim 14, wherein the ejector closure resists fluid evaporation from the aperture plate when in a closed position.

16. The droplet delivery device of claim 15, wherein the ejector closure is operably coupled to a sensor to prevent actuation of the aperture plate when the ejector closure is not open.

17. The droplet delivery device of claim 15, wherein the ejector closure is configured to close after a predetermined time interval following actuation of a dose of droplets.

18. The droplet delivery device of claim 15, wherein the ejector closure is configured to open when the droplet delivery device is powered on.

19. The droplet delivery device of claim 14, wherein the ejector closure is operably coupled to a sensor to prevent actuation of the aperture plate when the ejector closure is not open.

20. The droplet delivery device of claim 14, wherein the ejector closure is configured to close after a predetermined time interval following actuation of a dose of droplets.

21. The droplet delivery device of claim 14, wherein the ejector closure is configured to open when the droplet delivery device is powered on.

22. The droplet delivery device of claim 1, wherein the ejector closure resists fluid evaporation from the aperture plate when in a closed position.

23. The droplet delivery device of claim 22, wherein the ejector closure is operably coupled to a sensor to prevent actuation of the aperture plate when the ejector closure is not open.

24. The droplet delivery device of claim 1, wherein the ejector closure is operably coupled to a sensor to prevent actuation of the aperture plate when the ejector closure is not open.

25. The droplet delivery device of claim 1, wherein the ejector closure is configured to close after a predetermined time interval following actuation of a dose of droplets.

26. The droplet delivery device of claim 1, wherein the ejector closure is configured to open when the droplet delivery device is powered on.

27. The droplet delivery device of claim 1, wherein the fluid reservoir includes nicotine or a chemical that is in marijuana.

* * * * *